US011413242B2

(12) United States Patent
Peters

(10) Patent No.: US 11,413,242 B2
(45) Date of Patent: Aug. 16, 2022

(54) FORMULATIONS OF TIE-2 ACTIVATORS AND METHODS OF USE THEREOF

(71) Applicant: EyePoint Pharmaceuticals, Inc., Watertown, MA (US)

(72) Inventor: Kevin Peters, Cincinnati, OH (US)

(73) Assignee: EYEPOINT PHARMACEUTICALS, INC., Watertown, MA (US)

( * ) Notice: Subject to any disclaimer, the term of this patent is extended or adjusted under 35 U.S.C. 154(b) by 100 days.

(21) Appl. No.: 16/908,996

(22) Filed: Jun. 23, 2020

(65) Prior Publication Data
US 2020/0397697 A1  Dec. 24, 2020

Related U.S. Application Data

(60) Provisional application No. 63/009,083, filed on Apr. 13, 2020, provisional application No. 62/865,653, filed on Jun. 24, 2019.

(51) Int. Cl.
| | |
|---|---|
| *A61K 9/107* | (2006.01) |
| *A61K 9/08* | (2006.01) |
| *A61K 9/06* | (2006.01) |
| *A61K 9/00* | (2006.01) |
| *A61K 47/24* | (2006.01) |
| *A61K 47/32* | (2006.01) |
| *A61K 45/06* | (2006.01) |

(52) U.S. Cl.
CPC .......... *A61K 9/1075* (2013.01); *A61K 9/0014* (2013.01); *A61K 9/0048* (2013.01); *A61K 9/06* (2013.01); *A61K 9/08* (2013.01); *A61K 47/24* (2013.01); *A61K 47/32* (2013.01); *A61K 45/06* (2013.01)

(58) Field of Classification Search
CPC ............ A61K 2300/00; A61K 39/3955; A61K 38/179; A61K 2039/505; A61K 31/427; A61K 2039/54; A61K 31/426; A61K 9/0019; A61K 31/497; A61K 31/513; A61K 31/506; A61K 2039/507; A61K 2039/545; A61K 31/4439; A61K 31/538; A61K 47/26; A61K 47/40; A61K 47/6951; A61K 9/0051; A61K 9/0048; A61K 39/39541; A61K 45/06; A61K 31/00; A61K 38/45; A61K 39/395; A61K 31/137; A61K 31/16; A61K 31/216; A61K 47/10; A61K 47/24; A61K 47/32; A61K 9/0014; A61K 9/0043; A61K 9/0053; A61K 9/0073; A61K 9/06; A61K 9/08; A61K 9/1075; C07K 16/22; C07K 16/2896; C07K 2317/51; C07K 2317/76; C07K 2317/92; C07K 2317/24; C07K 16/28; C07K 2317/33; C07K 2317/515; C07K 2317/75; C07K 16/40; C07K 2317/31; C07K 2317/35; C07K 2317/64; C07K 2319/55; A61P 27/02; A61P 27/00; A61P 35/00; A61P 29/00; A61P 43/00; A61P 9/00; A61P 9/10; A61P 27/06; A61P 13/12; A61P 3/00; A61P 9/12; C07D 417/04; C07D 277/28; C07D 277/30; C07D 277/56; C07D 277/60; C07D 277/64; C07D 417/12
See application file for complete search history.

(56) References Cited

U.S. PATENT DOCUMENTS

| | | |
|---|---|---|
| 7,589,212 B2 | 9/2009 | Gray et al. |
| 7,622,593 B2 | 11/2009 | Gray et al. |
| 7,674,781 B2 | 3/2010 | Sheardown et al. |
| 7,795,444 B2 | 9/2010 | Gray et al. |
| 7,973,142 B2 | 7/2011 | Rotello et al. |
| 8,106,078 B2 | 1/2012 | Gray et al. |
| 8,188,125 B2 | 5/2012 | Gray et al. |
| 8,258,311 B2 | 9/2012 | Gray et al. |
| 8,329,916 B2 | 12/2012 | Amarasinghe et al. |
| 8,338,615 B2 | 12/2012 | Gray et al. |
| 8,524,235 B2 | 9/2013 | Rotello et al. |
| 8,569,348 B2 | 10/2013 | Shalwitz et al. |
| 8,846,685 B2 | 9/2014 | Gray et al. |
| 8,883,832 B2 | 11/2014 | Shalwitz et al. |
| 8,895,563 B2 | 11/2014 | Gray et al. |
| 8,920,841 B2 | 12/2014 | Sheardown et al. |
| 8,946,232 B2 | 2/2015 | Gray et al. |
| 8,999,325 B2 | 4/2015 | Peters et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,284,285 B2 | 3/2016 | Gray et al. |
| 9,440,963 B2 | 9/2016 | Peters et al. |
| 9,539,245 B2 | 1/2017 | Peters |
| RE46,592 E | 10/2017 | Gray et al. |

(Continued)

FOREIGN PATENT DOCUMENTS

| | | |
|---|---|---|
| WO | WO-2015138882 A1 | 9/2015 |
| WO | WO-2017053566 A1 | 3/2017 |

OTHER PUBLICATIONS

Amoozgar, et al., Sulfadiazine modified PDMS as a model material with the potential for the mitigation of posterior capsule opacification (PCO), Colloids Surf B Biointerfaces. Nov. 1, 2013;111:15-23.

(Continued)

*Primary Examiner* — Audrea B Coniglio
(74) *Attorney, Agent, or Firm* — Sterne, Kessler, Goldstein & Fox P.L.L.C.

(57) ABSTRACT

Disclosed herein are compounds effective for activation of Tie-2 and inhibition of HPTPβ. Further disclosed are formulations to increase the efficacy of the compounds that activate Tie-2 and inhibit HPTPβ.

26 Claims, 2 Drawing Sheets

(56) References Cited

U.S. PATENT DOCUMENTS

| | | | |
|---|---|---|---|
| 9,795,594 | B2 | 10/2017 | Gray et al. |
| 9,926,367 | B2 | 3/2018 | Rotello et al. |
| 9,949,956 | B2 | 4/2018 | Shalwitz et al. |
| 9,994,560 | B2 | 6/2018 | Janusz et al. |
| 10,150,811 | B2 | 12/2018 | Peters et al. |
| 10,220,048 | B2 | 3/2019 | Peters et al. |
| 10,253,094 | B2 | 4/2019 | Peters et al. |
| 10,329,357 | B2 | 6/2019 | Peters et al. |
| 10,463,650 | B2 | 11/2019 | Gray et al. |
| 10,597,452 | B2 | 3/2020 | Peters et al. |
| 10,604,569 | B2 | 3/2020 | Peters et al. |
| 10,611,908 | B2 | 4/2020 | Sheardown et al. |
| 2005/0085484 | A1* | 4/2005 | Mitchell ............ A61P 35/00 514/249 |
| 2009/0028946 | A1 | 1/2009 | Sheardown et al. |
| 2010/0303911 | A1 | 12/2010 | Sheardown et al. |
| 2011/0288062 | A1 | 11/2011 | Sheardown et al. |
| 2014/0275103 | A1 | 9/2014 | Peters et al. |
| 2018/0092883 | A1 | 4/2018 | Peters et al. |
| 2018/0265694 | A1 | 9/2018 | Sheardown et al. |

OTHER PUBLICATIONS

Bernier-Latmani, et al., All TIEd up: mechanisms of Schlemm's canal maintenance, The Journal of Clinical Investigation, 2017, vol. 127 (10), pp. 3594-3597.

C20/20, "Injectable Crosslinked Hydrogels for Posterior Protein Delivery" https://www.c2020hub.ca/crosslinked-hydrogels, retrieval date Sep. 23, 2020.

C20/20, "Mucoadhesive Micelle Nanocarriers" https://www.c2020hub.ca/micelles-technologies, retrieval date Sep. 23, 2020.

Fitzpatrick, et al., Development of injectable, resorbable drug-releasing copolymer scaffolds for minimally invasive sustained ophthalmic therapeutics, Acta Biomater, 2012, vol. 8(7); pp. 2517-2528.

Fitzpatrick, et al., Temperature-sensitive polymers for drug delivery, Expert Rev Med Devices. Jul. 2012;9(4):339-51. doi: 10.1586/erd.12.24. Review.

Jamard, et al., Nanogels of methylcellulose hydrophobized with N-tert-butylacrylamide for ocular drug delivery, Drug Deliv Transl Res., Dec. 6, 2016, vol. 6(6); pp. 648-659.

Kim, et al., Impaired angiopoietin/Tie2 signaling compromises Schlemm's canal integrity and induces glaucoma, The Journal of Clinical Investigation, 2017, vol. 127 (10, pp. 387-3896.

Lasowski, et al., Atropine and Roscovitine Release from Model Silicone Hydrogels, Optom Vis Sci. Apr. 2016;93(4):404-11.

Mequanint, et al., 2-methacryloyloxyethyl N-butylcarbamate: a new co-monomer for synthesis of polyurethane hydrogels with improved mechanical properties for biomedical applications, J Biomater Sci Polym Ed. 2005;16(10):1303-18.

Princz, et al., Heparin-modified dendrimer crosslinked collagen matrices for the delivery of heparin-binding epidermal growth factor, Journal Biomed Mater Res A., 2012; vol. 100(8), pp. 1929-1937.

Princz, et al., Modified dendrimer cross-linked collagen-based matrices, J Biomater Sci Polym Ed. 2012;23(17):2207-22.

Prosperi-Porta, et al., Phenylboronic-Acid-Based Polymeric Micelles for Mucoadhesive Anterior Segment Ocular Drug Delivery, Biomacromolecules, Apr. 11, 2016; vol. 17(4); pp. 1449-1457.

Prosperi-Porta, et al., Tunable release of ophthalmic therapeutics from injectable, resorbable, thermoresponsive copolymer scaffolds, J Biomed Mater Res B Appl Biomater, 2017, vol. 105(1); pp. 53-62.

Rahmani, et al., Optimizing electrostatic interactions for controlling the release of proteins from anionic and cationically modified alginate, Eur J Pharm Biopharm. Aug. 2017;117:232-243.

Rastegari, et al., The enzyme-sensitive release of prodigiosin grafted β-cyclodextrin and chitosan magnetic nanoparticles as an anticancer drug delivery system: Synthesis, characterization and cytotoxicity studies, Colloids Surf B Biointerfaces. Oct. 1, 2017;158:589-601.

Sheardown, et al., New biomaterials and ocular drug delivery, 2017, Acta Ophthalmologica, vol. 95, Issue S259.

Sheikholeslami, et al., Hydrophobically-modified poly(vinyl pyrrolidone) as a physically-associative, shear-responsive ophthalmic hydrogel, Experimental Eye Research, 2015, vol. 137; pp. 18-31.

Thomson et al., A lymphatic defect causes ocular hypertension and glaucoma in mice, The Journal of clinical Investigation, 2014, vol. 124 (10), pp. 4320-4324.

Wells, et al., Generic, anthracene-based hydrogel crosslinkers for photo-controllable drug delivery, Macromol Biosci, Jul. 7, 2011; vol. 11(7); pp. 988-998.

Zhang, et al., An Injectable Hydrogel Prepared Using a PEG/Vitamin E Copolymer Facilitating Aqueous-Driven Gelation, 2019, Bio Macromolecules, vol. 17; pp. 3648-3658.

Search Report issued in Great Britain Patent Application No. GB2009592.3 dated Jan. 28, 2021.

\* cited by examiner

FORMULATIONS OF TIE-2 ACTIVATORS AND METHODS OF USE THEREOF

CROSS REFERENCE

This application claims priority to U.S. Provisional Application No. 63/009,083, filed Apr. 13, 2020 and U.S. Provisional Application No. 62/865,653, filed Jun. 24, 2019, each of which is hereby incorporated by reference in its entirety.

BACKGROUND

Excipients such as antimicrobial preservatives, solubility enhancers, and delivery agents are used in pharmaceutical formulations containing peptides, proteins, and small molecules, for administration via a variety of routes, including parenteral, intravitreal, or topical administration. In addition to maintaining the stability of the active ingredients in pharmaceutical formulations, excipients can enhance the absorption of and prolong the activity of the active ingredient in the body. Further, formulation of pharmaceutical compositions as hydrogels, nanoparticles, or micelles can enhance the delivery and efficacy of the active agent.

INCORPORATION BY REFERENCE

Each patent, publication, and non-patent literature cited in the application is hereby incorporated by reference in its entirety as if each was incorporated by reference individually.

SUMMARY

In some embodiments, the invention provides a pharmaceutical composition comprising, in a unit dosage form: a Tie-2 activator; and a pharmaceutically-acceptable excipient that releases the Tie-2 activator from the unit dosage form at a rate that is about zero order with respect to the Tie-2 activator.

In some embodiments, the invention provides a pharmaceutical composition comprising, in a unit dosage form: a HPTPβ inhibitor; and a pharmaceutically-acceptable excipient that releases the HPTPβ inhibitor from the unit dosage form at a rate that is about zero order with respect to the HPTPβ inhibitor.

In some embodiments, the invention provides a method of treating a condition, the method comprising administering to a subject in need thereof a therapeutically-effective amount of a pharmaceutical composition comprising, in a unit dosage form: a Tie-2 activator; and a pharmaceutically-acceptable excipient that releases the Tie-2 activator from the unit dosage form at a rate that is about zero order with respect to the Tie-2 activator.

In some embodiments, the invention provides a method of treating a condition, the method comprising administering to a subject in need thereof a therapeutically-effective amount of a pharmaceutical composition comprising, in a unit dosage form: a HPTPβ inhibitor; and a pharmaceutically-acceptable excipient that releases the HPTPβ inhibitor from the unit dosage form at a rate that is about zero order with respect to the HPTPβ inhibitor.

DETAILED DESCRIPTION

Figure 1:
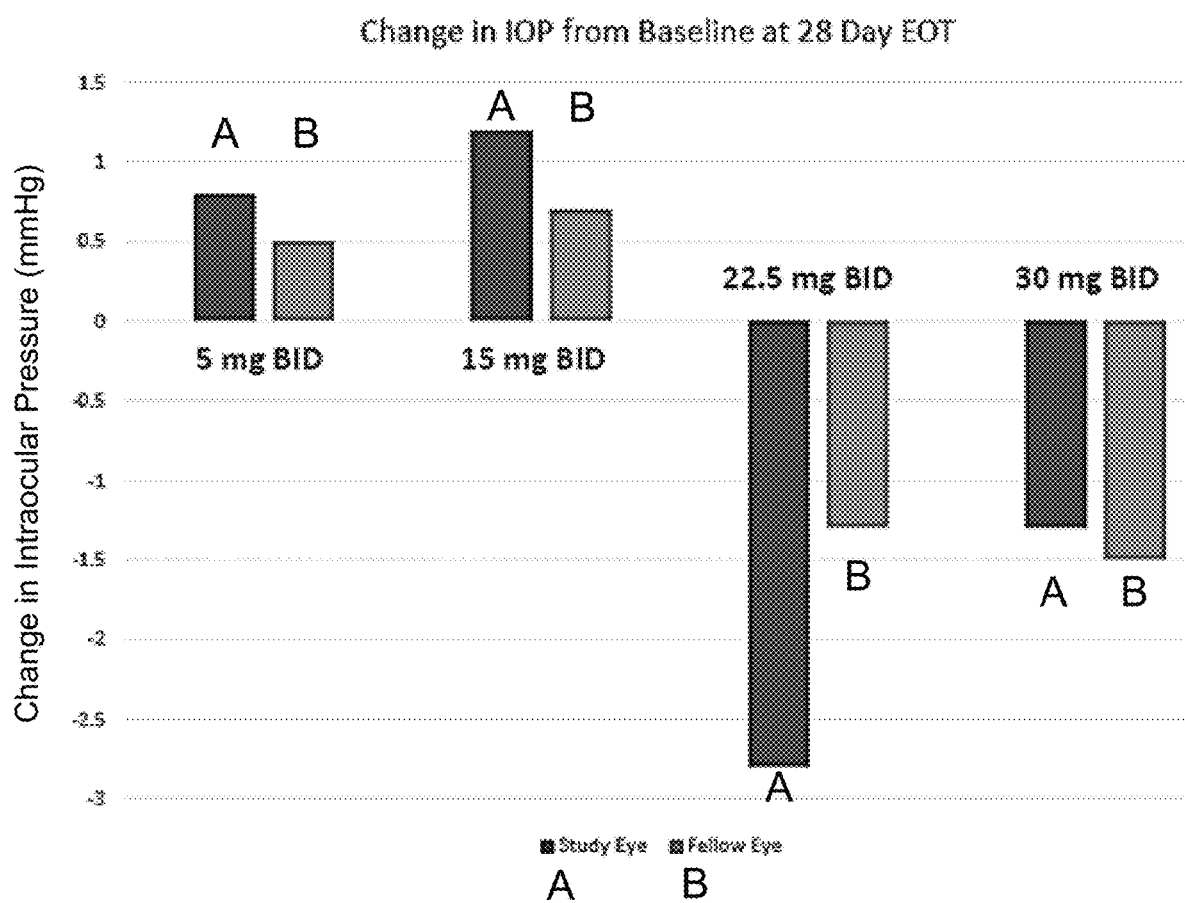
FIG. 1 illustrates changes in intraocular pressure from baseline. A: study eye; B: fellow eye.

Described herein are solubility-enhanced formulations containing compounds that can activate Tie-2 via inhibition of HPTPβ. The formulations described herein can be used for treating disorders characterized by vascular instability, angiogenesis, neovascularization, vascular leakage, and edema.

Tie-2 (tyrosine kinase with immunoglobulin and epidermal growth factor homology domains 2) is a membrane receptor tyrosine kinase expressed primarily in vascular endothelial cells and a subset of hematopoietic stem cells (HSCs) and macrophages. The principle regulators of Tie-2 phosphorylation are angiopoietin 1 (Ang-1) and angiopoietin 2 (Ang-2). Ang-1 is an agonist of Tie-2, and binding of Ang-1 to Tie-2 promotes receptor phosphorylation. Ang-2 is a Tie-2 ligand that acts in a context-dependent antagonistic or agonistic manner. Binding of Ang-1 to Tie-2 increases the level of endogenous Tie-2 receptor phosphorylation and initiates downstream AKT signaling. This binding initiates a signaling cascade that can induce distinctive vascular remodeling through highly organized angiogenesis and tightening of the endothelial cell junctions (endothelium cell proximity). Within the vascular endothelium, Ang-2-Tie-2 signaling promotes endothelial cell proximity. In the HSC microenvironment, Ang-2-Tie-2 signaling contributes in a paracrine manner to the long-term repopulation of HSCs.

Under physiological conditions, the duration of Tie-2 phosphorylation is regulated by the human protein tyrosine phosphatase beta (often abbreviated as HPTPβ or HPTP beta), which removes the phosphate from the Tie-2 receptor. By inhibiting HPTPβ, the level of Tie-2 phosphorylation substantially increases, restoring proper cell proximity. HPTPβ plays a functional role in endothelial cell proliferation, viability, differentiation, vasculogenesis, and angiogenesis. HPTPβ and vascular endothelial protein tyrosine phosphatase (VE-PTP; the mouse orthologue of HPTPβ) are expressed in vascular endothelial cells throughout development. A small molecule or biologic of the disclosure can activate Tie-2 downstream signaling by inhibiting HPTPβ/VE-PTP.

A therapy of the disclosure can be used to treat elevated intraocular pressure (TOP). Intraocular pressure arises from increased fluid pressure inside the eye. Pressure within the eye is maintained by the balance between the fluid entering the eye through the ciliary body and the fluid exiting the eye through the trabecular meshwork. The normal range of intraocular pressure is between about 10 mmHg to about 21 mmHg. Elevated intraocular pressure in the absence of glaucoma is referred to as ocular hypertension (OHT), which can cause damage to the trabecular meshwork and retinal ganglion cell death. High pressure in the eye can cause damage to the optic nerve and impair central and peripheral vision.

Failure to diagnose or treat symptoms of IOP, OHT, or glaucoma can lead to permanent vision loss. The glaucoma can be, for example, primary glaucoma, pseudoexfoliative glaucoma, pigmentary glaucoma, primary juvenile glaucoma, open angle glaucoma, wide-angle glaucoma, close-angle glaucoma, congenital glaucoma, acquired glaucoma, secondary glaucoma, inflammatory glaucoma, phacogenic glaucoma, or neovascular glaucoma. In some cases, a Tie-2 activator of the disclosure can stabilize vasculature associated with the trabecular meshwork, reducing intraocular pressure and treating ocular hypertension.

Tie-2 Activators.

Compounds disclosed herein can be effective as Tie-2 activators. The compounds can promote that activity, for example, by binding to or inhibiting HPTPβ. Such compounds can bind to HPTPβ, for example, by mimicking the binding mechanism of a native substrate, such as a phosphorylated compound. A compound can be a phosphate mimetic or bioisostere, for example, a sulfamic acid. The compound could also be derived from an amino acid building block or comprise an amino acid backbone for efficiency and economy of synthesis.

In some embodiments, a compound described herein is a compound of the formula:

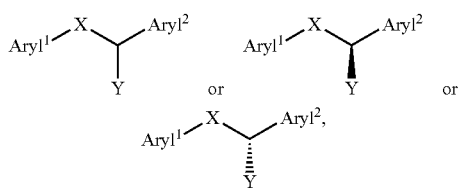

wherein:

Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thioether linkage, a carbamate linkage, a carbonate linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

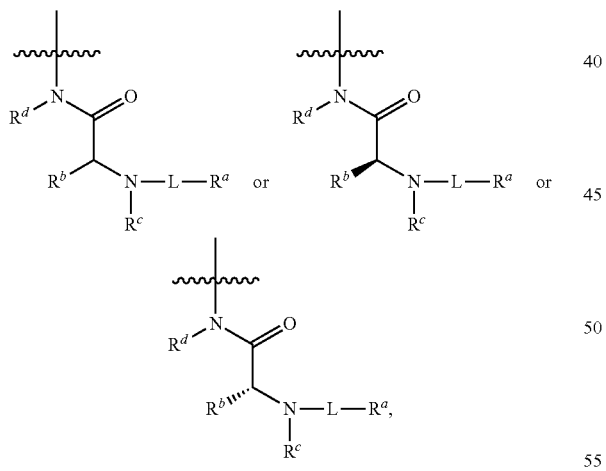

wherein:

L is alkylene, alkenylene, or alkynylene, any of which is substituted or unsubstituted, or together with the nitrogen atom to which L is bound forms an amide linkage, a carbamate linkage, or a sulfonamide linkage, or a chemical bond, or together with any of R$^a$, R$^b$, R$^c$, and R$^d$ forms a ring that is substituted or unsubstituted; R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^b$, R$^c$, and R$^d$ forms a ring that is substituted or unsubstituted; R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^a$, R$^c$, and R$^d$ forms a ring that is substituted or unsubstituted; R$^c$ is H or alkyl which is substituted or unsubstituted, or together with any of L, R$^a$, R$^b$, and R$^d$ forms a ring that is substituted or unsubstituted; R$^d$ is H or alkyl which is substituted or unsubstituted, or together with any of L, R$^a$, R$^b$, and R$^c$ forms a ring that is substituted or unsubstituted; and R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

In some embodiments, aryl$^1$ is substituted or unsubstituted phenyl, aryl$^2$ is substituted or unsubstituted heteroaryl, and X is alkylene. In some embodiments, aryl$^1$ is substituted phenyl, aryl$^2$ is substituted heteroaryl, and X is methylene.

In some embodiments, a compound is of the formula:

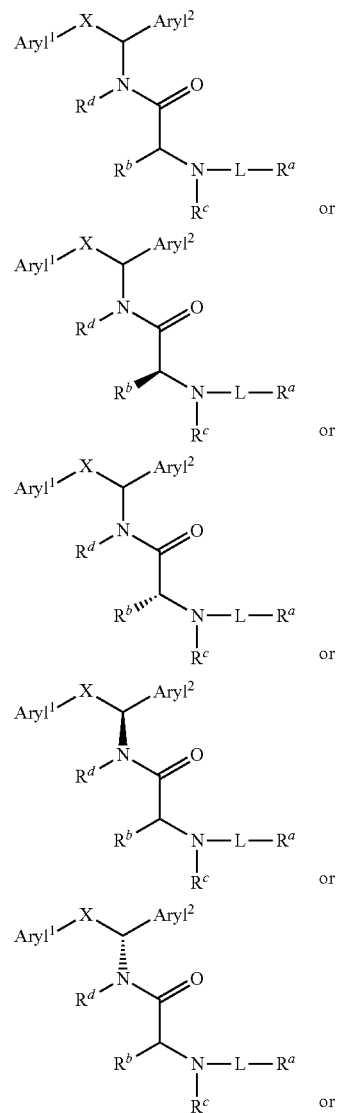

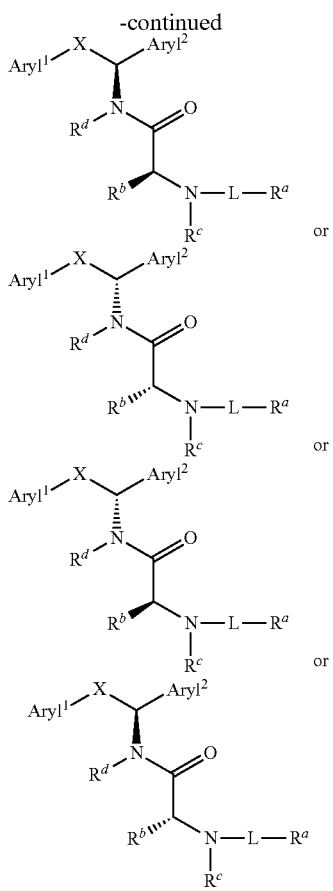

wherein aryl¹ is para-substituted phenyl, aryl² is substituted heteroaryl; X is methylene; L is alkylene, alkenylene, or alkynylene, any of which is substituted or unsubstituted, or together with the nitrogen atom to which L is bound forms an amide linkage, a carbamate linkage, or a sulfonamide linkage, or a chemical bond; $R^a$ is H, alkyl, alkenyl, alkynyl, aryl, arylalkyl, heterocyclyl, heterocyclylalkyl, heteroaryl, or heteroarylalkyl, any of which is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted; $R^c$ is H or alkyl which is substituted or unsubstituted; and $R^d$ is H or alkyl which is substituted or unsubstituted.

In some embodiments, aryl¹ is para-substituted phenyl; aryl² is a substituted thiazole moiety; X is methylene; L together with the nitrogen atom to which L is bound forms a carbamate linkage; $R^a$ is alkyl, which is substituted or unsubstituted; $R^b$ is arylalkyl, which is substituted or unsubstituted; $R^c$ is H; and $R^d$ is H.

In some embodiments, Aryl² is:

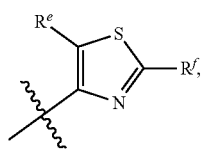

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted and $R^f$ is alkyl, aryl, heterocyclyl, or heteroaryl, any of which is substituted or unsubstituted. In some embodiments, aryl¹ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl. In some embodiments, aryl¹ is 4-phenylsulfamic acid; $R^a$ is alkyl; which is substituted or unsubstituted; $R^b$ is arylalkyl, which is substituted or unsubstituted; $R^e$ is H; and $R^f$ is alkyl.

In some embodiments, Aryl² is:

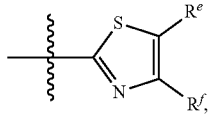

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted, $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted; and $R^f$ is alkyl, aryl, heterocyclyl, or heteroaryl, any of which is substituted or unsubstituted. In some embodiments, aryl¹ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl.

In some embodiments, a substituted phenyl group is:

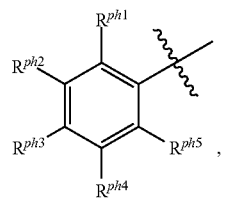

wherein:

each of $R^{ph1}$, $R^{ph2}$, $R^{ph3}$, $R^{ph4}$, and $R^{ph5}$ is independently H, OH, F, Cl, Br, I, CN, sulfamic acid, tosylate, mesylate, triflate, besylate, alkyl, alkenyl, alkynyl, an alkoxy group, a sulfhydryl group, a nitro group, an azido group, a sulfoxide group, a sulfone group, a sulfonamide group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl.

Illustrative compounds include the following:

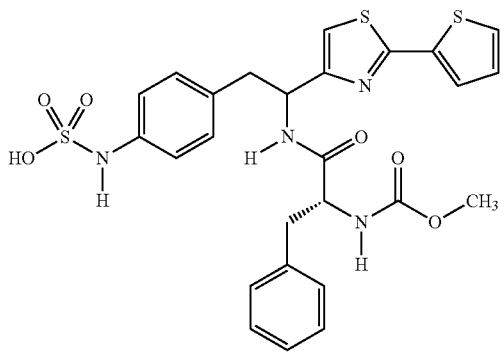

,

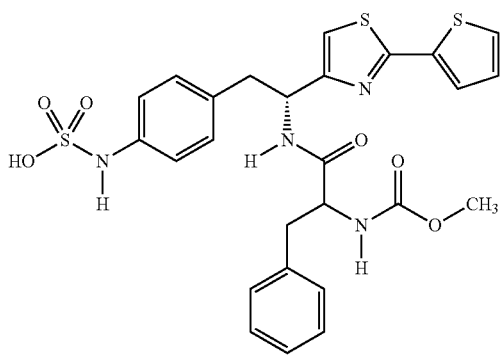

,

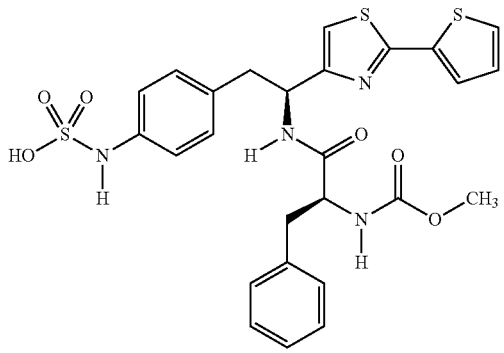

,

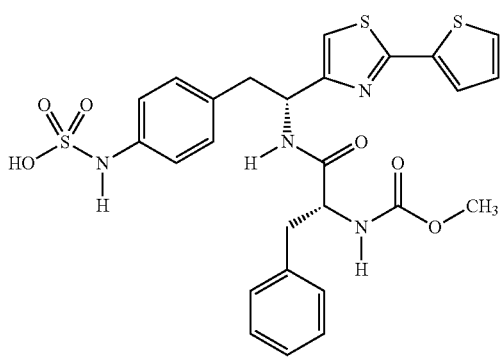

,

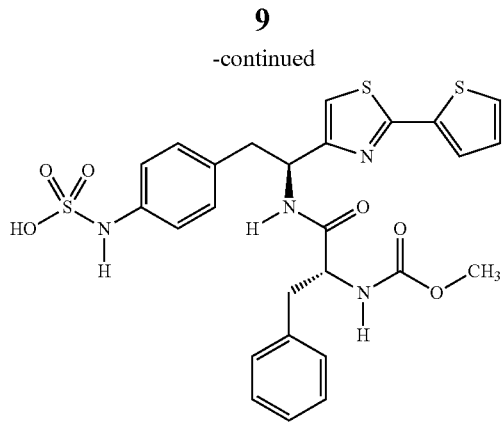

,

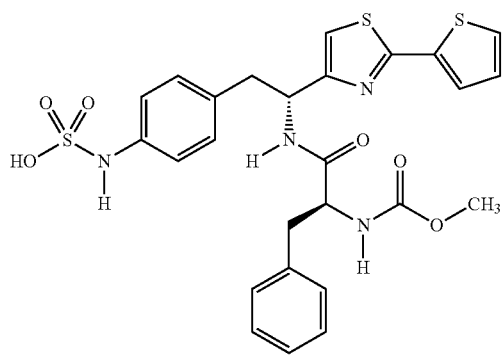

,

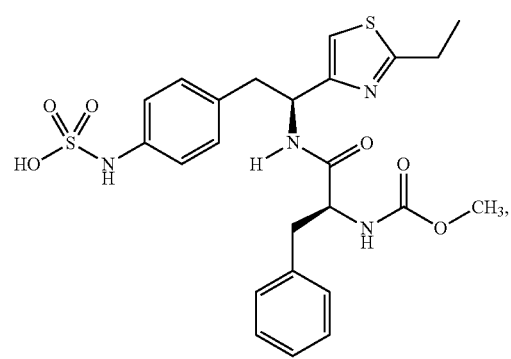

,

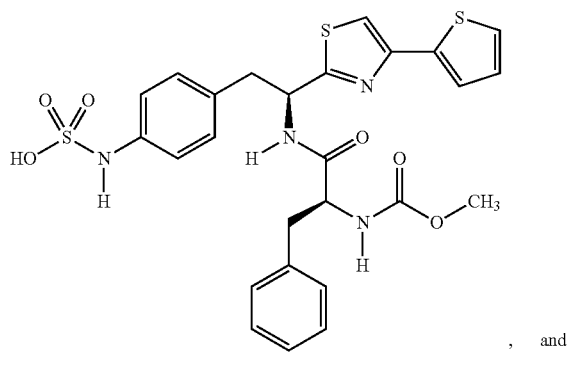

, and

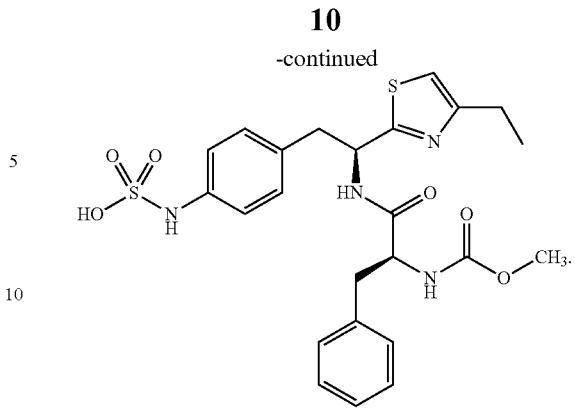

.

Optional Substituents for Chemical Groups.

Non-limiting examples of optional substituents include hydroxyl groups, sulfhydryl groups, halogens, amino groups, nitro groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, and ester groups.

Non-limiting examples of alkyl and alkylene groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Pharmaceutically-Acceptable Salts.

The present disclosure provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound described herein. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, piprazole, imidazole, or pyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a piprazole salt, an imidazole salt, or a pyrazine salt.

Acid addition salts can arise from the addition of an acid to a compound described herein. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

A compound herein can be a salt of an acidic group, for example:

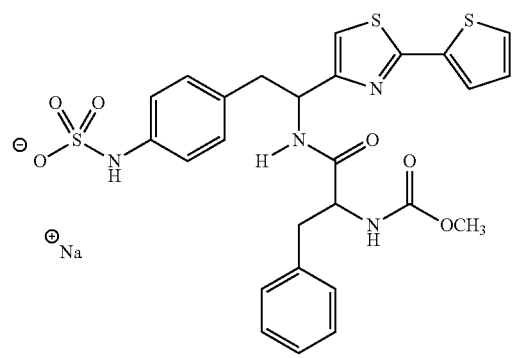

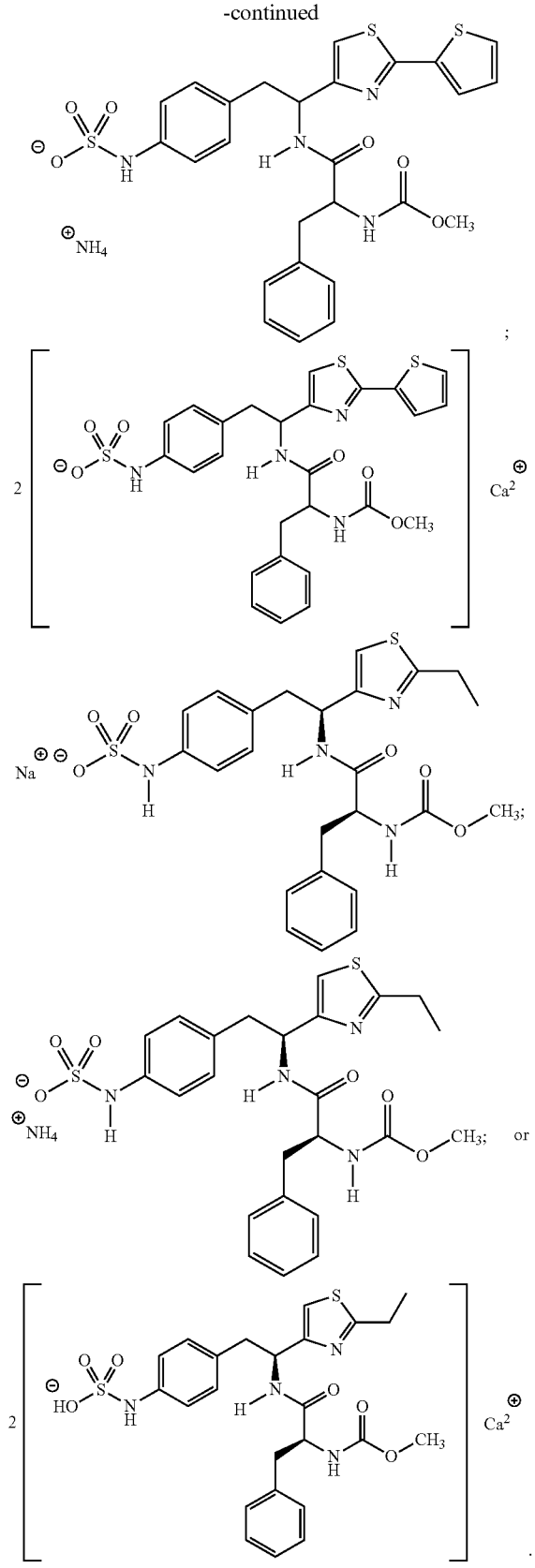
A compound herein can be a salt of a basic group formed from a strong acid, for example:
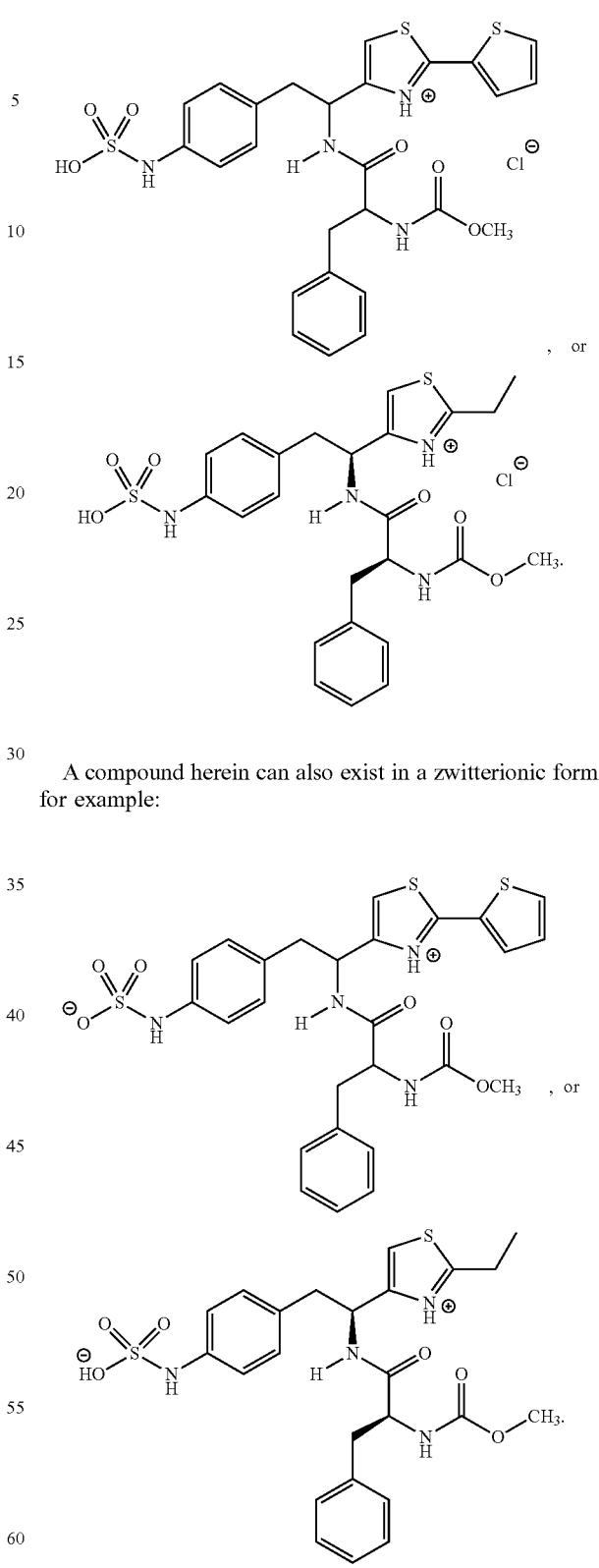
A compound herein can also exist in a zwitterionic form, for example:
Formulations.
A pharmaceutical composition of the disclosure can provide a therapeutically-effective amount of an activator of Tie-2.

The disclosed formulations can comprise one or more pharmaceutically-acceptable agents, which alone or in combination solubilize a compound herein or a pharmaceutically-acceptable salt thereof.

In some embodiments, a compound or pharmaceutically-acceptable salt thereof is present in a formulation in an amount of from about 0.1 mg/mL to about 100 mg/mL, from about 0.1 mg/mL to about 1 mg/mL, from about 0.1 mg/mL to about 5 mg/mL, from about 5 mg/mL to about 10 mg/mL, from about 10 mg/mL to about 15 mg/mL, from about 15 mg/mL to about 20 mg/mL, from about 20 mg/mL to about 25 mg/mL, from about 25 mg/mL to about 30 mg/mL, from about 30 mg/mL to about 35 mg/mL, from about 35 mg/mL to about 40 mg/mL, from about 40 mg/mL to about 45 mg/mL, about 45 mg/mL to about 50 mg/mL, from about 50 mg/mL to about 55 mg/mL, from about 55 mg/mL to about 60 mg/mL, from about 60 mg/mL to about 65 mg/mL, from about 65 mg/mL to about 70 mg/mL, from about 70 mg/mL to about 75 mg/mL, about 75 mg/mL to about 80 mg/mL, from about 80 mg/mL to about 85 mg/mL, from about 85 mg/mL to about 90 mg/mL, from about 90 mg/mL to about 95 mg/mL, or from about 95 mg/mL to about 100 mg/mL.

In some embodiments, a compound or pharmaceutically-acceptable salt thereof is present in a formulation in an amount of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL.

A formulation that is disclosed herein can be made more soluble by the addition of an additive or agent. The improvement of solubility of the formulation can increase by about 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

A formulation disclosed herein can be stable for about 1 day, about 2 days, about 3 days, about 4 days, about 5 days, about 6 days, about 7 days, about 8 days, about 9 days, about 10 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C.

Alcohols.

A non-limiting example of a solubilizing agent includes an organic solvent. Non-limiting examples of organic solvents include alcohols, for example, $C_1$-$C_4$ linear alkyl, $C_3$-$C_4$ branched alkyl, ethanol, ethylene glycol, glycerin, 2-hydroxypropanol, propylene glycol, maltitol, sorbitol, xylitol; substituted or unsubstituted aryl, and benzyl alcohol.

Cyclodextrins.

Non-limiting examples of cyclodextrins include β-cyclodextrin, methyl β-cyclodextrin, 2-hydroxypropyl-β-cyclodextrin (HPβCD), hydroxyethyl-β-cyclodextrin (HE-β-CD), heptakis (2,6-di-O-methyl)-β-cyclodextrin (DMβCD), α-cyclodextrin, γ-cyclodextrin, 2-hydroxypropyl-γ-cyclodextrin (HPγCD), and sulfobutylether-β-cyclodextrin (SBECD) sodium salt.

A cyclodextrin can possess a large cyclic structure with a channel passing through the center of the structure. The interior of the cyclodextrin can be hydrophobic, and interact favorably with hydrophobic molecules. The exterior of the cyclodextrin can be highly hydrophilic owing to the several hydroxyl groups exposed to bulk solvent. Capture of a hydrophobic molecule, such as a compound disclosed herein, in the channel of the cyclodextrin can result in the formation of a complex stabilized by non-covalent hydrophobic interactions. The complex can be soluble in water, and carry the captured hydrophobic molecule into the bulk solvent.

The disclosed solubilizing systems comprise 2-hydroxypropyl-beta-cyclodextrin (HPβCD). 2-Hydroxypropyl-β-cyclodextrin [CAS No. 128446-35-5] is commercially available as Cavitron™. 2-Hydroxypropyl-β-cyclodextrin, also described known as hydroxypropyl-β-cyclodextrin, 2-hydroxypropyl-beta-cyclodextrin, hydroxypropyl-beta-cyclodextrin or HPβCD, can be represented by either of the following formulae:

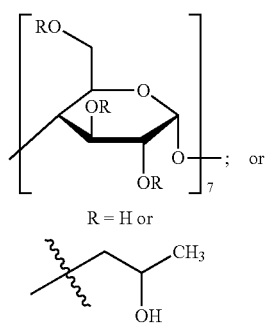

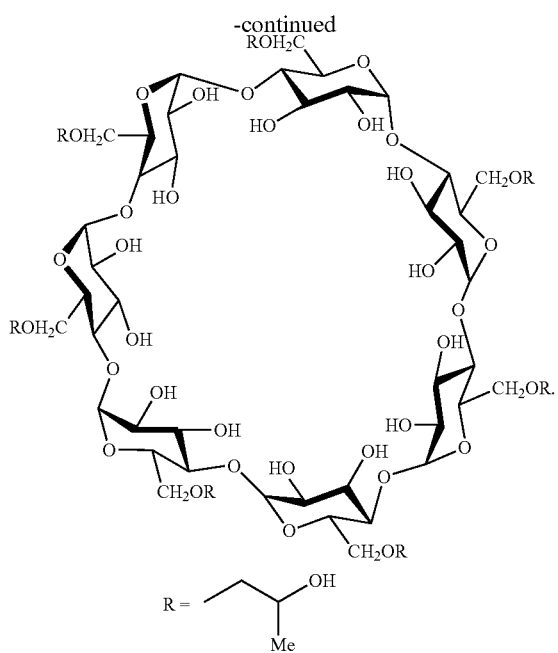

The average molecular weight of Cavitron™, is approximately 1396 Da, wherein the average degree of substitution is from about 0.5 to about 1.3 units of 2-hydroxypropyl per ring glucose unit.

In one embodiment, a formulation disclosed herein can comprise a ratio of about 20 parts of a compound herein or a pharmaceutically-acceptable salt thereof to about 1 part solubilizing system (about 20:about 1), to about 1 part of the compound herein or a pharmaceutically-acceptable salt thereof to about 20 parts solubilizing system (about 1:about 20). For example, a formulation containing about 100 mg of a compound herein or a pharmaceutically-acceptable salt thereof can contain from about 5 mg to about 2000 mg of a solubilizing agent, such as a cyclodextrin. In another embodiment, the ratio can be based on number, or moles, or compound compared to number, or moles, of the solubilizing system.

The following are non-limiting examples of ratios of a compound herein and a solubilizing agent, such as a cyclodextrin. The following examples alternatively describe the ratio of a solubilizing agent, such as a cyclodextrin, and a compound herein. The ratio can be: about 20:about 1; about 19.9:about 1; about 19.8:about 1; about 19.7:about 1; about 19.6:about 1; about 19.5:about 1; about 19.4:about 1; about 19.3:about 1; about 19.2:about 1; about 19.1:about 1; about 19:about 1; about 18.9:about 1; about 18.8:about 1; about 18.7:about 1; about 18.6:about 1; about 18.5:about 1; about 18.4:about 1; about 18.3:about 1; about 18.2:about 1; about 18.1:about 1; about 18:about 1; about 17.9:about 1; about 17.8:about 1; about 17.7:about 1; about 17.6:about 1; about 17.5:about 1; about 17.4:about 1; about 17.3:about 1; about 17.2:about 1; about 17.1:about 1; about 17:about 1; about 16.9:about 1; about 16.8:about 1; about 16.7:about 1; about 16.6:about 1; about 16.5:about 1; about 16.4:about 1; about 16.3:about 1; about 16.2:about 1; about 16.1:about 1; about 16:about 1; about 15.9:about 1; about 15.8:about 1; about 15.7:about 1; about 15.6:about 1; about 15.5:about 1; about 15.4:about 1; about 15.3:about 1; about 15.2:about 1; about 15.1:about 1; about 15:about 1; about 14.9:about 1; about 14.8:about 1; about 14.7:about 1; about 14.6:about 1; about 14.5:about 1; about 14.4:about 1; about 14.3:about 1; about 14.2:about 1; about 14.1:about 1; about 14:about 1; about 13.9:about 1; about 13.8:about 1; about 13.7:about 1; about 13.6:about 1; about 13.5:about 1; about 13.4:about 1; about 13.3:about 1; about 13.2:about 1; about 13.1:about 1; about 13:about 1; about 12.9:about 1; about 12.8:about 1; about 12.7:about 1; about 12.6:about 1; about 12.5:about 1; about 12.4:about 1; about 12.3:about 1; about 12.2:about 1; about 12.1:about 1; about 12:about 1; about 11.9:about 1; about 11.8:about 1; about 11.7:about 1; about 11.6:about 1; about 11.5:about 1; about 11.4:about 1; about 11.3:about 1; about 11.2:about 1; about 11.1:about 1; about 11:about 1; about 10.9:about 1; about 10.8:about 1; about 10.7:about 1; about 10.6:about 1; about 10.5:about 1; about 10.4:about 1; about 10.3:about 1; about 10.2:about 1; about 10.1:about 1; about 10:about 1; about 9.9:about 1; about 9.8:about 1; about 9.7:about 1; about 9.6:about 1; about 9.5:about 1; about 9.4:about 1; about 9.3:about 1; about 9.2:about 1; about 9.1:about 1; about 9:about 1; about 8.9:about 1; about 8.8:about 1; about 8.7:about 1; about 8.6:about 1; about 8.5:about 1; about 8.4:about 1; about 8.3:about 1; about 8.2:about 1; about 8.1:about 1; about 8:about 1; about 7.9:about 1; about 7.8:about 1; about 7.7:about 1; about 7.6:about 1; about 7.5:about 1; about 7.4:about 1; about 7.3:about 1; about 7.2:about 1; about 7.1:about 1; about 7:about 1; about 6.9:about 1; about 6.8:about 1; about 6.7:about 1; about 6.6:about 1; about 6.5:about 1; about 6.4:about 1; about 6.3:about 1; about 6.2:about 1; about 6.1:about 1; about 6:about 1; about 5.9:about 1; about 5.8:about 1; about 5.7:about 1; about 5.6:about 1; about 5.5:about 1; about 5.4:about 1; about 5.3:about 1; about 5.2:about 1; about 5.1:about 1; about 5:about 1; about 4.9:about 1; about 4.8:about 1; about 4.7:about 1; about 4.6:about 1; about 4.5:about 1; about 4.4:about 1; about 4.3:about 1; about 4.2:about 1; about 4.1:about 1; about 4:about 1; about 3.9:about 1; about 3.8:about 1; about 3.7:about 1; about 3.6:about 1; about 3.5:about 1; about 3.4:about 1; about 3.3:about 1; about 3.2:about 1; about 3.1:about 1; about 3:about 1; about 2.9:about 1; about 2.8:about 1; about 2.7:about 1; about 2.6:about 1; about 2.5:about 1; about 2.4:about 1; about 2.3:about 1; about 2.2:about 1; about 2.1:about 1; about 2:about 1; about 1.9:about 1; about 1.8:about 1; about 1.7:about 1; about 1.6:about 1; about 1.5:about 1; about 1.4:about 1; about 1.3:about 1; about 1.2:about 1; about 1.1:about 1; or about 1:about 1.

Polyvinylpyrrolidone.

Another non-limiting example of a solubilizing agent is polyvinylpyrrolidone (PVP), having the formula:

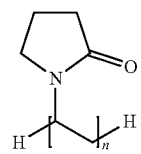

wherein the index n is from about 40 to about 200. PVP's can have an average molecular weight from about 5500 to about 28,000 g/mol. One non-limiting example is PVP-10, having an average molecular weight of approximately 10,000 g/mol.

Polyakyleneoxides and Ethers Thereof.

Another non-limiting example of solubilizing agents includes polyalkyleneoxides, and polymers of alcohols or polyols. Polymers can be mixed, or contain a single monomeric repeat subunit. For example, polyethylene glycols having an average molecular weight of from about 200 to about 20,000, for example, PEG 200, PEG 400, PEG 600, PEG 1000, PEG 1450, PEG 1500, PEG 4000, PEG 4600, and PEG 8000. In a same embodiment, a composition comprises one or more polyethylene glycols chosen from PEG 400, PEG 1000, PEG 1450, PEG 4600 and PEG 8000.

Other polyalkyleneoxides are polypropylene glycols having the formula:

$$HO[CH(CH_3)CH_2O]_xH$$

wherein the index x represents the average number of propyleneoxy units in the polymer. The index x can be represented by a whole number or a fraction. For example, a polypropylene glycol having an average molecular weight of 8,000 g/mole (PEG 8000) can be represented by the formulae:

$$HO[CH(CH_3)CH_2O]_{138}H \text{ or } HO[CH(CH_3)CH_2O]_{137.6}H$$

or the polypropylene glycol can be represented by the common, short hand notation: PEG 8000.

Another example of polypropylene glycols can have an average molecular weight from about 1200 g/mol to about 20,000 g/mol, i.e., a polypropylene glycol having an average molecular weight of about 8,000 g/mol, for example, PEG 8000.

Another solubilizing agent is Polysorbate 80 (Tween™ 80), which is an oleate ester of sorbitol and its anhydrides copolymerized with approximately 20 moles of ethylene oxide for each mole of sorbitol and sorbitol anhydrides. Polysorbate 80 is made up of sorbitan mono-9-octadecanoate poly(oxy-1,2-ethandiyl) derivatives.

Solubilizing agents also include poloxamers having the formula:

$$HO(CH_2CH_2)_{y1}(CH_2CH_2CH_2O)_{y2}(CH_2CH_2O)_{y3}OH$$

which are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol.

Excipients and Administration of a Pharmaceutical Composition.

A pharmaceutical composition described herein can be a combination of any pharmaceutical compounds described herein with other chemical components, such as carriers, stabilizers, diluents, dispersing agents, suspending agents, thickening agents, or excipients. The pharmaceutical composition facilitates administration of the compound to an organism. Pharmaceutical compositions can be administered in therapeutically-effective amounts as pharmaceutical compositions by various forms and routes including, for example, intravenous, intravitreal, subcutaneous, intramuscular, intraocular, oral, rectal, aerosol, parenteral, ophthalmic, pulmonary, transdermal, vaginal, otic, nasal, and topical administration.

A pharmaceutical composition can be administered in a local or systemic manner, for example, via injection of the compound directly into an organ, optionally in a depot or sustained release formulation, or via direct administration to the posterior or anterior portion of the eye of a subject. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients. Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum 23yrazi, talc, polyvinylpyrrolidone, carbopol gel, polyethylene glycol, or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically-acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

The formulation described herein can be administered as eye drops. The average volume of each drop administered to a subject can be about 5 µl, about 10 µl, about 15 µl, about 20 µl, about 30 µl, about 40 µl, about 50 µl, about 60 µl, about 70 µl, about 80 µl, about 90 µl, or about 100 µl. The eye drops can contain about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% of a compound disclosed herein. The drops can contain about 1 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 60 mg/ml, about 70 mg/ml, about 80 mg/ml, about 90 mg/ml, about 100 mg/ml, about 120 mg/ml, about 140 mg/ml, about 160 mg/ml, about 180 mg/ml, or about 200 mg/ml of a compound disclosed herein. The individual dose administered to a subject can be about 0.5 µg about 1 µg, about 2 µg, about 3 µg, about 4 µg, about 5 µg, about 6 µg, about 7 µg, about 8 µg about 9 µg, about 10 µg, about 20 µg, about 30 µg, about 40 µg, about 50 µg, about 60 µg, about 70 µg, about 80 µg, about 90 µg, about 100 µg about 150 µg about 200 µg, about 250 µg, about 300 µg, about 350 µg, about 400 µg, about 450 µg, about 500 µg, about 550 µg, about 600 µg, about 650 µg, about 700 µg, about 750 µg, about 800 µg, about 850 µg, about 900 µg, about 950 µg, about 1 mg, about 1.1 mg, about 1.2 mg, 1.3 mg, about 1.4 mg, about 1.5 mg, about 1.6 mg, about 1.7 mg, about 1.8 mg, about 1.9 mg, or about 2 mg of a compound disclosed herein. In some embodiments, more than one drop can be administered to an eye either at one time or at multiple times throughout the day.

Non-limiting examples of excipients suitable for use in eye drops include cyclodextrin, α-cyclodextrin, β-cyclodextrin, 2-hydroxypropyl-β-cyclodextrin (HP-β-CD), random methyl-β-cyclodextrin (RM-β-CD), sulfobutyl ether β-cyclodextrin (SBE-β-CD), γ-cyclodextrin, hydroxypropyl-γ-cyclodextrin (HP-γ-CD), hydroxyethyl-β-cyclodextrin (HE-β-CD), heptakis (2,6-di-O-methyl)-β-cyclodextrin (DMβCD), saline, sodium bisulfate, metabisulfate, ascorbic acid, acetylcysteine, benzalkonium chloride, boric acid, hyaluronic acid, hypromellose, propylene glycol, potassium sorbate, sodium chloride, sodium acetate, disodium edetate, sodium dihydrogen phosphate monohydrate, disodium phosphate, sodium hydroxide, hydrochloric acid, glycerol, mannitol, trometamol, tyloxapol, and any combination thereof.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compounds described herein can be manufactured, for example, by mixing, dissolving, granulating, dragee-making, levigating, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. The methods and pharmaceutical compositions described herein include the use of crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

A micelle of a pharmaceutical composition described herein can comprise a mucoadhesive block polymer, in which the micelle comprises a mucoadhesive component, a degradable component, and a micelle-forming component. The micelles can be used for delivery of cargo to a mucosal surface. A biocompatible mucoadhesive block copolymer micelle can comprise a degradable hydrophobic polymer, a degradable synthetic hydrophilic polymer, and a mucoadhesive component.

A pharmaceutical composition described herein can be formulated as a mucoadhesive-based ophthalmic drug delivery system comprising, for example, a poly(L-lactide)-b-poly(methacrylic acid-co-phenylboronic acid) copolymer micelle.

In some embodiments, a pharmaceutical composition described herein comprises a nanofibrous hydrogel network, a micelle, a mucoadhesive micelle, a shear-responsive ophthalmic hydrogel, or a thermoresponsive polymer scaffold.

Non-limiting examples of dosage forms suitable for use in a pharmaceutical composition described herein include feed, food, pellet, lozenge, liquid (e.g. a solution), elixir, aerosol, inhalant, spray, powder, tablet, pill, capsule, gel, geltab, nanosuspension, nanoparticle, microgel, nanogel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

A pharmaceutical formulation described herein can be administered as eye drops. The average volume of each drop administered to a subject can be about 5 µl, about 10 µl, about 15 about 20 about 30 about 40 about 50 about 60 about 70 about 80 about 90 or about 100 µl. The eye drops can contain about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% of a compound described herein. The drops can contain about 1 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 60 mg/ml, about 70 mg/ml, about 80 mg/ml, about 90 mg/ml, about 100 mg/ml, about 120 mg/ml, about 140 mg/ml, about 160 mg/ml, about 180 mg/ml, or about 200 mg/ml of a compound described herein. The individual dose administered to a subject can be about 0.5 µg, about 1 µg, about 2 µg, about 3 µg, about 4 µg, about 5 µg, about 6 µg, about 7 µg, about 8 µg, about 9 µg, about 10 µg, about 20 µg, about 30 µg, about 40 µg, about 50 µg, about 60 µg, about 70 µg, about 80 µg, about 90 µg, about 100 µg, about 150 µg, about 200 µg, about 250 µg, about 300 µg, about 350 µg, about 400 µg, about 450 µg, about 500 µg, about 550 µg, about 600 µg, about 650 µg, about 700 µg, about 750 µg, about 800 µg, about 850 µg, about 900 µg, about 950 µg, about 1 mg, about 1.1 mg, about 1.2 mg, 1.3 mg, about 1.4 mg, about 1.5 mg, about 1.6 mg, about 1.7 mg, about 1.8 mg, about 1.9 mg, or about 2 mg of a compound described herein. In some embodiments, more than one drop can be administered to an eye either at one time or at multiple times throughout the day.

Non-limiting examples of excipients suitable for use in eye drops or any other unit dosage form described herein include cyclodextrin, α-cyclodextrin, β-cyclodextrin, 2-hydroxypropyl-β-cyclodextrin (HP-β-CD), random methyl-β-cyclodextrin (RM-β-CD), sulfobutyl ether β-cyclodextrin (SBE-β-CD) sodium salt, γ-cyclodextrin, hydroxypropyl-γ-cyclodextrin (HP-γ-CD), hydroxyethyl-β-cyclodextrin (HE-β-CD), heptakis (2,6-di-O-methyl)-β-cyclodextrin (DMβCD), anthracene/PEG-Anthracene, saline, sodium bisulfate, metabisulfate, ascorbic acid, acetylcysteine, benzalkonium chloride, boric acid, hyaluronic acid, hypromellose, phenylboronic acid (pLA-b-p(MAA-PBA)), polyacrylic acid; poly(hydroxyethyl methacrylate) (pHEMA), polymethylmethacrylate, poly N-isopropyl acrylamide (NI-PAAm), polyurethane, polyurethane ureas, propylene glycol, cellulose, methyl cellulose, silicone elastomers, hydrophobically modified poly(vinyl pyrrolidone), potassium sorbate, sodium chloride, sodium acetate, disodium edetate, sodium dihydrogen phosphate monohydrate, disodium phosphate, sodium hydroxide, hydrochloric acid, glycerol, mannitol, tocophersolan (d-α-tocopherol polyethylene glycol succinate (TPGS); water-soluble Vitamin E, Vitamin E polyethylene glycol succinate), trometamol, tyloxapol, and any combination thereof.

In some embodiments, pharmaceutically-acceptable excipients include polymers. Polymers that are suitable as excipients for use in a unit dosage form described herein can comprise, a portion that is, for example, poly(N-tert-butylacrylamide), poly(oligoethylene glycol methacrylate), polylactide, polymethacrylic acid, or any combination thereof.

In some embodiments, a pharmaceutical composition of the disclosure can comprise an excipient that comprises a polymer and a monomer that comprises, for example a phenylboronic acid unit.

A copolymer is a polymer that is derived from multiple monomers. Non-limiting examples of monomers that can make up a copolymer described herein include an O-methacrylated vitamin E such as γ-tocopherol-O-methacrylate; or an ester of methacrylic acid and a polyethylene glycol moiety such as polyethylene glycol methyl ether methacrylate or polyethylene glycol ethyl ether methacrylate. In some embodiments, a pharmaceutical composition disclosed herein comprises a copolymer excipient. A copolymer excipient of the disclosure can contain two components. In some embodiments the two components of a copolymer are present in a ratio from 2:1 to 1:2.

A pharmaceutical composition described herein can comprise a population of polymers, a population of copolymers, or combinations thereof. In some embodiments, the molecules that make up a population of a copolymer have an average molecular weight of about 10 kDa, about 20 kDa, about 30 kDa, about 40 kDa, about 50 kDa, about 60 kDa, about 70 kDa, about 80 kDa, about 90 kDa, or about 100 kDa. In some embodiments, the molecules that make up a population of a polymer have an average molecular weight of about 10 kDa, about 20 kDa, about 30 kDa, about 40 kDa, about 50 kDa, about 60 kDa, about 70 kDa, about 80 kDa, about 90 kDa, or about 100 kDa.

In some embodiments, a pharmaceutical composition described herein comprises TPGS and PEG.

Non-limiting examples of pharmaceutically-acceptable excipients suitable for use in a composition described herein include granulating agents, binding agents, lubricating agents, disintegrating agents, in situ gelling agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, anti-microbial agents, plant cellulosic material and spheronization agents, and any combination thereof.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins1999), each of which is incorporated by reference in its entirety.

A composition described herein can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses. A hydrogel described herein can be modified by heparin dendrimers.

A pharmaceutical composition described herein can comprise a polymer system that can transition from a liquid to a gel at the active site. The transition from liquid to gel can happen, for example, upon exposure of the composition to heat or light. Suitable transition monomers include, for example, acrylic-based polymers such as polymethylmethacrylate, pHEMA, NIPAAm, and polyacrylic acid; polyurethanes and polyurethane ureas; silicone polymers; acrylic-based polymers such as pHEMA (which can comprise from about 1% to 99% TRIS); other hydrogel polymers including polyvinyl alcohol and protein-based biopolymers such as collagen; and polyethylene oxide (PEO)/N,N-dimethylacrylamide (DMA). The polymer system can also comprise a co-monomer component that is degradable over time. Non-limiting examples of degradable co-monomers include acryloyloxy dimethyl-γ-butyrolactone (DBA) and other lactone-containing materials such as poly(lactic acid), poly(glycolic acid), poly(glycolic-co-lactic acid), poly(caprolactone), poly(dioxanone), poly(3-hydroxybutyrate), poly(3-hydroxyvalcrate), poly(valcrolactone), poly(tartonic acid), poly(malonic acid), poly(anhydrides), poly(orthoesters), and polyphosphazenes.

A pharmaceutical composition described herein can be administered to a subject via intraocular or intravitreal administration to allow localized delivery of a therapeutic agent described herein. To allow for fewer intravitreal rejections, a biodegradable polymer system can be used for the in vivo delivery of a therapeutic agent described herein. In some embodiments, a pharmaceutical composition described herein comprises a polymer system, wherein the polymer system comprises a polymeric backbone, and wherein the polymer system is capable of reversible stimuli-induced phase transition from a liquid to a gel. In some embodiments, a method of delivering a therapeutic agent to a target site in vivo comprises administering an aqueous biocompatible polymer solution to the target site, wherein the polymer incorporates a therapeutic agent and a component that is degradable over time, and wherein the polymer system is capable of reversible stimuli-induced phase transition from liquid to gel.

The polymer system can be mixed with an initiating agent that is sensitive to a given stimulus, such as heat or light, to result in gelation of the solution. A photo-initiator can be added to the polymer system to impart photo-sensitivity to the polymer solution. Non-limiting examples of suitable photo-initiators include 2,2-dimethoxy-2-phenylacetophenone (DMPA), benzophenone, and IRGACURE™.

A wavelength of light that can be used to stimulate a pharmaceutical composition described herein can be, for example, about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, or about 700 nm.

A pharmaceutical composition described herein can also comprise a glycosaminoglycan, such as hyaluronic acid. A hyaluronic acid (HA)-retaining biopolymer can exhibit reduced levels of protein adsorption, surface friction, and increased lubricity, as compared with a biopolymer alone. A HA-retaining biopolymer can be used for incorporation into devices for use in protein-containing environments in which protein adsorption is undesirable and/or in environments where reduced surface friction is desirable, for example, in devices such as contact lenses.

A pharmaceutical composition described herein can be provided to a subject as a hydrogel. The hydrogel can be provided in situ in which a prepolymer is prepared, administered to a desired target site, such as, for example, an eye, and exposed to a stimulus that induces polymerization at the target site. The method of in situ hydrogel polymerization can comprise the steps of: 1) modifying a biocompatible backbone polymer with an in situ polymerizable group to form a prepolymer solution; 2) administering the prepolymer solution to a target site; and 3) exposing the prepolymer solution to a stimulus that induces polymerization of the solution at the target site. The prepolymer solution can comprise, for example, a collagen backbone and an acrylamide polymerizing agent.

A pharmaceutical composition described herein can be provided to a subject as a non-invasive system in which compound delivery can be photo-responsive and release of the compound can be controlled by exposure to different wavelengths of light. The photo-responsive delivery system can comprise a physiologically compatible crosslinked matrix, wherein said matrix is crosslinked with a photo-sensitive matrix crosslinker.

An injectable hydrogel described herein can comprise, for example, poly(ethylene glycol) (PEG) and a vitamin E methacrylate copolymer prepared via free radical polymerization and delivered in a solution of low molecular weight PEG and vitamin E as the solvent, instead of water. The hydrogel can form immediately in an aqueous environment with a controllable gelation time. The gelation occurs due to self-assembly of hydrophobic vitamin E residues upon exposure to water to form a physically cross-linked polymer network via polymer chain rearrangement and subsequent phase separation, a spontaneous process with water uptake.

The hydrogels can be customized to provide the desired water content, mechanical strength, and drug release kinetics by, for example, formulating the PEGMA-co-vitamin E polymer with an appropriate solvent mixture or by varying the molecular weight of the polymer.

A hydrogel described herein can further be formulated as a microparticle. A hydrogel microparticle described herein can comprise, for example, alginate and cationically modified alginate microparticles, to provide a controlled release of a therapeutic agent.

The disclosed compositions can optionally comprise from about 0.001% to about 0.005% weight by volume pharmaceutically-acceptable preservatives. One non-limiting example of a suitable preservative is benzyl alcohol.

In some embodiments, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

The disclosed methods include administration of a Tie-2 activator, or a pharmaceutically-acceptable salt thereof, in combination with a pharmaceutically-acceptable carrier. The carrier can be selected to minimize any degradation of the active ingredient and to minimize any adverse side effects in the subject.

The Tie-2 activator or a pharmaceutically-acceptable salt thereof herein can be conveniently formulated into pharmaceutical compositions composed of one or more pharmaceutically-acceptable carriers. See e.g., Remington's Pharmaceutical Sciences, latest edition, by E.W. Martin Mack Pub. Co., Easton, Pa., which discloses typical carriers and conventional methods of preparing pharmaceutical compositions that can be used in conjunction with the preparation of formulations of the compound described herein and which is incorporated by reference herein. Such pharmaceuticals can be standard carriers for administration of compositions to humans and non-humans, including solutions such as sterile water, saline, and buffered solutions at physiological pH. Other compositions can be administered according to standard procedures. For example, pharmaceutical compositions can also include one or more additional active ingredients such as antimicrobial agents, anti-inflammatory agents, and anesthetics.

Non-limiting examples of pharmaceutically-acceptable carriers include saline solution, Ringer's solution and dextrose solution. The pH of the solution can be from about 5 to about 8, and can be from about 7 to about 7.5. Further carriers include sustained release preparations such as semipermeable matrices of solid hydrophobic polymers containing the Tie-2 activator or a pharmaceutically-acceptable salt thereof, where the matrices are in the form of shaped articles, such as films, liposomes, microparticles, and microcapsules.

The disclosed methods relate to administering the Tie-2 activator or a pharmaceutically-acceptable salt thereof as part of a pharmaceutical composition. In various embodiments, compositions described herein can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In some embodiments, the composition is an in situ gellable aqueous solution.

Pharmaceutical formulations can include additional carriers, as well as thickeners, diluents, buffers, preservatives, and surface active agents in addition to the compounds disclosed herein. Pharmaceutical formulations can also include one or more additional active ingredients such as antimicrobial agents, anti-inflammatory agents, anesthetics, and the like.

An excipient can fill a role as simple and direct as being an inert filler, or an excipient as used herein can be part of a pH stabilizing system or coating to insure delivery of the ingredients safely to the stomach.

The Tie-2 activator or a pharmaceutically-acceptable salt thereof can also be present in liquids, emulsions, or suspensions for delivery of active therapeutic agents in aerosol form to cavities of the body such as the nose, throat, or bronchial passages. The ratio of Tie-2 activator or a pharmaceutically-acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, for example, in unit dosage form suitable for single administration of a precise dosage. The compositions can contain, as noted above, an effective amount of the Tie-2 activator or a pharmaceutically-acceptable salt thereof in combination with a pharmaceutically-acceptable carrier and, in addition, can include other medicinal agents, pharmaceutical agents, carriers, adjuvants, diluents, etc.

For solid compositions, nontoxic solid carriers include, for example, pharmaceutical grades of mannitol, lactose, starch, magnesium stearate, sodium saccharin, talc, cellulose, methyl cellulose, glucose, sucrose, and magnesium carbonate. In one embodiment, a composition comprising the Tie-2 activator or a pharmaceutically-acceptable salt thereof in an amount of approximately 4 mg per 0.1 mL liquid is prepared. The liquid phase comprises sterile water and an appropriate amount of a saccharide or polysaccharide.

Release Kinetics and Burst Release.

Drug release is the process by which a drug becomes subject to adsorption, distribution, metabolism, and excretion. A model of drug release includes the zero order release model, in which the rate of release is independent of the drug concentration in the unit dosage form, and the drug release rate is constant over time. Zero order release can be observed in, for example, drugs formulated as transdermal patches, implantable depots, oral controlled release, matrix tablets with low solubility drugs, or as a suspension.

First order release kinetics occurs when the drug release rate is dependent upon the concentration of the drug in the unit dosage form.

Burst release can occur when, for example, a controlled release formulation is placed in a release medium, and an initial large bolus of drug is released before the release rate reaches a stable level. Burst release can lead to higher initial drug delivery, but also reduce the effective lifetime of the drug. Burst release can be favorable in situations such as, localized wound treatment, targeted delivery, or pulsatile release of a drug; however, burst release can be unfavorable due to local or systemic toxicity, shortened half-life of a drug, and a shortened release profile, which can require more frequent dosing of the drug.

In some embodiments, a pharmaceutical composition described herein can reduce the likelihood of burst release of a therapeutic agent described herein upon administration of the pharmaceutical composition to a subject. The reduction in burst release of a therapeutic agent described herein can allow for sustained release of the therapeutic agent. In some embodiments, a pharmaceutical composition described herein releases a therapeutic agent of the disclosure without an initial burst of the therapeutic agent. In some embodiments, a pharmaceutical composition described herein exhibits zero-order release kinetics.

A pharmaceutical composition described herein can release a therapeutic agent such as a Tie-2 activator over a prolonged period of time. In some embodiments, a pharmaceutical composition described herein release a therapeutic agent over a period of about 1 month to about 12 months. In some embodiments, a pharmaceutical composition described herein release a therapeutic agent over a period of about 1 month to about 2 months, about 1 month to about 3 months, about 1 month to about 4 months, about 1 month to about 5 months, about 1 month to about 6 months, about 1 month to about 12 months, about 2 months to about 3 months, about 2 months to about 4 months, about 2 months to about 5 months, about 2 months to about 6 months, about 2 months to about 12 months, about 3 months to about 4 months, about 3 months to about 5 months, about 3 months to about 6 months, about 3 months to about 12 months, about 4 months to about 5 months, about 4 months to about 6 months, about 4 months to about 12 months, about 5 months to about 6 months, about 5 months to about 12 months, or about 6 months to about 12 months. In some embodiments, a pharmaceutical composition described herein release a therapeutic agent over a period of about 1 month, about 2 months, about 3 months, about 4 months, about 5 months, about 6 months, or about 12 months. In some embodiments, a pharmaceutical composition described herein release a therapeutic agent over a period of at least about 1 month, at least about 2 months, at least about 3 months, at least about 4 months, at least about 5 months, or at least about 6 months. In some embodiments, a pharmaceutical composition described herein release a therapeutic agent over a period of at most at most about 2 months, at most about 3 months, at most about 4 months, at most about 5 months, at most about 6 months, or at most about 12 months.

Pharmaceutical Compositions.

Pharmaceutical compositions containing the compounds described herein can be administered for prophylactic or therapeutic treatments. Compositions can contain any number of active agents. In therapeutic applications, the compositions can be administered to a subject already suffering from a disease or condition, in an amount sufficient to cure or at least partially arrest the symptoms of the disease or condition, or to cure, heal, improve, reduce, lessen or ameliorate the disease or condition. Compounds can also be administered to lessen or reduce a likelihood of developing, contracting, or worsening a condition. Amounts effective for this use can vary based on the severity and course of the disease or condition, previous therapy, the subject's health status, weight, response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills or injections. The compounds can be packed together or separately, in a single package or in a plurality of packages. One or all of the therapeutic agents can be given in multiple doses. If not simultaneous, the timing between the multiple doses can vary.

Compounds and compositions described herein can be packaged as a kit. In some embodiments, the present disclosure provides a kit comprising a compound disclosed herein, or a pharmaceutically-acceptable salt thereof, and written instructions on use of the kit in the treatment of a condition described herein. In some embodiments, the present disclosure provides a kit comprising a compound disclosed herein, or a pharmaceutically-acceptable salt thereof, an antibody, and written instructions on use of the kit in the treatment of a condition described herein.

The compounds described herein can be administered before, during, or after the occurrence of a disease or condition, and the timing of administering the composition containing a compound can vary. For example, the compounds can be used as a prophylactic and can be administered continuously to subjects with a propensity to conditions or diseases in order to lessen or reduce a likelihood of the occurrence of the disease or condition. The compounds and compositions can be administered to a subject during or as soon as possible after the onset of the symptoms. The administration of the compounds can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

A pharmaceutical composition described herein can be administered to a subject twice a day, once a day, once every three days, once a week, twice a month, once every month, once every two months, once every three months, once every four months, once every five months, once every six months, once every seven months, once every eight months, once every nine months, once every ten months, once every eleven months, or once every year. In some embodiments a pharmaceutical composition described herein can be administered to a subject no more than twice a day, no more than once a day, no more than once every three days, no more than once a week, no more than twice a month, no more than once every month, no more than once every two months, no more than once every three months, no more than once every four months, no more than once every five months, no more than once every six months, no more than once every seven months, no more than once every eight months, no more than once every nine months, no more than once every ten months, no more than once every eleven months, or no more than once every year.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for parenteral injection can be presented in unit dosage form, for example, in ampoules, or in multi-dose containers with a preservative.

A Tie-2 activator described herein can be present in a composition in a range of from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg, from about 95 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, or from about 250 mg to about 300 mg.

A Tie-2 activator described herein can be present in a composition in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, or about 300 mg.

In some embodiments, a described herein can be used singly or in combination with one or more therapeutic agents as components of mixtures. For example, a compound disclosed herein can be co-formulated or co-administered with for example, an anti-VEGF agent or MAN-01. An anti-VEGF agent can be a compound, an antibody, or an antibody fragment, variant, or derivative thereof. Non-limiting examples of an anti-VEGF agent include bevacizumab (Avastin®), ranibizumab (Lucentis®), and aflibercept (Eylea®).

Methods Used Herein.
Chemical Analysis Methods.

The chemical structure of a composition disclosed herein can be analyzed by methods including, for example, nuclear magnetic resonance (NMR) spectroscopy. NMR spectroscopy is a spectroscopic technique in which a sample is placed in a magnetic field to observe the local magnetic fields around atomic nuclei. Radio waves excite the nuclei sample into NMR and the NMR signal is detected with radio receivers. The NMR signal results from magnetic properties of that are specific to particular atomic nuclei, thus the NMR signal provides details on the electronic structure of a molecule and individual functional groups of the molecule. The information gained from NMR spectroscopy can allow for the identification of monomolecular compounds, proteins, and other complex molecules. NMR spectroscopy can also provide detailed information on the structure, dynamics, reaction state, and chemical environment of molecules. Two types of NMR spectroscopy are proton NMR ($^1$H NMR) and carbon-13 NMR. In $^1$H NMR, NMR is applied with respect to hydrogen-1 nuclei, while in carbon-13 NMR, NMR is applied to carbon nuclei to allow identification of carbon atoms in an organic molecule.

The chemical structure of a composition disclosed herein can also be analyzed by Fourier transform infrared (FT-IR) spectroscopy. FT-IR spectroscopy is a non-destructive method that is based on the absorption of infrared radiation by the material being analyzed. Infrared radiation is focused on a sample, and a spectrometer is used to assess the amount of light absorbed by the sample at various wavelengths. A Fourier transform is used to convert data that is collected in the time domain into frequency domain spectra based on the absorbance and wavelength data. The absorption peaks detected in FT-IR spectroscopy arise from molecular vibrations and depend on molecular stretching, vibration, and rotation of chemical bounds, allowing FT-IR spectroscopy to provide information on a molecule's chemical structure.

Gel permeation chromatography is an experimental method that can be used to determine the molecular weight (MW) of a composition disclosed herein. Gel permeation chromatography is a type of size exclusion chromatography that separates analytes based on size or hydrodynamic volume. Samples are passed through a column packed with porous beads causing smaller analytes to move through the column faster than larger analytes. When used with comparable standards, the relative data obtained from gel permeation chromatography can be used to determine the molecular weight of molecules such as, for example, polymers.

In some embodiments, a composition disclosed herein is used to package one or more compounds and then release the one or more compounds into the surrounding environment. The amount of a compound released from a composition disclosed herein can be determined by, for example, high performance liquid chromatography (HPLC). HPLC is an analytical chemistry technique that can separate, identify, and quantify the components of a mixture. HPLC uses pumps to pass liquid solvents through chromatography columns filled with adsorbent resin causing each component of the mixture to interact with the resin. Each component will interact with the resin in a different manner causing the separation of components as they flow through the column. After flowing through the column the components are detected via a detector. Non-limiting examples of detectors that can be used for HPLC include ultraviolet-visible spectrometers (UV/Vis), photodiode arrays, or mass spectrometers. Detectors generate a signal that is proportional to the amount of sample that passes through the column. Thus, by using standards, mixture components can be identified and quantified based on retention time and the detected signal.

Differential Scanning Calorimetry.

The material properties of a composition disclosed herein can be assessed via techniques including, for example, differential scanning calorimetry (DSC). In DSC, the difference in the amount of heat required to increase the temperature of a sample and a reference is measured as a function of temperature. DSC data can be used to assess properties of a material including, for example, a material's glass transition temperature or low critical solution temperature. The glass transition temperature of a composition is the temperature at which the composition (i.e. a polymer) transitions from a hard, brittle, glass-like state to a viscous or rubber-like state. The low critical solution temperature of a mixture is the critical temperature below which the components of the mixture are miscible for all compositions.

Microscopy Methods.

The structural and morphological characteristics of a composition disclosed herein can be characterized via microscopy methods including, for example, atomic force microscopy, transmission electron microscopy, and scanning electron microscopy.

Atomic force microscopy (AFM) is a type of scanning probe microscopy that can achieve resolutions that are 1000 times finer than the optical diffraction limit. AFM can provide information on the surface of a structure by contacting the surface of the structure with a mechanical probe. The movements of the mechanical probe are facilitated by piezoelectric elements allowing for high accuracy and precision. The AFM probe contacts the surface and is moved along the surface in a precise rectangular pattern. The height of the probe is recorded at each position on the surface, allowing the surface topography to be determined at high resolution.

In transmission electron microscopy, a beam of electrons is transmitted through a specimen that has been cut into thin sections. The interactions of the electrons with the sample as they are transmitted through the sample allows for imaging at resolutions of about 0.2 nanometers due to the small de Broglie wavelengths of electrons.

In scanning electron microscopy, the surface of a sample is scanned with a focused beam of electrons in a rectangular pattern. Excitation of the electron beam causes atoms in the sample to emit secondary electrons that can be detected. The secondary electrons emitted by a sample depend on characteristics such as the topography of the sample. In conventional scanning electron microscopy, samples are observed in high vacuum. Using variable pressure or environmental scanning electron microscopy, specimens can be observed in low vacuum or wet conditions. Via the use of specialized instruments, specimens can also be observed at cryogenic or elevated temperatures.

Cell Viability.

The effect of a composition disclosed herein on cell viability can be assessed using various biochemical assays including, for example, calcein AM (CalAM) staining, ethidium homodimer-1 (EthD-1) staining, Trypan blue assays, and 3-(4,5-dimethylthiazol-2-yl)-2,5-diphenyltetrazolium (MTT) assays. EthD-1 and Trypan blue are impermeable to live cells, and are thus useful for imaging of dead cells that have compromised cell membranes. CalAM is a cell permeant dye that is converted from a non-fluorescent dye to a green fluorescent dye in live cells and is thus useful for the detection of live cells. MTT is reduced in live cells causing a color change and allowing for the colorimetric assessment of metabolic activity, which reflects the number of viable cells.

Nanoparticle Characterization.

The size of particles comprising a composition disclosed herein can be determined by, for example, nanoparticle tracking analysis. In nanoparticle tracking analysis, nanoparticle size is determined by relating size to Brownian motion. Nanoparticles contained in a sample are visualized via light scattering and the motion of individual particles is tracked frame by frame. The rate of particle movement can be related to a sphere-equivalent hydrodynamic radius as calculated through the Stokes-Einstein equation, allowing for the nanoparticle size distribution of a solution to be determined.

The stability of dispersions of particles comprising a composition disclosed herein can be assessed by, for example, zeta potential measurements. Zeta potential is the electrokinetic potential of a colloidal dispersion. The magnitude of zeta potential indicates the degree of electrostatic repulsion between adjacent, similarly charged particles in dispersion. Thus, a high magnitude zeta potential confers stability for nanoparticles because the repulsive forces will resist aggregation.

The mucoadhesion of particles comprising a composition disclosed herein can be assessed by methods including, for example, surface plasmon resonance measurements. Surface plasmon resonance is the resonant oscillation of conduction electrons at the interface between negative and positive permittivity materials stimulated by incident light. Surface plasmon reflectivity measurements can be used to detect adsorption, as the angle of minimum reflection will change when adsorption occurs. Nanoparticles including, for example, gold nanoparticles, exhibit enhanced surface plasmon resonance. Thus, to detect mucoadhesion, gold nanoparticles can be coated with proteins and then exposed to the particles of interest before surface plasmon resonance measurements are taken.

Animal Models.

One non-limiting example of an animal model for studying ocular disorders is the benzalkonium chloride (BAC)-induced dry eye disease model (DED). In this model, treatment of rats with 0.2% BAC into the eye for 7 days mimics DED by decreasing tear flows and corneal epithelial thickness, and increasing tear film osmolarity and damaged corneal tissue. Fluorescein staining is used to assess damage to corneal tissue compared to untreated control eyes. The Draize test can also be used to assess disease severity. To perform the Draize test, animal eyes are monitored for redness, swelling, discharge, ulceration, hemorrhaging, cloudiness, and blindness after disease induction.

Cell Types Used in Experiments Disclosed Herein.

To study the biological effect of a composition disclosed herein, various cell culture models can be used. Non-limiting examples of cell types that can be used are MP38, MP41, MP46, and M65 cells (human uveal, eye melanoma cells), WERI-Rb-1 and Y79 cells (human retinal retinoblastoma cells), ARPE-19 and ARPE-19/HPV-16 cells (human retinal epithelial cells), HCE-2 cells (human corneal epithelial cells), and B-3 cells (human lens epithelial cells).

Treatment of Subjects with a Tie-2 Activator.

The present disclosure provides methods for treating a subject having an ocular disease with an activator of Tie-2. The subject can be a human. Treatment can include treating a human in a clinical trial. A treatment can comprise administering to a subject a pharmaceutical composition comprising one or more of the activators of Tie-2 described throughout the disclosure. A treatment can comprise administrating to a subject a therapy that promotes the phosphorylation of a Tie-2 molecule.

In some embodiments, the present disclosure provides a Tie-2 activator for use in treatment of elevated intraocular pressure, ocular hypertension, neovascular glaucoma, primary open angle glaucoma, congenital glaucoma, or glaucoma. In some embodiments, the present disclosure provides a Tie-2 activator for use in the manufacture of a medicament for the treatment of elevated intraocular pressure, ocular hypertension, or glaucoma.

In some embodiments, the intraocular pressure or ocular hypertension is caused by a glaucoma. In some embodiments, the glaucoma is primary open angle glaucoma. In some embodiments, the glaucoma is open angle glaucoma.

Non-limiting examples of ocular conditions that can be treated by a compound disclosed herein include an ocular abrasion, age-related macular degeneration (wet form), blindness, branch retinal vein occlusion (BRVO), cataracts, choroidal neovascularization, congenital glaucoma, cystoid macular edema, dendritic ulcer, diabetic macular edema, diabetes-related blindness, diabetic retinopathy, dry eye disease, endophthalmitis, glaucoma, hemispheric retinal vein occlusion (HRVO), reduced aqueous humor drainage, reduced aqueous humor drainage downstream of Schlemm's canal, reduced lymphatic drainage in corneal limbal lymphatic system, reduced lymphatic drainage of Schlemm's canal, reduced aqueous humor drainage, reduced lymphatic drainage in corneal limbal lymphatic system, decreased lymphatic drainage of Schlemm's canal, increased intraocular pressure in the eye, keratoconus, macular degeneration, macular dystrophy, neovascularization in the eye, non-proliferative diabetic retinopathy, nystagmus, ocular hypoperfusion, ocular inflammation, ocular neuropathy, ocular ischemia, ocular trauma, orbital pain, pathologic neovascularization, proliferative diabetic retinopathy, retinal detachment, retinal vein occlusion (central or branch), retinal venous drainage occlusion, retinitis pigmentosa, retinoblastoma, scarring, surgery induced edema, surgery induced neovascularization, uveal melanoma, uveitis, vision loss, and vitreous hemorrhage.

In some embodiments, a compound disclosed herein can reduce intraocular pressure, increase aqueous humor drainage, increase aqueous humor drainage downstream of Schlemm's canal, increase lymphatic drainage in the corneal limbal lymphatic system, increase lymphatic drainage of Schlemm's canal, or suppress pressure-related loss of retinal ganglion cells.

Elevated intraocular pressure can be caused by inadequate aqueous humor outflow, which is limited by the flow capacity and resistance of Schlemm's canal. For example, morphological changes of Schlemm's canal, leading to increased resistance at the inner wall and reductions in Schlemm's canal area, can affect outflow capacity. Aqueous humor flows through the trabecular meshwork, into Schlemm's canal, and then through collector channels and aqueous veins that drain into the episcleral veins. Thus, inadequate aqueous humor outflow and elevated intraocular pressure are also related to the elevated episcleral venous pressure (EVP).

A compound disclosed herein can cause vasodilation of draining vessels downstream of Schlemm's canal, such as superficial vascular plexus (SVP). In this manner, the compound provides neuroprotection of neuronal cells in the eye, such as retinal ganglion cells. In some embodiments, a compound disclosed herein activates Tie-2 in or around the limbal vascular plexus, SVP, superficial capillary plexus (SCP), or episcleral veins. In some embodiments, a compound disclosed herein inhibits HPTPβ in or around the limbal vascular plexus, SVP, SCP, or episcleral veins. In some embodiments, a Tie-2 activator disclosed herein causes vasorelaxation of smooth muscle cells in or around the limbal vascular plexus, SVP, SCP, or episcleral veins. Vasorelaxation of the smooth muscle cells allows for vasodilation and enhanced aqueous humor outflow in the eye.

Non-limiting examples of vasorelaxants or vasodilators include alpha-adrenoceptor antagonists (alpha-blockers), angiotensin converting enzyme (ACE) inhibitors, angiotensin receptor blockers (ARBs), beta2-adrenoceptor agonists (β2-agonists), calcium-channel blockers (CCBs), centrally acting sympatholytics, direct acting vasodilators, endothelin receptor antagonists, ganglionic blockers, nitrodilators, phosphodiesterase inhibitors, potassium-channel openers, and renin inhibitors.

In some embodiments, a Tie-2 activator disclosed herein provides neuroprotection of neuronal cells, for example, retinal ganglion cells, from damage due to elevated intraocular pressure. Thus, the Tie-2 activator can reduce the likelihood of neuronal cell damage resulting from glaucoma symptoms. The Tie-2 activator can provide neuroprotection in absence of morphological changes to Schlemm's canal, for example, without changing the area or diameter of Schlemm's canal. In some embodiments, a compound disclosed herein can reduce the likelihood of morphological defects in Schlemm's canal, for example, defects resulting from elevated intraocular pressure.

Non-limiting examples of conditions that can be treated by a compound disclosed herein include acute kidney injury, an allergy, brain edema, neuroprotection, cancer, chronic kidney disease, cystic kidney disease, diabetic nephropathy, edema, glomerulonephritis, hypertension, infection, inflammation, influenza, lupus, lymphoma, myocardial ischemia, nephropathy, polycystic kidney disease, vascular leak, and vitamin A deficiency.

Non-limiting examples of possible subjects for administration include the following. Subjects can be humans, non-human primates such as chimpanzees, and other apes and monkey species; farm animals such as cattle, horses, sheep, goats, and swine; domestic animals such as rabbits, dogs, and cats; and laboratory animals including rats, mice, and guinea pigs. A subject can be of any age. Subjects can be, for example, elderly adults, adults, adolescents, pre-adolescents, children, toddlers, and infants.

Some conditions can lead to an increase in the levels of Ang-2, altering the ratio of Ang-1/Ang-2 in circulation. In some aspects, a therapy can improve the outcome of a disease state, including increased intraocular pressure or glaucoma, by altering the ratio of Ang-1/Ang-2 in circulation. A therapy can provide an Ang-1/Ang-2 ratio or an Ang-2/Ang-1 ratio of about 1:about 1, about 2:about 1, about 3:about 1, about 4:about 1, about 5:about 1, about 6:about 1, about 7:about 1, about 8:about 1, about 9:about 1, or about 10:about 1.

Compound 1

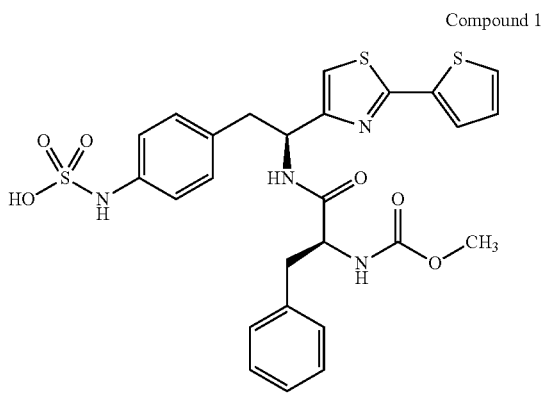 [SMILES: COC(=O)N[C@@H](Cc1ccccc1)C(=O)N[C@@H](Cc1ccc(NS(=O)(=O)O)cc1)c1csc(-c2cccs2)n1]

Treatment of Intraocular Pressure with a Tie-2 Activator.

FIG. 1 shows the effect of administration of a Tie-2 activator (Compound 1) delivered twice daily (BID) at varying doses on intraocular pressure (TOP) relative to a pre-treatment baseline. The difference in IOP was determined at the end of the trial, which was 28 days after treatment began (28 Day EOT). Changes in IOP were determined both in the study eye and the fellow eye. Doses greater than 15 mg BID of Compound 1 resulted in decreased IOP in patients with diabetic macular edema.

Figure 2:
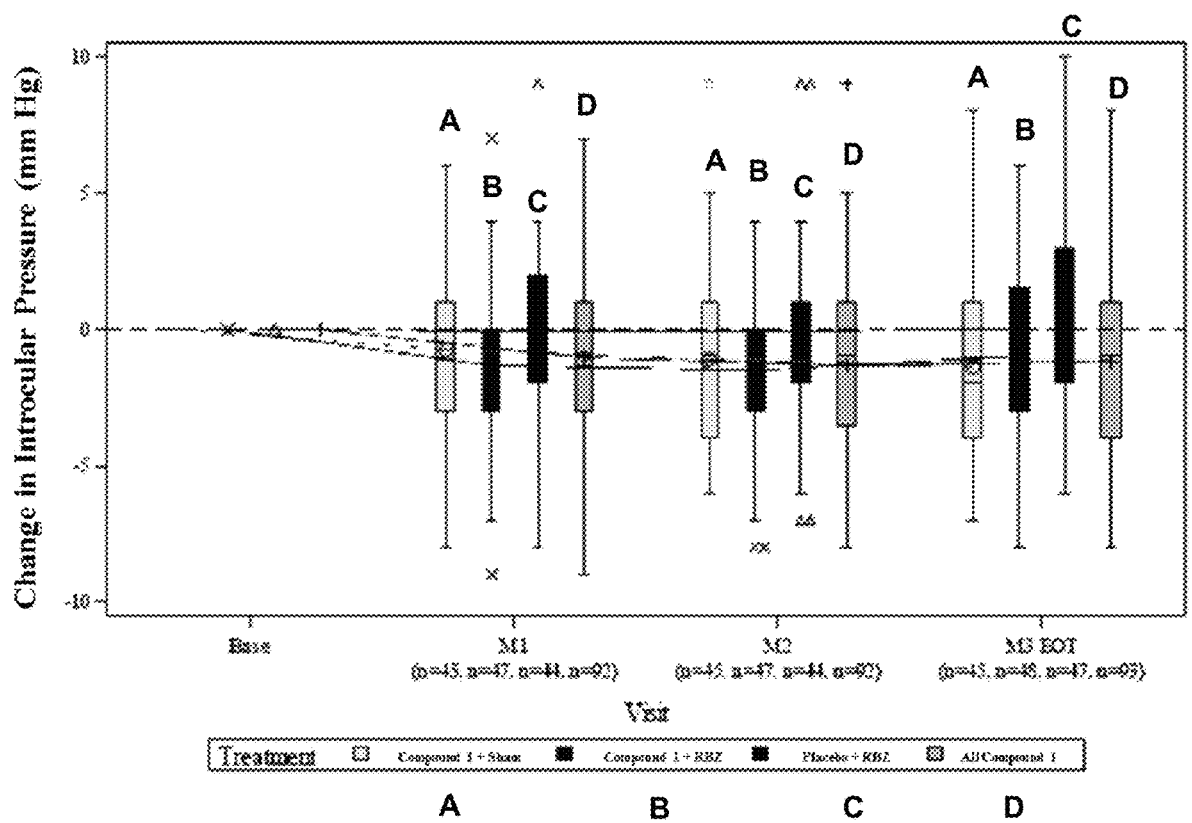
FIG. 2 illustrates changes in intraocular pressure from baseline. A: Compound 1+Sham; B: Compound 1+RBZ; C: Placebo+RBA; D: All Compound 1.

FIG. 2 shows the effect on intraocular pressure of administration of a Tie-2 activator (Compound 1) combined with a sham treatment; Compound 1 combined with ranibizumab (RBZ); a placebo combined with RBZ; or the combined results of both Compound 1 treatment groups. The difference in IOP was determined relative to a pre-treatment baseline (Base) at months 1, 2, and 3 (M1-M3). Intraocular pressure was determined in the study eye in millimeters of mercury (mmHg).

TABLE 1 shows the effect of shows the effect on intraocular pressure of administration of: 1) Compound 1 combined with a sham treatment (Compound 1+sham); 2) Compound 1 combined with ranibizumab (Compound 1+RBZ); or 3) a placebo combined with RBZ (placebo+RBZ). The difference in IOP was determined relative to a pre-treatment Baseline at Months 1, 2, and 3. Intraocular pressure was determined in the study eye/fellow eye in mmHg.

TABLE 1

| IOP/ Treatment arm | Compound 1 + sham | Compound 1 + RBZ | placebo + RBZ |
| --- | --- | --- | --- |
| Baseline | 15.8/15.4 | 15.9/16.1 | 15.2/15.8 |
| Month 1 | 14.8/14.5 | 14.7/14.4 | 15.0/15.5 |
| Month 2 | 14.4/14.3 | 14.6/14.7 | 15.0/15.5 |
| Month 3 | 14.3/14.0 | 15.1/14.7 | 15.3/15.7 |

EXAMPLES

Example 1. Compounds with Inhibitory Activity to HPTPβ

Non-limiting examples of the HPTPβ $IC_{50}$ (μM) activity for illustrative compounds are listed in TABLE 2.

TABLE 2

| No. | Compound | HPTPβ $IC_{50}$ μM |
| --- | --- | --- |
| AA1 | (S)-{4-[2-(4-Ethylthiazol-2-yl)-2-(phenylacetylamino)ethyl]-phenyl}sulfamic acid | 0.000157 |
| AA2 | 4-{(S)-2-[(R)-2-(tert-butoxycarbonylamino)-3-phenylpropanamido]-2-(4-ethylthiazol-2-yl)ethyl}phenylsulfamic acid | 0.004 |

TABLE 2-continued

| No. | Compound | HPTPβ IC$_{50}$ μM |
|---|---|---|
| AA3 | 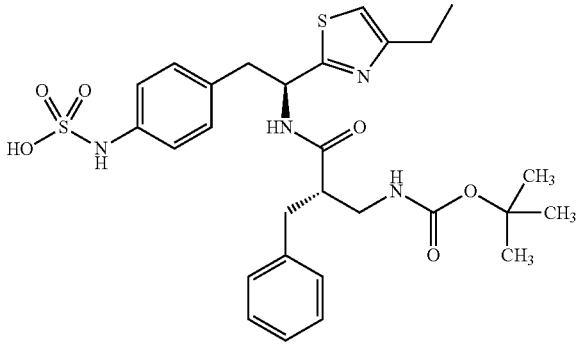 [SMILES: CCc1csc([C@H](Cc2ccc(NS(=O)(=O)O)cc2)NC(=O)[C@H](CNC(=O)OC(C)(C)C)Cc2ccccc2)n1] {1-[1-(5-Ethylthiazol-2-yl)-(S)-2-(4-sulfoaminophenyl)ethyl-carbamoyl]-(S)-2-phenylethyl}methyl carbamic acid tert-butyl ester | 0.031 |
| AA4 | 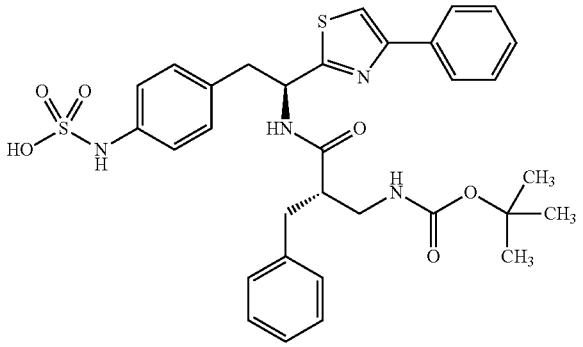 [SMILES: CC(C)(C)OC(=O)NC[C@H](Cc1ccccc1)C(=O)N[C@@H](Cc1ccc(NS(=O)(=O)O)cc1)c1nc(-c2ccccc2)cs1] {1-[1-(5-phenylthiazol-2-yl)-(S)-2-(4-sulfoaminophenyl)ethylcarbamoyl]-(S)-2-phenylethyl}methyl carbamic acid tert-butyl ester | <5x10$^{-8}$ |
| AA5 | 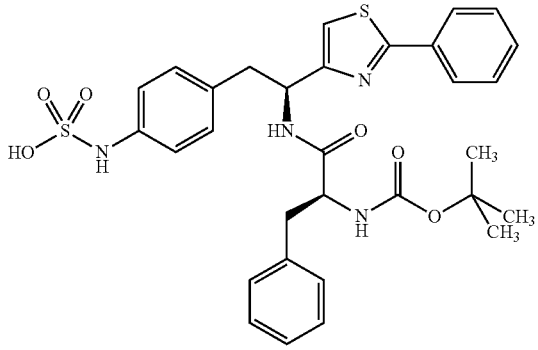 [SMILES: CC(C)(C)OC(=O)N[C@@H](Cc1ccccc1)C(=O)N[C@@H](Cc1ccc(NS(=O)(=O)O)cc1)c1csc(-c2ccccc2)n1] 4-{(S)-2-(S)-2-(tert-Butoxycarbonylamino)-3-phenylpropanamido-2-(2-phenylthiazol-4-yl)}phenylsulfamic acid | <5x10$^{-8}$ |

TABLE 2-continued
| No. | Compound | HPTPβ IC$_{50}$ μM |
|---|---|---|
| AA6 | 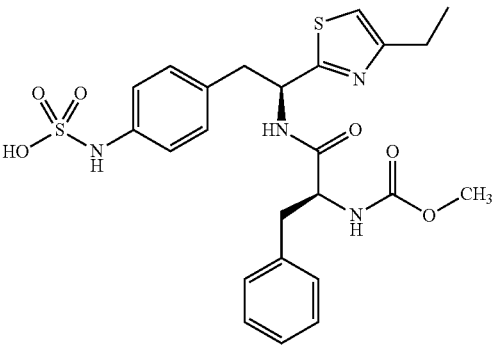 [SMILES: CCc1csc([C@H](Cc2ccc(NS(=O)(=O)O)cc2)NC(=O)[C@H](Cc2ccccc2)NC(=O)OC)n1] 4-{(S)-2-(4-Ethylthiazol-2-yl)-2-[(S)-2-(methoxycarbonylamino)-3-phenylpropanamido]ethyl}phenylsulfamic acid | 0.000162 |
| AA7 | 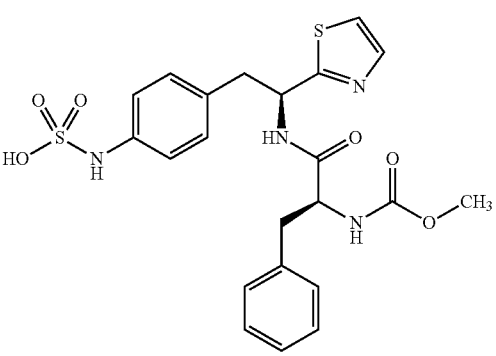 [SMILES: COC(=O)N[C@@H](Cc1ccccc1)C(=O)N[C@@H](Cc1ccc(NS(=O)(=O)O)cc1)c1nccs1] 4-{(S)-2-[(S)-2-(Methoxycarbonylamino)-3-phenylpropanamido]-2-(thiazol-2-yl)ethyl}phenylsulfamic acid | 0.006 |
| AA8 | 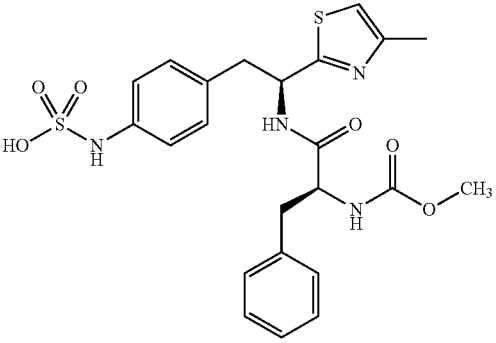 [SMILES: COC(=O)N[C@@H](Cc1ccccc1)C(=O)N[C@@H](Cc1ccc(NS(=O)(=O)O)cc1)c1nc(C)cs1] 4-{(S)-2-[(S)-2-(Methoxycarbonylamino)-3-phenylpropanamido]-2-(4-methylthiazol-2-yl)ethyl}phenylsulfamic acid | 0.001 |

TABLE 2-continued
| No. | Compound | HPTPβ IC$_{50}$ μM |
|---|---|---|
| AA9 | 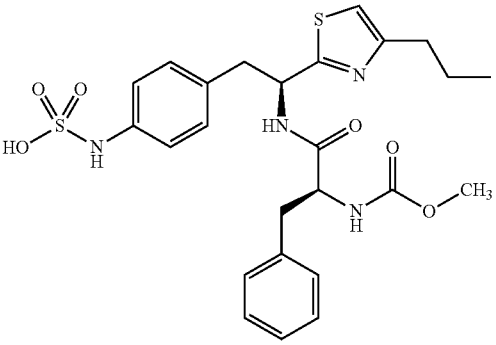 4-{(S)-2-[(S)-2-(Methoxycarbonylamino)-3-phenylpropanamido]-2-(4-propylthiazol-2-yl)ethyl}phenylsulfamic acid | 0.0001 |
| AA10 | 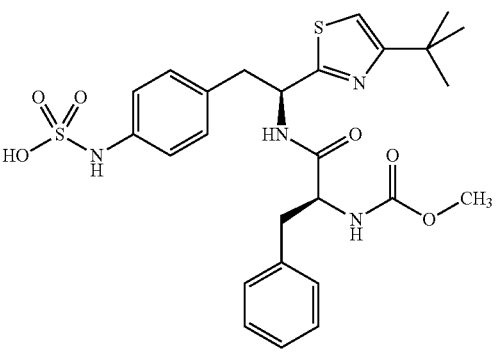 [SMILES: COC(=O)N[C@@H](Cc1ccccc1)C(=O)N[C@@H](Cc1ccc(NS(=O)(=O)O)cc1)c1nc(C(C)(C)C)cs1] 4-{(S)-2-(4-tert-Butylthiazol-2-yl)-2-[(S)-2-(methoxycarbonylamino)-3-phenylpropanamido]ethyl}phenylsulfamic acid | 0.0002 |
| AA11 | 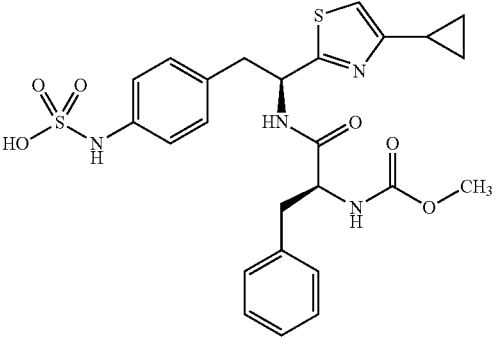 [SMILES: COC(=O)N[C@@H](Cc1ccccc1)C(=O)N[C@@H](Cc1ccc(NS(=O)(=O)O)cc1)c1nc(C2CC2)cs1] 4-{(S)-2-(4-Cyclopropylthiazol-2-yl)-2-[(S)-2-(methoxycarbonylamino)-3-phenylpropanamido]ethyl}phenylsulfamic acid | 0.00001 |

TABLE 2-continued
| No. | Compound | HPTPβ IC$_{50}$ μM |
|---|---|---|
| AA12 | 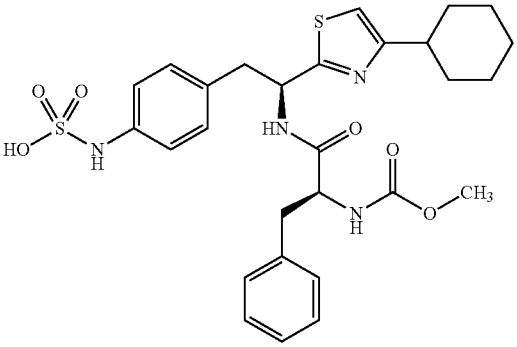 [SMILES: COC(=O)N[C@@H](Cc1ccccc1)C(=O)N[C@@H](Cc1ccc(NS(=O)(=O)O)cc1)c1nc(C2CCCCC2)cs1] 4-{(S)-2-(4-Cyclohexylthiazol-2-yl)-2-[(S)-2-(methoxycarbonylamino)-3-phenyl-propanamido]ethyl}phenylsulfamic acid | <5x10$^{-8}$ |
| AA13 | 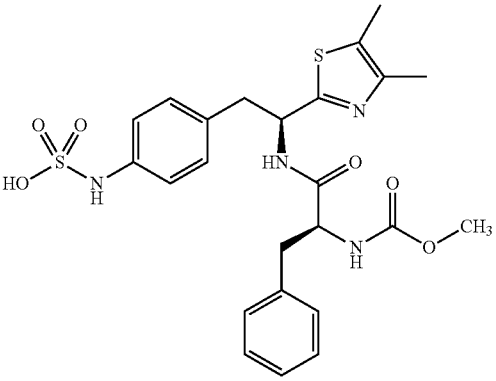 [SMILES: COC(=O)N[C@@H](Cc1ccccc1)C(=O)N[C@@H](Cc1ccc(NS(=O)(=O)O)cc1)c1nc(C)c(C)s1] 4-{(S)-2-(4,5-Dimethylthiazol-2-yl)-2-[(S)-2-(methoxycarbonylamino)-3-phenyl-propanamido]ethyl}phenylsulfamic acid | 0.001 |
| AA14 | 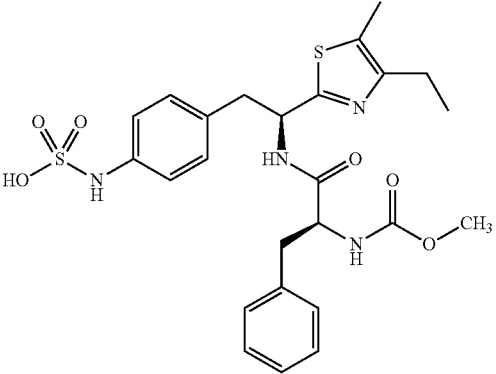 [SMILES: CCc1nc([C@H](Cc2ccc(NS(=O)(=O)O)cc2)NC(=O)[C@H](Cc2ccccc2)NC(=O)OC)sc1C] 4-{(S)-2-(4-Ethyl-5-methylthiazol-2-yl)-2-[(S)-2-(methoxy-carbonylamino)-3-phenyl-propanamido]ethyl}phenylsulfamic acid | 0.0001 |

TABLE 2-continued

| No. | Compound | HPTPβ IC$_{50}$ μM |
|---|---|---|
| AA15 | 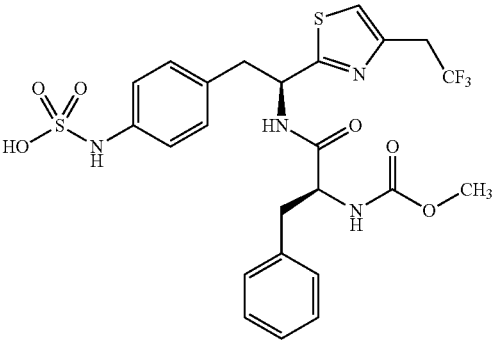 [SMILES: COC(=O)N[C@@H](Cc1ccccc1)C(=O)N[C@@H](Cc1ccc(NS(=O)(=O)O)cc1)c1nc(CC(F)(F)F)cs1]<br>4-{(S)-2-[(S)-2-(Methoxycarbonylamino)-3-phenylpropanamido]-2-[4-(2,2,2-trifluoroethyl)thiazol-2-yl]ethyl}phenylsulfamic acid | 0.0003 |
| AA16 | 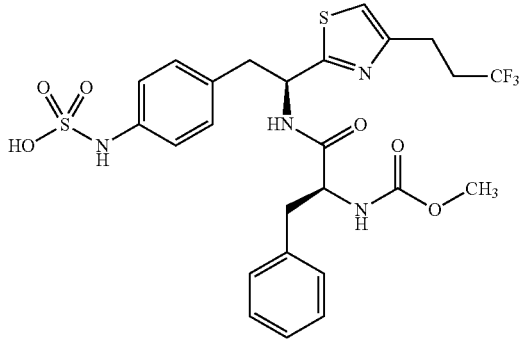 [SMILES: COC(=O)N[C@@H](Cc1ccccc1)C(=O)N[C@@H](Cc1ccc(NS(=O)(=O)O)cc1)c1nc(CCC(F)(F)F)cs1]<br>4-{(S)-2-[(S)-2-(Methoxycarbonylamino)-3-phenylpropanamido]-2-[4-(3,3,3-trifluoropropyl)thiazol-2-yl]ethyl}phenylsulfamic acid | 0.00008 |
| AA17 | 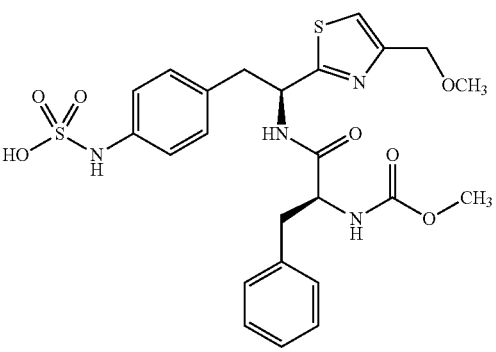 [SMILES: COCc1csc([C@H](Cc2ccc(NS(=O)(=O)O)cc2)NC(=O)[C@H](Cc2ccccc2)NC(=O)OC)n1]<br>4-{(S)-2-[(S)-2-(Methoxycarbonylamino)-3-phenylpropanamido]-2-[4-(methoxymethyl)thiazol-2-yl]ethyl}phenylsulfamic acid | 0.001 |

TABLE 2-continued
| No. | Compound | HPTPβ IC$_{50}$ μM |
|---|---|---|
| AA18 | 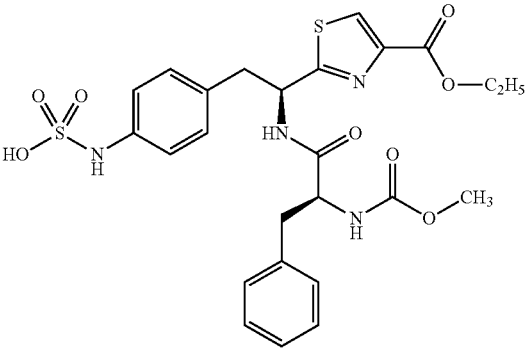 [SMILES: CCOC(=O)c1csc([C@H](Cc2ccc(NS(=O)(=O)O)cc2)NC(=O)[C@H](Cc2ccccc2)NC(=O)OC)n1]<br>4-{(S)-2-(4-(Ethoxycarbonyl)thiazol-2-yl)-2-[(S)-2-(methoxy-carbonylamino)-3-phenylpropanamido]ethyl}phenylsulfamic acid | 0.0002 |
| AA19 | 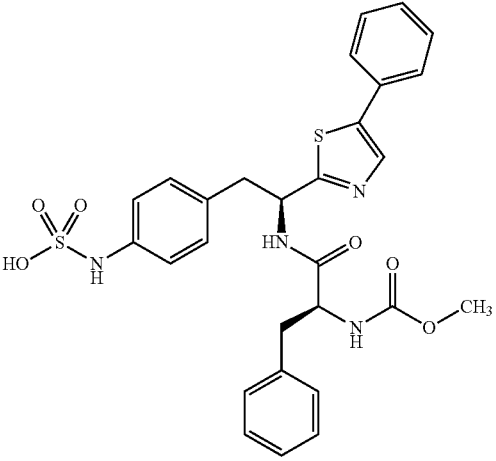 [SMILES: COC(=O)N[C@@H](Cc1ccccc1)C(=O)N[C@@H](Cc1ccc(NS(=O)(=O)O)cc1)c1ncc(-c2ccccc2)s1]<br>4-{(S)-2-[(S)-2-(Methoxycarbonylamino)-3-phenylpropanamido]-2-(5-phenylthiazol-2-yl)ethyl}phenylsulfamic acid | 0.0003 |
| AA20 | 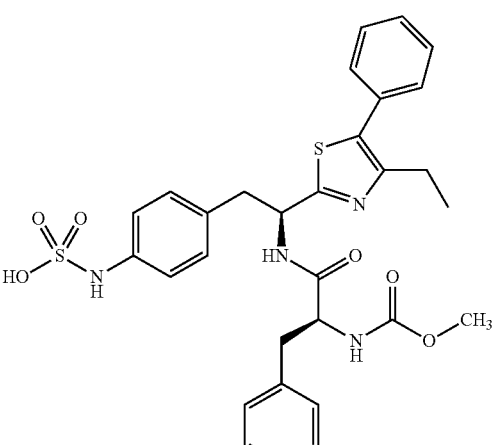<br>4-{(S)-2-(4-Ethyl-5-phenylthiazol-2-yl)-2-[(S)-2-(methoxy-carbonylamino)-3-phenyl-propanamido]ethyl}phenylsulfamic acid | <5x10$^{-8}$ |

TABLE 2-continued
| No. | Compound | HPTPβ IC$_{50}$ μM |
|---|---|---|
| AA21 | 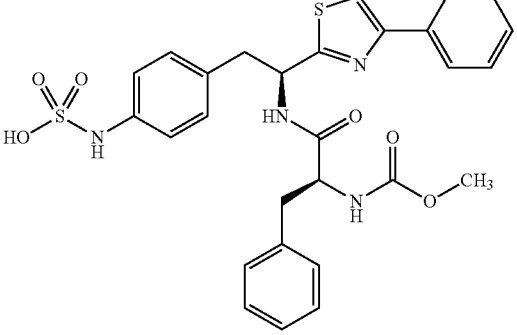
4-{(S)-2-[(S)-2-(Methoxycarbonylamino)-3-phenylpropanamido]-2-(4-phenylthiazol-2-yl)ethyl}phenylsulfamic acid | <2x10$^{-6}$ |
| AA22 | 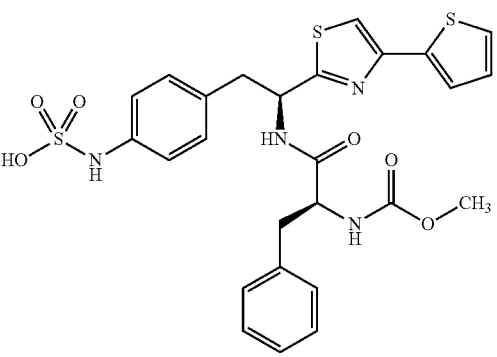 [SMILES: COC(=O)N[C@@H](Cc1ccccc1)C(=O)N[C@@H](Cc1ccc(NS(=O)(=O)O)cc1)c1nc(-c2cccs2)cs1]
4-{(S)-2-[(S)-2-(Methoxycarbonylamino)-3-phenylpropanamido]-2-[4-(thiophen-2-yl)thiazol-2-yl]ethyl}phenylsulfamic acid | <5x10$^{-8}$ |
| AA23 | 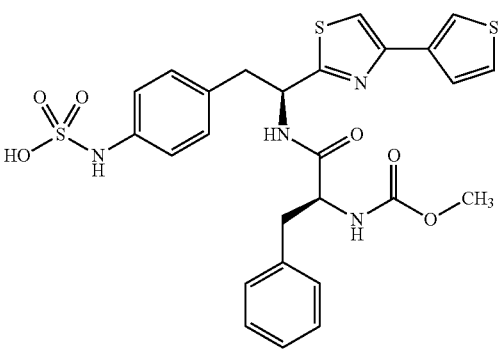 [SMILES: COC(=O)N[C@@H](Cc1ccccc1)C(=O)N[C@@H](Cc1ccc(NS(=O)(=O)O)cc1)c1nc(-c2ccsc2)cs1]
4-{(S)-2-[(S)-2-(Methoxycarbonylamino)-3-phenylpropanamido]-2-[4-(thiophen-3-yl)thiazol-2-yl]ethyl}phenylsulfamic acid | 0.00009 |

TABLE 2-continued

| No. | Compound | HPTPβ IC$_{50}$ μM |
|---|---|---|
| AA24 | 4-{(S)-2-(5,6-Dihydro-4H-cyclopenta[d]thiazol-2-yl)-2-[(S)-2-(methoxycarbonylamino)-3-phenylpropanamido]ethyl}phenylsulfamic acid | 0.001 |
| AA25 | 4-{(S)-2-[(S)-2-(Methoxycarbonylamino)-3-phenylpropanamido]-2-(4,5,6,7-tetrahydrobenzo[d]thiazol-2-yl)ethyl}phenylsulfamic acid | 0.0004 |
| AA26 | 4-{(S)-2-[4-(5-Chlorothiophen-2-yl)thiazol-2-yl]-2-[(S)-2-(methoxycarbonylamino)-3-phenylpropanamido]ethyl}phenyl-sulfamic acid | <5x10$^{-8}$ |

TABLE 2-continued
| No. | Compound | HPTPβ IC$_{50}$ μM |
|---|---|---|
| AA27 | 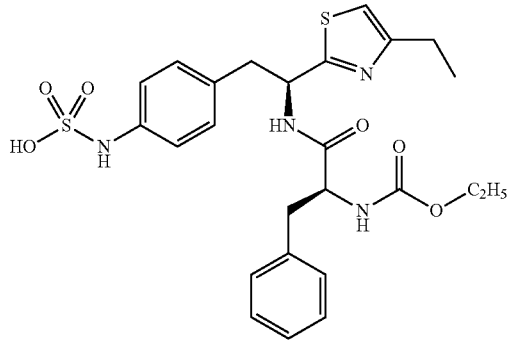 [SMILES: CCOC(=O)N[C@@H](Cc1ccccc1)C(=O)N[C@@H](Cc1ccc(NS(=O)(=O)O)cc1)c1nc(CC)cs1] 4-{(S)-2-[(S)-2-(Ethoxycarbonylamino)-3-phenylpropanamido]-2-(4-ethylthiazol-2-yl)ethyl}phenylsulfamic acid | 0.00014 |
| AA28 | 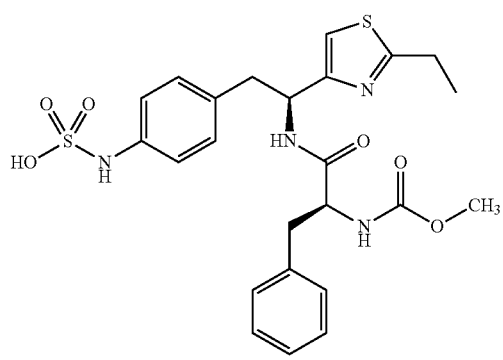 [SMILES: CCc1nc([C@H](Cc2ccc(NS(=O)(=O)O)cc2)NC(=O)[C@H](Cc2ccccc2)NC(=O)OC)cs1] 4-{(S)-2-[(S)-2-(Methoxycarbonylamino)-3-phenylpropanamido]-2-(2-ethylthiazol-4-yl)ethyl}phenylsulfamic acid | 0.0001 |
| AA29 | 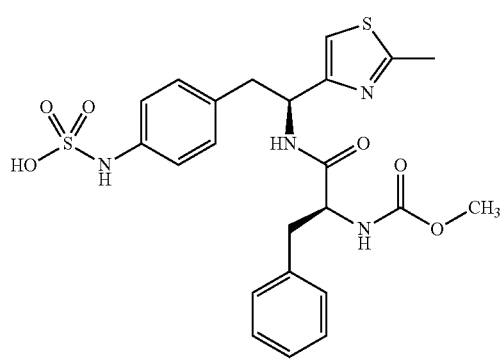 [SMILES: COC(=O)N[C@@H](Cc1ccccc1)C(=O)N[C@@H](Cc1ccc(NS(=O)(=O)O)cc1)c1csc(C)n1] 4-{(S)-2-[(S)-2-(Methoxycarbonylamino)-3-phenylpropanamido]-2-(2-methylthiazol-4-yl)ethyl}phenylsulfamic acid | 0.001 |

TABLE 2-continued

| No. | Compound | HPTPβ IC$_{50}$ μM |
|---|---|---|
| AA30 | 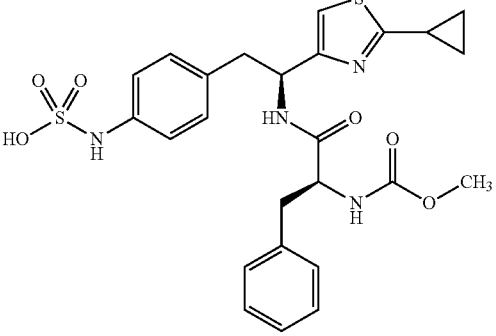<br>4-{(S)-2-(2-Cyclopropylthiazol-4-yl)-2-[(S)-2-(methoxy-carbonylamino)-3-phenylpropanamido]ethyl}phenylsulfamic acid | 0.0002 |
| AA31 | 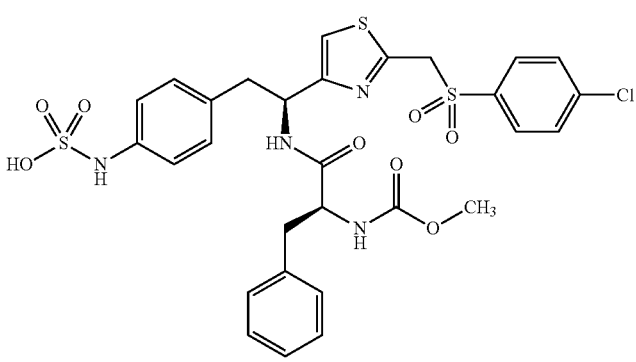 [SMILES: COC(=O)N[C@@H](Cc1ccccc1)C(=O)N[C@@H](Cc1ccc(NS(=O)(=O)O)cc1)c1csc(CS(=O)(=O)c2ccc(Cl)cc2)n1]<br>4-{(S)-2-{2-[(4-Chlorophenylsulfonyl)methyl]thiazol-4-yl}-2-[(S)-2-(methoxycarbonylamino)-3-phenylpropanamido]ethyl}phenylsulfamic acid | 0.00008 |
| AA32 | 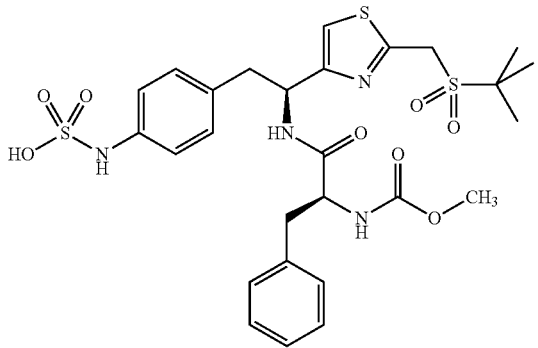 [SMILES: COC(=O)N[C@@H](Cc1ccccc1)C(=O)N[C@@H](Cc1ccc(NS(=O)(=O)O)cc1)c1csc(CS(=O)(=O)C(C)(C)C)n1]<br>4-{(S)-2-[2-(tert-Butylsulfonylmethyl)thiazol-4-yl]-2-[(S)-2-(methoxycarbonylamino)-3-phenylpropanamido]ethyl}phenylsulfamic acid | 0.002 |

TABLE 2-continued

| No. | Compound | HPTPβ IC$_{50}$ μM |
|---|---|---|
| AA33 | 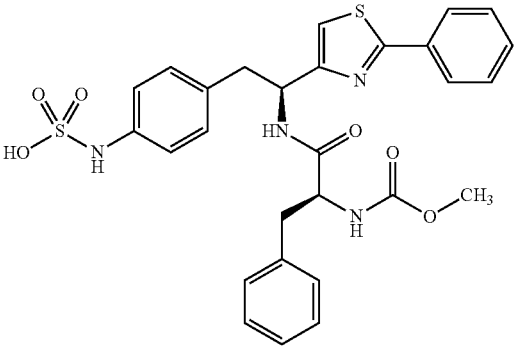 [SMILES: COC(=O)N[C@@H](Cc1ccccc1)C(=O)N[C@@H](Cc1ccc(NS(=O)(=O)O)cc1)c1csc(-c2ccccc2)n1]<br>4-{(S)-2-[(S)-2-(Methoxycarbonylamino)-3-phenylpropionamido]-2-(2-phenylthiazole-4-yl)ethyl}phenylsulfamic acid | 7x10$^{-7}$ |
| AA34 | 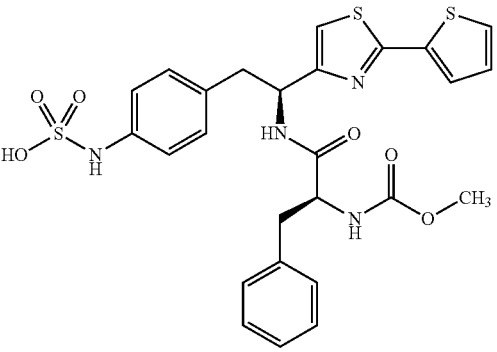 [SMILES: COC(=O)N[C@@H](Cc1ccccc1)C(=O)N[C@@H](Cc1ccc(NS(=O)(=O)O)cc1)c1csc(-c2cccs2)n1]<br>4-{(S)-2-[(S)-2-(Methoxycarbonylamino)-3-phenylpropanamido]-2-[2-(thiophen-2-yl)thiazol-4-yl]ethyl}phenylsulfamic acid | 5x10$^{-8}$ |
| AA35 | 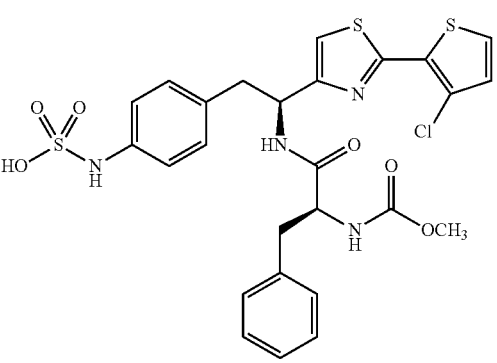 [SMILES: COC(=O)N[C@@H](Cc1ccccc1)C(=O)N[C@@H](Cc1ccc(NS(=O)(=O)O)cc1)c1csc(-c2sccc2Cl)n1]<br>4-{(S)-2-[2-(3-Chlorothiophen-2-yl)thiazol-4-yl]-2-[(S)-2-(methoxycarbonylamino)-3-phenylpropanamido]ethyl}phenylsulfamic acid | <5x10$^{-8}$ |

TABLE 2-continued
| No. | Compound | HPTPβ IC$_{50}$ μM |
|---|---|---|
| AA36 | 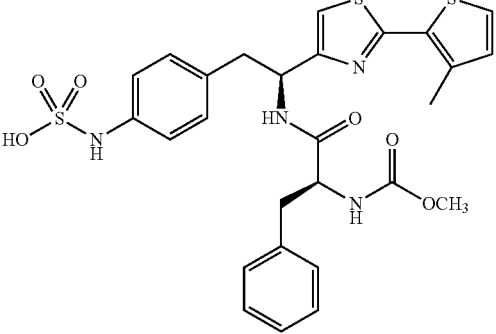 4-{(S)-2-[(S)-2-(Methoxycarbonylamino)-3-phenylpropanamido]-2-[2-(3-methylthiophen-2-yl)thiazol-4-yl]ethyl}phenylsulfamic acid | <5x10$^{-8}$ |
| AA37 | 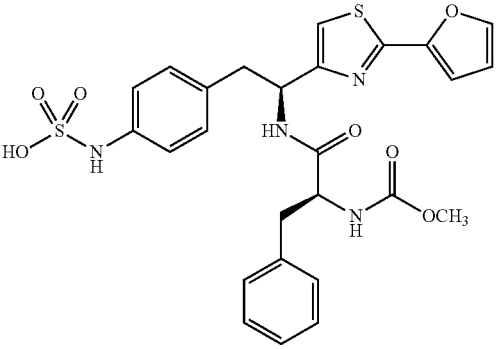 [SMILES: COC(=O)N[C@@H](Cc1ccccc1)C(=O)N[C@@H](Cc1ccc(NS(=O)(=O)O)cc1)c1csc(-c2ccco2)n1] 4-{[(S)-2-(2-(Furan-2-yl)thiazol-4)yl]-2-[(S)-2-(methoxycarbonylamino)-3-phenylpropanamido]ethyl}phenylsulfamic acid | 0.0004 |
| AA38 | 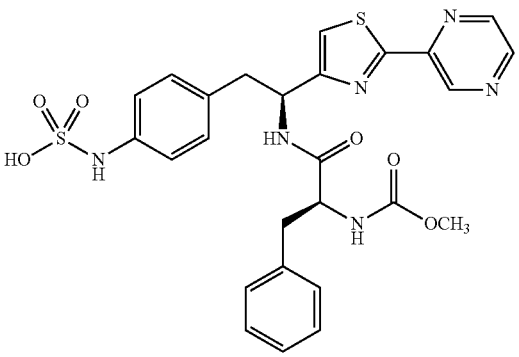 [SMILES: COC(=O)N[C@@H](Cc1ccccc1)C(=O)N[C@@H](Cc1ccc(NS(=O)(=O)O)cc1)c1csc(-c2cnccn2)n1] 4-{(S)-2-[(S)-2-(Methoxycarbonylamino)-3-phenylpropanamido]-2-[2-(pyrazin-2-yl)thiazol-4-yl]ethyl}phenylsulfamic acid | 0.003 |

TABLE 2-continued
| No. | Compound | HPTPβ IC$_{50}$ µM |
|---|---|---|
| AA39 | 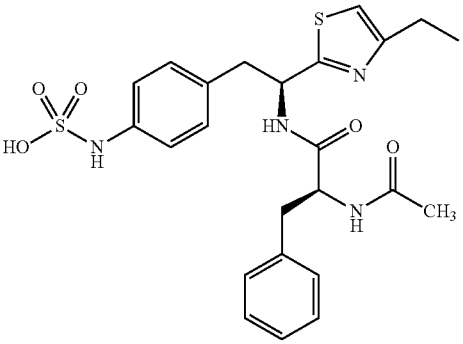 [SMILES: CCc1csc([C@H](Cc2ccc(NS(=O)(=O)O)cc2)NC(=O)[C@H](Cc2ccccc2)NC(C)=O)n1] 4-[(S)-2-((S)-2-Acetamido-3-phenylpropanamido)-2-(4-ethylthiazol-2-yl)ethyl]phenylsulfamic acid | 0.001 |
| AA40 | 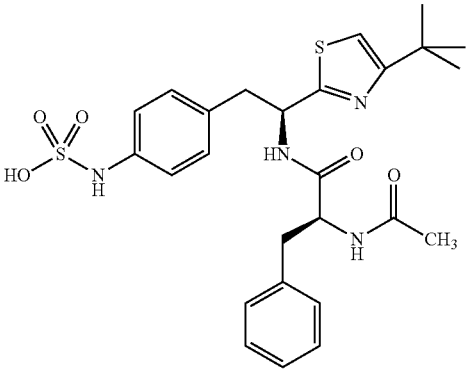 [SMILES: CC(=O)N[C@@H](Cc1ccccc1)C(=O)N[C@@H](Cc1ccc(NS(=O)(=O)O)cc1)c1nc(C(C)(C)C)cs1] 4-[(S)-2-((S)-2-Acetamido-3-phenylpropanamido)-2-(4-tert-butylthiazol-2-yl)ethyl]phenylsulfamic acid | 0.0003 |
| AA41 | 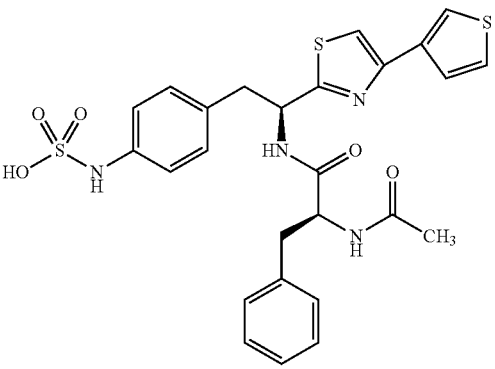 [SMILES: CC(=O)N[C@@H](Cc1ccccc1)C(=O)N[C@@H](Cc1ccc(NS(=O)(=O)O)cc1)c1nc(-c2ccsc2)cs1] 4-{(S)-2-((S)-2-Acetamido-3-phenylpropanamido)-2-[4-(thiophen-3-yl)thiazol-2-yl]ethyl}phenylsulfamic acid | 0.00024 |

TABLE 2-continued

| No. | Compound | HPTPβ IC$_{50}$ μM |
|---|---|---|
| AA42 | 4-{(S)-2-[(S)-2-(tert-Butoxycarbonylamino)-3-methylbutanamido]-2-(4-ethylthiazol-2-yl)ethyl}phenylsulfamic acid | 0.006 |
| AA43 | (S)-4-{2-[2-(tert-Butoxycarbonylamino)acetamido]-2-(4-ethylthiazol-2-yl)ethyl}phenylsulfamic acid | 0.028 |
| AA44 | (S)-4-{2-(4-Ethylthiazol-2-yl)-2-[2-(methoxycarbonylamino)acetamido]ethyl}phenylsulfamic acid | 0.020 |
| AA45 | 4-{(S)-2-(4-Ethylthiazol-2-yl)-2-[(S)-2-(methoxycarbonylamino)-3-methylbutanamido]-ethyl}phenylsulfamic acid | 0.003 |

TABLE 2-continued

| No. | Compound | HPTPβ IC$_{50}$ μM |
|---|---|---|
| AA46 | 4-{(S)-2-[(S)-2-(tert-Butoxycarbonylamino)-4-methylpentanamido]-2-(4-ethylthiazol-2-yl)ethyl}phenylsulfamic acid | 0.001 |
| AA47 | 4-{(S)-2-(4-Ethylthiazol-2-yl)-2-[(S)-2-(methoxycarbonylamino)-4-methylpentanamido]ethyl}phenylsulfamic acid | 0.0003 |
| AA48 | 4-((S)-2-(4-Ethylthiazol-2-yl)-2-{(S)-2-[2-(methoxycarbonylamino)-acetamido]-3-phenylpropanamido}ethyl)phenylsulfamic acid | 0.0003 |
| AA49 | 4-{(S)-2-[(S)-2-(Methoxycarbonylamino)-4-methylpentanamido]-2-[2-(thiophen-2-yl)thiazol-4-yl]ethyl}phenylsulfamic acid | <5x10$^{-8}$ |

TABLE 2-continued

| No. | Compound | HPTPβ IC$_{50}$ μM |
|---|---|---|
| AA50 | (S)-4-{2-[2-(tert-Butoxycarbonylamino)acetamido]-2-(4-ethylthiazol-2-yl)ethyl}-phenylsulfamic acid | 0.028 |
| AA51 | [1-(S)-(Phenylthiazol-2-yl)-2-(4-sulfoaminophenyl)ethyl]-carbamic acid tert-butyl ester | 0.049 |
| AA52 | (S)-4-(2-(4-Methylthiazol-2-yl)-2-pivalamidoethyl)phenyl-sulfamic acid | 0.112 |
| AA53 | (S)-4-(2-(4-Ethylthiazol-2-yl)-2-pivalamidoethyl)phenyl-sulfamic acid | 0.085 |
| AA54 | (S)-4-{2-[4-(hydroxymethyl)thiazol-2-yl]-2-pivalamidoethyl}phenyl-sulfamic acid | 0.266 |

TABLE 2-continued

| No. | Compound | HPTPβ IC$_{50}$ μM |
|---|---|---|
| AA55 | 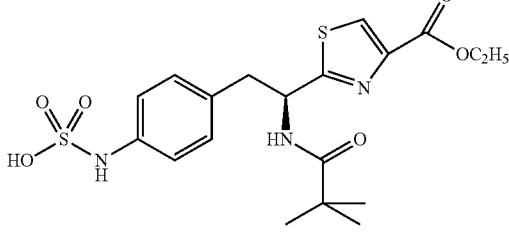<br>(S)-4-{[2-(4-Ethoxycarbonyl)thiazol-2-yl]-2-pivalamidoethyl}phenylsulfamic acid | 0.584 |
| AA56 | 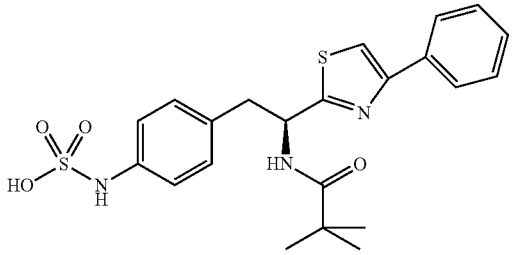 [SMILES: CC(C)(C)C(=O)N[C@@H](Cc1ccc(NS(=O)(=O)O)cc1)c1nc(-c2ccccc2)cs1]<br>(S)-4-(2-(4-Phenylthiazol-2-yl)-2-pivalamidoethyl)phenylsulfamic acid | 0.042 |
| AA57 | 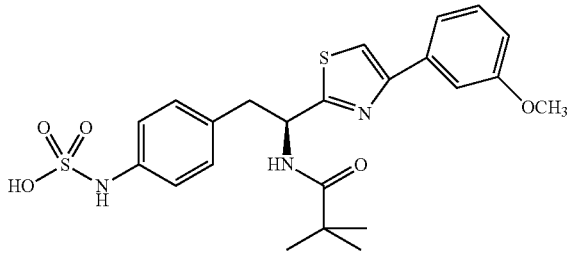 [SMILES: COc1cccc(-c2csc([C@H](Cc3ccc(NS(=O)(=O)O)cc3)NC(=O)C(C)(C)C)n2)c1]<br>4-((S)-2-(4-(3-Methoxyphenyl)thiazol-2-yl)-2-pivalamidoethyl)phenylsulfamic acid | 0.110 |
| AA58 | 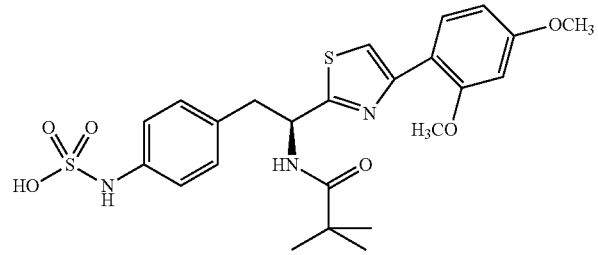 [SMILES: COc1ccc(-c2csc([C@H](Cc3ccc(NS(=O)(=O)O)cc3)NC(=O)C(C)(C)C)n2)c(OC)c1]<br>4-((S)-2-(4-(2,4-Dimethoxyphenyl)thiazol-2-yl)-2-pivalamidoethyl)phenyl-sulfamic acid | 0.086 |
| AA59 | 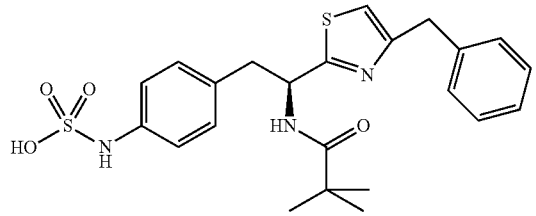 [SMILES: CC(C)(C)C(=O)N[C@@H](Cc1ccc(NS(=O)(=O)O)cc1)c1nc(Cc2ccccc2)cs1]<br>(S)-4-(2-(4-Benzylthiazol-2-yl)-2-pivalamidoethyl)phenylsulfamic acid | 0.113 |

TABLE 2-continued

| No. | Compound | HPTPβ IC$_{50}$ μM |
|---|---|---|
| AA60 | (S)-4-(2-(4-(3-Methoxybenzyl)thiazol-2-yl)-2-pivalamidoethyl)phenylsulfamic acid | 0.132 |
| AA61 | 4-((S)-2-(4-(2,3-Dihydrobenzo[b][1,4]dioxin-6-yl)thiazol-2-yl)-2-pivalamidoethyl)phenylsulfamic acid | 0.138 |
| AA62 | (S)-4-(2-(5-Methyl-4-phenylthiazol-2-yl)-2-pivalamidoethyl)phenylsulfamic acid | 0.098 |
| AA63 | (S)-4-(2-(4-(Biphen-4-yl)thiazol-2-yl)-2-pivalamidoethyl)phenylsulfamic acid | 0.381 |

TABLE 2-continued

| No. | Compound | HPTPβ IC$_{50}$ μM |
|---|---|---|
| AA64 | (S)-4-(2-tert-Butoxycarbonylamino)-2-(2-methylthiazol-4-yl)ethyl)phenylsulfamic acid | 0.033 |
| AA65 | (S)-4-(2-(tert-Butoxycarbonylamino)-2-(4-propylthiazol-2-yl)ethyl)phenyl sulfamic acid | 0.04 |
| AA66 | (S)-4-(2-(tert-Butoxycarbonylamino)-2-(4-tert-butylthiazol-2-yl)ethyl)phenyl sulfamic acid | 0.027 |
| AA67 | (S)-4-(2-(tert-Butoxycarbonylamino)-2-(4-(methoxymethyl)thiazol-2-yl)ethyl)-phenyl sulfamic acid | 0.18 |

TABLE 2-continued

| No. | Compound | HPTPβ IC$_{50}$ μM |
|---|---|---|
| AA68 | (S)-4-(2-(tert-Butoxycarbonylamino)-2-(4-(hydroxymethyl)thiazol-2-yl)ethyl)phenylsulfamic acid | 0.644 |
| AA69 | (S)-4-(2-tert-Butoxycarbonylamino)-2-(4-(2-ethoxy-2-oxoethyl)thiazol-2-yl)ethyl)phenylsulfamic acid | 0.167 |
| AA70 | (S)-4-(2-(tert-Butoxycarbonyl)-2-(4-(2-(2-methoxy-2-oxoethylamino)-2-oxoethyl)thiazole-2-yl)ethyl)phenylsulfamic acid | 0.132 |
| AA71 | (S)-4-(2-(tert-Butoxycarbonylamino)-2-(2-pivalamidothiazol-4-yl)ethyl)phenylsulfamic acid | 0.555 |

TABLE 2-continued

| No. | Compound | HPTPβ IC$_{50}$ μM |
|---|---|---|
| AA72 | (S)-4-(2-(tert-Butoxycarbonylamino)-2-(5-phenylthiazol-2-yl)ethyl)-phenyl sulfamic acid | 0.308 |
| AA73 | 4-((S)-2-(tert-Butoxycarbonylamino)-2-(4-(3-(trifluoromethyl)phenyl)thiazol-2-yl)ethyl)-phenyl sulfamic acid | 0.253 |
| AA74 | 4-((S)-2-(tert-Butoxycarbonylamino)-2-(4-(thiophen-3-yl)thiazol-2-yl)ethyl)phenylsulfamic acid | 0.045 |
| AA75 | (S)-{4-[2-(4-Ethylthiazol-2-yl)-2-(phenylacetylamido)ethyl]-phenyl}sulfamic acid | 0.05 |

TABLE 2-continued

| No. | Compound | HPTPβ IC$_{50}$ μM |
|---|---|---|
| AA76 | (S)-4-(2-(4-Ethylthiazol-2-yl)-2-(2-(2-fluorophenyl)acetamido)ethyl)phenyl-sulfamic acid | 0.012 |
| AA77 | (S)-4-(2-(4-Ethylthiazol-2-yl)-2-(2-(3-fluorophenyl)acetamido)ethyl)phenyl-sulfamic acid | 0.0003 |
| AA78 | (S)-4-(2-(2-(2,3-Difluorophenyl)acetamido)-2-(4-ethylthiazol-2-yl)ethyl)phenyl-sulfamic acid | 0.028 |
| AA79 | (S)-4-(2-(2-(3,4-Difluorophenyl)acetamido)-2-(4-ethylthiazol-2-yl)ethyl)phenyl-sulfamic acid | 0.075 |

TABLE 2-continued
| No. | Compound | HPTPβ IC$_{50}$ μM |
|---|---|---|
| AA80 | 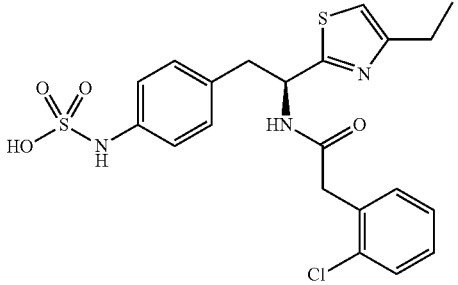 [SMILES: CCc1csc([C@H](Cc2ccc(NS(=O)(=O)O)cc2)NC(=O)Cc2ccccc2Cl)n1]<br>(S)-4-(2-(2-(2-Chlorophenyl)acetamido)-2-(4-ethylthiazol-2-yl)ethyl)phenyl-sulfamic acid | 0.056 |
| AA81 | 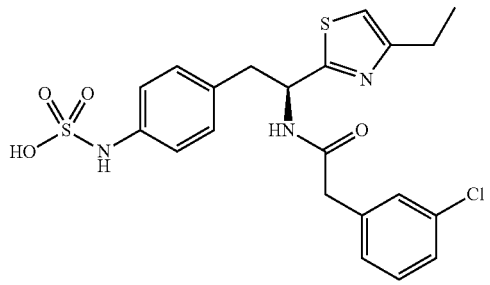 [SMILES: CCc1csc([C@H](Cc2ccc(NS(=O)(=O)O)cc2)NC(=O)Cc2cccc(Cl)c2)n1]<br>(S)-4-(2-(2-(3-Chlorophenyl)acetamido)-2-(4-ethylthiazol-2-yl)ethyl)phenyl-sulfamic acid | 0.033 |
| AA82 | 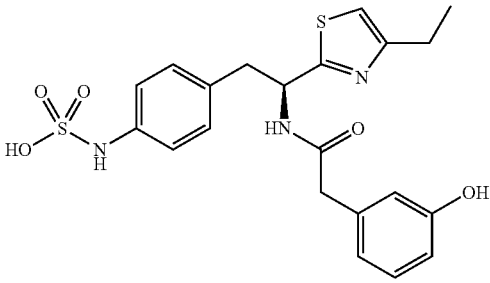 [SMILES: CCc1csc([C@H](Cc2ccc(NS(=O)(=O)O)cc2)NC(=O)Cc2cccc(O)c2)n1]<br>(S)-4-(2-(4-Ethylthiazol-2-yl)-2-(2-(3-hydroxyphenyl)acetamido)ethyl)phenyl-sulfamic acid | 0.04 |
| AA83 | 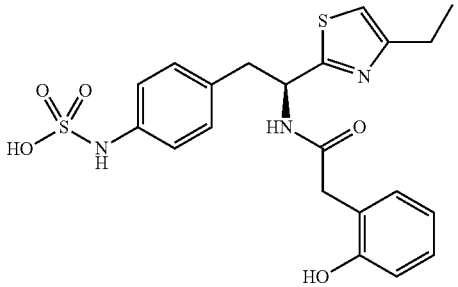 [SMILES: CCc1csc([C@H](Cc2ccc(NS(=O)(=O)O)cc2)NC(=O)Cc2ccccc2O)n1]<br>(S)-4-(2-(4-Ethylthiazol-2-yl)-2-(2-(2-methoxyphenyl)acetamido)ethyl)phenyl-sulfamic acid | 0.014 |

TABLE 2-continued

| No. | Compound | HPTPβ IC$_{50}$ μM |
|---|---|---|
| AA84 | (S)-4-(2-(4-Ethylthiazol-2-yl)-2-(2-(3-methoxyphenyl)acetamido)ethyl)phenyl-sulfamic acid | 0.008 |
| AA85 | (S)-4-(2-(4-Ethylthiazol-2-yl)-2-(3-phenylpropanamido)ethyl)phenylsulfamic acid | 0.002 |
| AA86 | (S)-4-(2-(2-(3,4-Dimethoxyphenyl)acetamido)-2-(4-ethylthiazol-2-yl)ethyl)-phenylsulfamic acid | 0.028 |
| AA87 | (S)-4-(2-(2-(2,3-Dimethoxyphenyl)acetamido)-2-(4-ethylthiazol-2-yl)ethyl)-phenylsulfamic acid | 0.037 |

TABLE 2-continued

| No. | Compound | HPTPβ IC$_{50}$ μM |
|---|---|---|
| AA88 | (S)-4-(2-(3-(3-Chlorophenyl)propanamido)-2-(4-ethylthiazol-2-yl)ethyl)phenyl-sulfamic acid | 0.0002 |
| AA89 | (S)-4-(2-(4-Ethylthiazol-2-yl)-2-(3-(2-methoxyphenyl)propanamido)ethyl)phenyl-sulfamic acid | 0.003 |
| AA90 | (S)-4-(2-(4-Ethylthiazol-2-yl)-2-(3-(3-methoxyphenyl)propanamido)ethyl)phenyl-sulfamic acid | 0.01 |
| AA91 | (S)-4-(2-(4-Ethylthiazol-2-yl)-2-(3-(4-methoxyphenyl)propanamido)ethyl)phenyl-sulfamic acid | 0.006 |

TABLE 2-continued

| No. | Compound | HPTPβ IC$_{50}$ μM |
|---|---|---|
| AA92 | 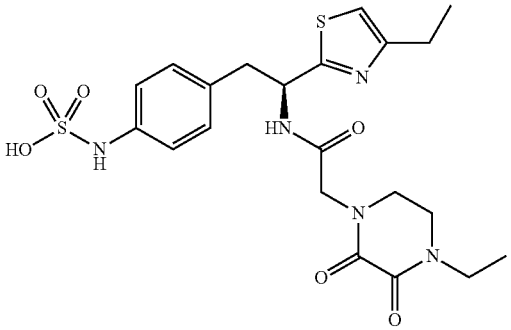 [SMILES: CCc1csc([C@H](Cc2ccc(NS(=O)(=O)O)cc2)NC(=O)CN2CCN(CC)C(=O)C2=O)n1]<br>(S)-4-{2-[2-[2-(4-Ethyl-2,3-dioxopiperazin-1-yl)acetamide]-2-(4-ethylthiazol-2-yl)ethyl}phenylsulfamic acid | 0.002 |
| AA93 | 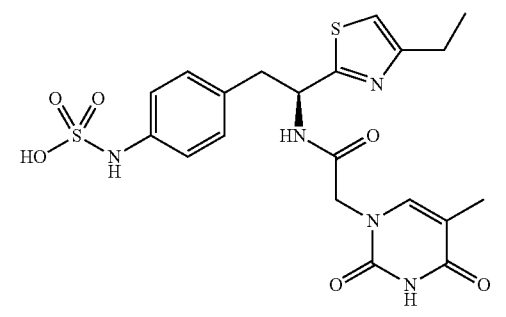 [SMILES: CCc1csc([C@H](Cc2ccc(NS(=O)(=O)O)cc2)NC(=O)Cn2cc(C)c(=O)[nH]c2=O)n1]<br>(S)-4-{2-(4-Ethylthiazol-2-yl)-2-[2-(5-methyl-2,4-dioxo-3,4-dihydropyrimidin-1(2H)-yl)acetamide]ethyl}phenylsulfamic acid | 0.002 |
| AA94 | 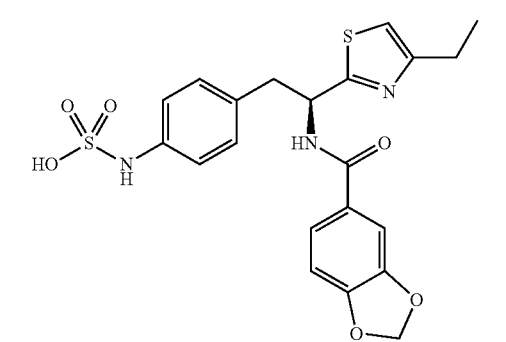 [SMILES: CCc1csc([C@H](Cc2ccc(NS(=O)(=O)O)cc2)NC(=O)c2ccc3c(c2)OCO3)n1]<br>(S)-4-[2-(Benzo[d][1,3]dioxole-5-carboxamido)-2-(4-ethylthiazol-2-yl)ethyl]phenylsulfamic acid | 0.042 |
| AA95 | 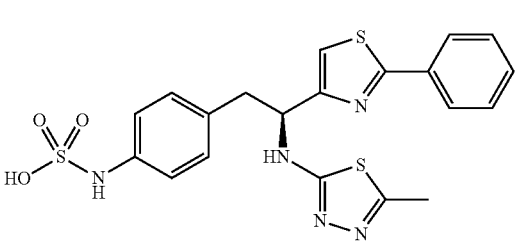 [SMILES: Cc1nnc(N[C@@H](Cc2ccc(NS(=O)(=O)O)cc2)c2csc(-c3ccccc3)n2)s1]<br>(S)-4-(2-(5-methyl-1,3,4-thiadiazol-2-ylamino)-2-(2-phenylthiazol-4-yl)ethyl)phenylsulfamic acid | 0.003 |

TABLE 2-continued

| No. | Compound | HPTPβ IC$_{50}$ μM |
|---|---|---|
| AA96 | (S)-4-(2-(5-Phenyl-1,3,4-thiadiazol-2-ylamino)-2-(2-phenylthiazol-4-yl)ethyl)-phenylsulfamic acid | 0.046 |
| AA97 | 4-((S)-2-(5-Propyl-1,3,4-thiadiazol-2-ylamino)-2-(2-(thiophen-2-yl)thiazol-4-yl)ethyl)phenylsulfamic acid | 0.0002 |
| AA98 | 4-((S)-2-(5-Benzyl-1,3,4-thiadiazol-2-ylamino)-2-(2-(thiophen-2-yl)thiazol-4-yl)ethyl)phenylsulfamic acid | 0.0006 |
| AA99 | 4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid | 0.002 |

TABLE 2-continued

| No. | Compound | HPTPβ IC$_{50}$ μM |
|---|---|---|
| AA100 | 4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid | 9x10$^{-6}$ |

Example 2: Preparation of a TPGS (Vitamin E) Solution for a Formulation Described Herein To prepare a TPGS solution for a formulation described herein, 20 g of TPGS is melted at 60-65° C., and 80 mL of water is heated to between 60 to 65° C. Over a 30 min period, under moderate stirring, the melted TPGS is added to the water while maintaining the temperature of the mixture at 60-65° C. The stirring is moderate to avoid formation of foam. The solubilization of the TPGS is complete after four hours stirring at 60-65° C. The TPGS solution is then cooled down to 20-25° C. under stirring to obtain a clear, slightly yellow solution.

Injectable Hydrogel with Vitamin E.

To prepare an injectable hydrogel based on PEG and Vitamin E, a methacrylated Vitamin E monomer is synthesized from methacryloyl chloride (0.324 g, 3.13 mmol, 1.25 equiv) and Vitamin E (1 g, 2.5 mmol, 1 equiv). The methacryloyl chloride is added dropwise into the Vitamin E in a tetrahydrofuran (THF, 15 mL) and triethylamine, (0.632 g, 6.26 mmol, 3 equiv) solution. The reaction is performed under nitrogen and is initially kept in a 0° C. ice bath for 4 h followed by room temperature for additional 18 h. After the reaction, the resultant salt (trimethylamine hydrochloride) is removed by filtration. The solvent is then evaporated to give a crude methacrylated Vitamin E monomer. This crude product is re-dissolved in anhydrous THF (5 mL) to precipitate any salt residues, with the process repeated once more for purification. The product is left in a vacuum oven at room temperature for 12 h. The methacrylated Vitamin E monomer is stored under nitrogen and away from light.

Copolymerization of Methacrylated Vitamin E and PEG Methacrylate.

For the synthesis of PEGMA-co-Vitamin E, methacrylated Vitamin E, PEGMA, and BPO (benzyl peroxide) are dissolved in 1,4-dioxane. The solution is first purged with nitrogen for 5 min, after which the reaction vessel is sealed and placed into an 80° C. oil bath for 24 h. The molecular weight of PEGMA-co-Vitamin E is adjusted by varying the amount of initiator as shown in TABLE 3 below.

TABLE 3

| | Reagents | | | |
|---|---|---|---|---|
| PEGMA-co-Vitamin E[1] | PEGMA (g) | Methacrylated Vitamin E (g) | BPO (mg) | 1,4-dioxane (mL) |
| #20 | 2 | 1 | 37 | 20 |
| #50 | 2 | 1 | 14.8 | 20 |
| #100 | 2 | 1 | 7.4 | 20 |

[1]Numbers represent nominal/targeted molecular weight of PEGMA-co-Vitamin E.

After the reaction, the solution is first cooled to room temperature, and then added dropwise to cold ether (about −20° C., 100 mL) under stirring to precipitate and collect PEGMA-co-Vitamin E polymer. This purification is repeated once. Finally, the residual solvent in the polymer is removed in a vacuum oven (40° C., 12 h).

Formulation of Injectable Hydrogel Precursor.

The PEGMA-co-Vitamin E polymer is formulated with low molecular weight (about 300 Da) PEG, and Vitamin E to generate the injectable hydrogel precursor solution (TABLE 4). PEGMA-co-Vitamin E polymer, PEG, and Vitamin E are placed in a vial and heated up to 80° C. until the polymer is melted and miscible with PEG and Vitamin E. The precursor is mixed by hand, and is predicted to result in a brown, but transparent solution, for injection either into water or tissue.

TABLE 4

| | PEGMA-co-Vitamin E | | | |
|---|---|---|---|---|
| Sample | # | mass (g) | PEG (g)[1] | Vitamin E (g) |
| 20P$_{43\%}$PEG$_{57\%}$Vitamin E$_{0\%}$ | 20 | 0.15 | 0.2 | — |
| 20P$_{33\%}$PEG$_{45\%}$Vitamin E$_{22\%}$ | 20 | 0.15 | 0.2 | 0.1 |
| 50P$_{33\%}$PEG$_{45\%}$Vitamin E$_{22\%}$ | 50 | 0.15 | 0.2 | 0.1 |
| 50P$_{42\%}$PEG$_{29\%}$Vitamin E$_{29\%}$ | 50 | 0.15 | 0.1 | 0.1 |
| 50P$_{60\%}$PEG$_{0\%}$Vitamin E$_{40\%}$ | 50 | 0.15 | 0 | 0.1 |
| 100P$_{33\%}$PEG$_{45\%}$Vitamin E$_{22\%}$ | 100 | 0.15 | 0.2 | 0.1 |

[1]The molecular weight of PEG used as solvent is 300 g/mol.

Characterization.

NMR spectra for methacrylated Vitamin E monomer and PEGMA-co-Vitamin E polymer are recorded on a Bruker Avance 600 MHz nuclear magnetic resonance spectrometer using deuterated chloroform as the solvent. Spectra are used to determine the ratio of PEG to Vitamin E in the copolymer. The molecular weight of PEGMA-co-Vitamin E copolymers is characterized by a gel permeation chromatograph (GPC) using N,N-dimethylformamide (DMF) with 50 mM LiBr as the solvent. The GPC is equipped with three Phenomenex Phenogel columns (300×4.6 mm, 5 μm; pore sizes: 100, 500, 104 Å). The elution rate is set at a 0.3 mL/min. The system is calibrated with PEG standards with molecular weights ranging from 600 to 167,000 g/mol. All samples are filtered using a 0.2 μm Teflon filter.

The morphologies of hydrogels are examined using scanning electron microscopy (SEM). Hydrogel samples are freeze-dried and then extracted with cold ether twice at −20° C. for 24 h, after which the dried hydrogels are left in a vacuum oven for 2 h. Samples are coated with a 10 nm coating of gold prior to imaging.

The mechanical performance of hydrogels immersed in water is tested using a MicroSquisher under compression mode. The cantilevers are fabricated using a 558.8 μm gauge cantilever and a square platen. During the test, a displacement of 20% is applied per compression. The durations of loading and recovery are 20 and 40 s, respectively. The compression modulus of a bulk hydrogel (sample thickness=2.43 mm, diameter=12.5 mm) is measured with an ARES rheometer operating under parallel-plate geometry with a 20% displacement.

The water content of hydrogel is determined by measuring the weight of gel saturated with water relative to the weight of gel after drying in a 100° C. oven.

Cytotoxicity of PEGMA-Co-Vitamin E, PEG, and Vitamin E.

Murine 3T3 fibroblasts are seeded in 96-well plates at a density of 8000 cells per well and cultivated in 100 μL of DMEM growth medium at 37° C. for 4 h to reach about 50% confluency. Growth medium is then replaced with 100 μL of fresh medium together with PEG (3% of the medium volume), Vitamin E (3% of the medium volume), and PEGMA-co-Vitamin E (about 10 mg polymer). Each condition is tested in triplicate. Following a 48 h incubation under standard culture conditions (37° C. and 5% $CO_2$), the culture medium is replaced with 100 μL Fluorobrite media, 10 μL MTT reagent, and incubated at 37° C. for an additional 3 h. The Fluorobrite-MTT solution is then removed, and 50 μL DMSO is added to dissolve the internalized purple formazan crystals. The absorbance of metabolized products is read using a microplate reader at 540 nm. Viability results are expressed as a percentage of the absorbance of the control cells without any treatment.

For the live/dead cells staining, cells are plated and treated as described for the MTT assay. Following a 48 h incubation, the cells are observed and culture media removed. Cells are washed gently with 100 μL of phosphate buffered saline (PBS) to remove any residual media and samples, and 50 μL PBS is added to each well. To three control wells, 100 μL of 70% ethanol is added to prepare a negative control. A fluorescent stain solution is prepared with 2 μM calcein AM and 4 μM ethidium homodimer-1 (EthD-1) in PBS, after which 50 μL of each stain is added to each well. Control wells (containing either live or dead cells) are also treated with both calcein AM and EthD-1 or calcein AM and EthD-1 alone. Following a 30 min incubation under dark conditions, the cells are photographed using the Axiovert 200 fluorescent microscope (Zeiss) and assessed using AxioVision microscopy software.

In Vitro Release of Atropine and Atropine Sulfate.

To examine the ability of the PEGMA-co-Vitamin E hydrogels to deliver drugs, atropine and atropine sulfate are used as example therapeutics. Atropine is added directly to the soluble Vitamin E fraction to form a homogeneous solution before formulating the injectable hydrogel precursor. Atropine sulfate can only be dispersed in Vitamin E, so the atropine sulfate is added after formulating the precursor. The final formulations of hydrogel precursors and loaded drug are shown in TABLE 5 below.

The drug release tests are performed using a Float-A-Lyzer G2 Dialysis Device (MW cut off: 300 kDa) using an inverse geometry, in which the drug-containing gel is located outside the membrane and the replaced (sampling) buffer is inside the membrane. For $50P_{33\%}PEG_{45\%}Ve_{22\%}$/Atropine, 76.4 mg of hydrogel precursor (containing about 5 mg Atropine) is injected into a device containing 6 mL Milli-Q water; an analogous procedure is used to prepare $50P_{42\%}PEG_{29\%}Ve_{29\%}$/Atropine (66.5 mg gel precursor, about 5 mg Atropine), and $50P_{33\%}PEG_{45\%}Ve_{22\%}$/Atropine sulfate (165.7 mg gel precursor, about 10 mg Atropine sulfate).

At predefined time points, 1 mL of solution is sampled from inside the dialysis bag to monitor drug release, followed by refilling with Milli-Q water to maintain a fixed overall volume in the devices at all times. The devices are kept under shaking (circulating in horizontal plane, 60 rpm), and sampled at the following intervals: 10 min, 30 min, 1 h, 3 h, 6 h, 12 h, 24 h, 48 h, 73 h, 100 h, 1 week, 2 weeks, and 3 weeks. The amount of drug released is quantified using high-performance liquid chromatography (HPLC, detecting UV absorption at 254 nm and using an Atlantis dC18 5 μm 4.6×100 mm column, solvent: mixture of 60/40 water/acetonitrile, flow rate: 1 mL/min).

TABLE 5

| | PEGMA-co-Vitamin E | | | Atropine | |
| --- | --- | --- | --- | --- | --- |
| Sample | mass (g) | PEG (g)[1] | Vitamin E (g) | Atropine (g) | Sulfate (g) |
| $50P_{42\%}PEG_{29\%}$Vitamin $E_{29\%}$/Atropine | 0.15 | 0.1 | 0.1 | 0.03 | — |
| $50P_{33\%}PEG_{45\%}$Vitamin $E_{22\%}$/Atropine | 0.15 | 0.2 | 0.1 | 0.03 | — |
| $50P_{33\%}PEG_{45\%}$Vitamin $E_{22\%}$/Atropine Sulfate | 0.15 | 0.2 | 0.1 | — | 0.03 |

In Vivo Injections and Histology Analysis.

To examine the in vivo toxicity of the materials, Sprague-Dawley rats and $C_{57}BL/6$ mice are used. Male Sprague-Dawley rats (about 500 g) are injected with 10 to 50 μL of sterile material precursor into the vitreous of the eye using a 10 μL 700 series Hamilton syringe and a 30 gauge needle. Animals are induced with isofluorane and anaesthetized with a ketamine xylazine mixture.

The injection and in situ gelation process is monitored and recorded using a dissecting microscope and the Micron IV fundus camera. The rats are sacrificed 4 h after injection, after which the eyes are enucleated. The eye samples are fixed in 4% neutral buffered formalin (NBF) for 24 h, followed by standard histological processing and embedding into paraffin wax.

Whole eyes are processed into 5 µm sections along the sagittal plane. Tissue samples are stained using hematoxylin and eosin (H&E). The resulting cross sections are examined using a light microscope.

The long-term stability of the hydrogel materials is studied via a subcutaneous injection study. Male mice (about 25 g) are injected with 100 µL of $50P_{42\%}PEG_{29\%}Ve_{29\%}$ precursor solution subcutaneously in the flank using a 25 gauge syringe. After 15 days, mice are sacrificed and the injection site is explanted. Both cryosectioning and paraffin histology are performed in an attempt to preserve the hydrogel, which is miscible in the organic solvents needed with wax. The samples are fixed in 4% NBF as above for 24 h, cleared in ethanol, then either processed for paraffin embedding or snap-frozen in optimal cutting temperature (OCT) compound in a bath of isopentane cooled by liquid nitrogen. Sections are created using a microtome or cryostat as required and stained with H&E as described above.

Example 3: Preparation of a Nanogel of Methylcellulose Hydrophobized with N-Tert-Butylacrylamide for Ocular Drug Delivery A self-assembling nanogel of 140 nm is prepared by grafting side chains of poly(N-tert-butylacrylamide) (PNtBAm) on methylcellulose via cerium ammonium nitrate. Successful grafting of PNtBAm onto methylcellulose (MC) is confirmed by both NMR and ATR (attenuated total reflectance). Synthesized molecules (MC-g-PNtBAm) display self-assembly in water, which is driven by hydrophobic interaction of the grafted side chains creating colloid solutions. Materials are synthesized by changing feed ratios of acid, initiator, and monomer to control the degree of hydrophobic modification. The nanogels are tested for different degrees of grafting. Viability studies are performed with HCE (human corneal) cells to confirm the biocompatibility of poly(N-tert-butylacrylamide) grafted methylcellulose nanogels. Dexamethasone entrapping is tested to assess drug retention in the system and release.

Example 4: Preparation of Injectable, Resorbable, Thermoresponsive Copolymer Scaffolds Copolymers with varying N-isopropylacrylamide, acrylamide (AAm), acrylic acid N-hydroxysuccinimide, and (r)-α-acryloyloxy-β,β-dimethyl-γ-butyrolactone (DBA) are synthesized by RAFT (reversible addition-fragmentation chain-transfer) polymerization to develop injectable, resorbable, and thermoresponsive copolymer scaffolds. Upon injection into physiological conditions, the copolymers undergo a temperature induced gelation to form a drug releasing scaffold. Modification of the copolymer's AAm/DBA ratio and molecular weight affords control over the scaffold's physical properties and subsequent drug release profile. Hydrolytic DBA ring-opening enables redissolution of the copolymers for clearance from the body.

Example 5: Preparation of Hydrophobically-Modified PVP Hydrogel

Hydrophobic modification of a hydrogel is achieved via random copolymerization of N-vinylpyrrolidone with N-vinylformamide, the latter of which is hydrolyzed to expose a desired degree of reactive amine groups permitting grafting of alkyl chlorides of varying alkyl chain lengths. The resulting materials form highly shear-responsive physical hydrogels, exhibiting tunable shear thinning over 4-5 decades of viscosity from infinite shear to zero shear conditions that facilitate lubrication upon blinking and/or facile injection or drop-based delivery to the anterior or posterior segments of the eye.

The viscosity of the hydrogel is changed by tuning the length of the hydrophobe, with $C_{18}$-grafted materials exhibiting prolonged thickening over several weeks to form extremely stiff hydrogels and shorter grafts equilibrating faster, but forming weaker gels.

Cytotoxicity of the polymers is tested in HCEC and retinal pigment epithelial cells. In vivo assessments of the polymers are performed in rabbits via intravitreal injection of the polymers.

Example 6. Synthesis and Characterization of Poly(NIPAAm-NAS-AA-DBA) (pNNAD) Copolymers pNNAD copolymers are synthesized via radical polymerization in a 100 mL one-necked round bottom flask. NIPAAm (3.84 g, 33.95 mmol), N-acrylic acid N-hydroxysuccinimide (NAS, 0.287 g, 1.69 mmol), acrylic acid (AA, 0.244 g, 3.39 mmol), (R)-α-acryloyloxy-β-β-dimethyl-γ-butyrolactone (DBA, 0.626 g, 3.39 mmol), and benzoyl peroxide (BPO, 0.103 g, 0.42 mmol, 1 mol % relative to monomer content) are dissolved in 45 mL 1,4-dioxane to form a 10% weight % monomer solution (90:4:8:8 molar feed ratio of NIPAAm:NAS:AA:DBA). Dry nitrogen is bubbled through the solution for 15 minutes and the flask is sealed and heated to 70° C. for 24 hours in a temperature-controlled oil bath with constant stirring to provide uniform mixing. Following the reaction, the polymer solution is cooled to room temperature and isolated by precipitation in anhydrous ethyl ether (1 L). The resulting polymer, denoted pNNAD-8 (the number represents the copolymer DBA content) is dried overnight in a vacuum oven at 50° C. The copolymer is further purified by repeated precipitation from tetrahydrofuran (THF) into anhydrous ethyl ether. The purified copolymer is then dried to a constant weight in a vacuum oven at 50° C.

Copolymerization and purification of pNNAD copolymers with NIPAAm:NAS:AA:DBA molar feed ratios of 80:4:12:4 (pNNAD-4) and 80:4:4:12 (pNNAD-12) are prepared in a similar fashion to pNNAD-8.

For in vitro and in vivo testing purposes, pNNAD copolymers are further purified by extensive dialysis in deionized water at 4° C. using cellulose tubing possessing a 3.5 kg/mol MW cut-off (MWCO). The resulting copolymer solutions are freeze-dried and stored frozen at −20° C. until use.

Cell adhesive RGDS peptides are grafted onto the pNNAD copolymers via a conjugation reaction between amine groups present on the arginine residues and copolymer NAS groups. Briefly, pNNAD-12 (0.9017 g, 0.289 mmol NAS) is dissolved in 40 mL PBS (pH 7.4) in a 100 mL one neck round bottom flask. RGDS (80 mg, 0.184 mmol) is dissolved in 5 mL PBS (pH 7.4), and added to the polymer solution under stirring. The reaction mixture is allowed to proceed for 24 hours at 4° C. under constant stirring. The RGDS grafted copolymer, pNNAD-12-RGDS, is extensively dialyzed against deionized water at 4° C. using cellulose membranes with a 3.5 kg/mol MWCO. The resulting polymer solution is freeze dried, and stored at −20° C.

A RGDS grafting density on the pNNAD-12 copolymer of 1.7 mol % of the total monomer content is expected by $^1$H NMR.

RGDS is grafted onto the pNNAD-4 copolymer in a similar fashion. pNNAD-4 (0.899 g, 0.313 mmol NAS), and RGDS (81 mg, 0.186 mmol) are dissolved in 45 mL PBS (pH 7.4) and stirred continuously at 4° C. for 24 hours. The resulting pNNAD-4-RGDS copolymer is dialyzed extensively against deionized water at 4° C. using cellulose membranes with a 3.5 kg/mol MWCO and freeze-dried and stored at −20° C. A RGDS grafting density on the pNNAD-4 copolymer of 2 mol % of the total monomer content is expected to be confirmed by $^1$H NMR.

Material Characterization of pNNAD Copolymers.

pNNAD copolymer structures are characterized using FT-IR spectroscopy. Copolymer compositions and extent of RGDS grafting are determined by $^1$H NMR with DMSO-d6 as a solvent. Copolymer molecular weights are determined by aqueous phase gel permeation chromatography.

Low Critical Solution Temperature Characterization of pNNAD Copolymers.

Characterization of copolymer low critical solution temperature is carried out using differential scanning calorimetry and UV/vis spectrophotometry. Glass transition temperatures of intact and degraded copolymers are measured by direct scanning calorimetry.

Water Content of pNNAD Copolymers.

The water content of pNNAD copolymers is assessed gravimetrically by dissolving samples, inducing hydrogel gelation, weighing hydrated hydrogels to obtain wet mass, drying samples to constant weight, and assessing hydrogel water content with the following equation:

$$\text{Water Content (\%)} = \frac{(m_w - m_d)}{m_d} \times 100 \qquad \text{(Equation 1)}$$

where $m_w$ is the hydrogel's wet mass and $m_d$ is the hydrogel's dry mass.

Degradation by Accelerated hydrolysis of pNNAD copolymers.

Accelerated hydrolysis, both complete and partial, of pNNAD copolymers is performed by preparing solutions of each polymer in de-ionized water (20% w/v) in a 20 mL glass vial. The pH of the solutions is adjusted to 10.25 (with either 0.1 or 1 M NaOH) and then the solutions are placed in an oven at 70° C. The pH of the polymer solution is adjusted to 10.5 daily. Complete degradation of the copolymers is expected in 21 days, and the pH of the solution remains constant. Fully degraded samples are maintained at pH 10.5 for an additional 3 days (24 in total) and are collected by dialysis with 3.5 kg/mol MWCO filter and freeze-drying. During the degradation process, aliquots are collected periodically, dialyzed, and freeze-dried. Collected aliquots are used to determine the composition of the partially degraded polymers. Changes in copolymer structure as a function of accelerated degradation are determined using FT-IR spectroscopy. The sequential degradation mechanism of pNNAD copolymers are also characterized by $^1$H NMR.

pNNAD Copolymer Degradation in Heated PBS.

Copolymers are dissolved in PBS to concentrations of 20% in pre-weighed 2 mL plastic tubes. Samples are dissolved at 4° C. for 24 hours and placed in a 37° C. oven and allowed to gel. After 5, 20, 40, 65, and 130 days of incubation at 37° C., the supernatant is aspirated and samples are carefully rinsed with prewarmed water to remove any soluble pNNAD and PBS residue. The rinsed samples are then carefully blotted dry to remove any residual surface water. A resulting polymer wet mass ($m_{wf}$) is obtained. A final dry polymer mass ($m_{df}$) is obtained by drying samples to a constant weight in a 65° C. oven. Polymer degradation is determined with the following equation:

$$\text{Mass Remaining (\%)} = \frac{(m_{df})}{m_{di}} \times 100 \qquad \text{(Equation 2)}$$

where $d_i$ denotes the mass of the initial dry sample. Water content of the final copolymer is quantified according to Equation 1.

pNNAD Copolymer Morphology.

Physical changes in polymer morphology as a function of degradation are visualized using scanning electron microscopy.

Dexamethasone Release from pNNAD Copolymers.

To model the release profile of relevant drugs embedded in pNNAD copolymers, pNNAD copolymers are dissolved at 4° C. to concentrations of 20% w/v in a 10% w/v PBS/dexamethasone solution. Dexamethasone-infused copolymer solutions are placed in a 37° C. oven for two hours to drive scaffold formation and dexamethasone entrapment. Supernatant is collected, and the scaffolds are washed and placed in fresh PBS. Aliquots of PBS are taken at time points of 0.5, 1, 2, 3, 4, 5, and 6 hours. The amount of dexamethasone, which serves as a model for relevant drugs, released from scaffolds is determined by analyzing aliquots using high performance liquid chromatography.

Effect of pNNAD Copolymers on In Vitro Cell Viability.

To determine the effect of copolymers on cell viability, assays are performed with human retinal pigment epithelial cells (RPE) cells. RPE cells are seeded in a 48-well tissue culture polystyrene plate at a density of 50,000 cells per well in DMEM-F12 culture medium supplemented with fetal bovine serum (FBS) (6.25% final concentration), glutamate (1% final concentration,) penicillin-streptomycin (1% final concentration), and sodium bicarbonate (0.8% final concentration). Cells are incubated under these conditions for 2 hours to allow for cell attachment to the plate. After incubation for 2 hours, the cell supernatant is replaced with fresh media containing 10 mg of dissolved copolymer that has previously undergone dialysis with cellulose tubing, freeze drying, and treatment with a PBS-penicillin-streptomycin solution (3:1 v/v). Partially degraded, fully hydrolyzed and intact pNNAD-4, pNNAD-8, and pNNAD-12 copolymers are tested and polymer free media is used as a control. Viability is assessed after 96 hours using a Trypan Blue assay, and scaffold impact on cell viability is analyzed using a one-factor analysis of variance.

Subcutaneous Injection of pNNAD Copolymers into SKH1-E Mice.

In vivo experiments are performed to determine whether the copolymers cause an adverse response in animals. Copolymer samples are sterilized with ethylene oxide gas (EO) following extensive dialysis and freeze drying. Copolymers are exposed to a 100% atmosphere of EO for 2 hours at 57° C. Copolymers pNNAD-4, pNNAD-12, pNNAD-4-RGDS, and pNNAD-12-RGDS are dissolved in medical grade saline to concentrations of 15% w/v in 10 mL aliquots. Polymer samples, syringes, and the injection site are pre-cooled with ice to prevent premature polymer gelation, and polymer samples are injected subcutaneously into hairless SKH1-E mice using a 25 gauge needle. Mice are sacrificed 20 or 40 days later and the tissue at the injection site is fixed in a 4% formalin solution, embedded in paraffin, sliced into 4 micron sections, and stained with hematoxylin and eosin (H&E). H&E sections are observed with light microscopy to determine whether copolymer injections cause an adverse response in the mice.

Proposed Mechanism of Ophthalmic Drug Release from pNNAD Copolymers.

To demonstrate a proposed mechanism of ophthalmic drug release, a PNIPAAm solution is infused with Toluidine Blue, and the solution is injected into a pre-heated aqueous solution. Gel formation of the solution occurs rapidly following injection, entrapping the infused toluidine dye, which acts as a representative drug for visualization purposes. The toluidine solution is then slowly released from the pNNAD copolymer into the surrounding environment. The majority of the toluidine reservoir is depleted, and hydrolytic opening of the DBA lactone ring induces copolymer re-hydration. Copolymer rehydration can lead to clearance from the eye through the anterior ocular elimination route. The copolymer then enters the systemic circulation and is cleared from the body via the kidneys.

Example 7. Preparation and Characterization of a Hyaluronic Acid (HA) Retaining Polymer Polyhydroxyethyl methacrylate (pHEMA) membranes are prepared as follows. 2-hydroxyethyl methacrylate (HEMA) monomer is purified to remove the 4-methoxyphenol (MEHQ) polymerization inhibitor by passing the monomer through a column packed with Aldrich inhibitor removers. HEMA and 1% by weight ethylene glycol dimethacrylate (EGDMA) are mixed. To this mix, an equal amount of water by weight is then added and the mixtures stirred. 1% by weight benzoyl peroxide, dissolved in a small amount of tetrahydrofuran (THF) in a 1.5 mL vial is then added and rapidly and mixed to prevent the formation of a precipitate. This mixture is then poured into custom-made molds, placed in a 400 watt UV chamber, and cured for 25 minutes. Molds are transferred to an oven at 50° C. for 18 hours to ensure that all monomer is fully reacted. Polymeric materials are then removed from the molds and placed in water for one to two days to ensure complete swelling prior to cutting, and to remove any unreacted monomer in the samples. Samples of pHEMA are cut to the desired size, placed in a 48-well plate, and dried at 40° C. overnight.

Hyaluronic Acid Loading of Hydrogels.

Hydrogels are loaded with HA by preparing HA (molecular weight 30 kDa, 169 kDa, or 900 kDa) solutions (5 g/L) in 30% ethanol and 70% water. Dried hydrogel disks are placed in excess HA containing solutions in 48-well plates, sealed, and stored for a minimum of four days at 4° C. to ensure maximum HA uptake.

Hyaluronic Acid Crosslinking.

To entrap physically HA into the pHEMA structure of hydrogels, crosslinking steps are performed using 1-ethyl-3-(3-dimethylaminopropyl)-carbodiimide (EDC) as a facilitating agent. Diaminobutane-4 (DAB-4) generation 1 dendrimer is used as a crosslinking agent. pHEMA containing crosslinked HA is prepared by swelling pHEMA membranes in 0.2 mL of a solution of HA (5 g/L) and DAB-4 generation 1 dendrimer (5 g/L) in 30% ethanol/70% water for a minimum of 4 days at 4° C. to ensure complete uptake. Following loading, samples are placed in a solution containing approximately 1% by weight EDC in water for a period of 24 hours at room temperature to result in cross-linking of the loaded HA. This step is followed by release of the unreacted HA and dendrimer by soaking in water for a minimum of two days prior to characterization. Control materials are prepared in the same manner with no EDC present in the reaction solution.

Equilibrium Water Content (EWC).

To determine the EWC of the prepared hydrogels, hydrogel samples are dried at 40° C. for a period of 2 days and weighed. Samples are then placed in water for a period of a week. Samples are then removed from water and excess water is removed by blotting with a wipe. Samples are then weighed and the EWC of each is calculated using the following equation:

$$EWC = \frac{(\text{Hydrated weight} - \text{Dry weight})}{\text{Hydrated weight}} \quad \text{(Equation 3)}$$

HEMA and HEMA-HA Sample Morphology.

The morphology of HEMA and HEMA-containing cross-linked HA samples is assessed with transmission electron microscopy.

Ha Release.

HA release studies are performed to determine the rate at which uncrosslinked HA present in a hydrogel can release into a surrounding aqueous fluid. In such studies, surfaces are loaded with high molecular weight, fluorescently labeled HA. The HA is not crosslinked. Loaded samples are placed into PBS buffer at physiologic temperature and aliquots of the PBS buffer are taken at regular intervals. Samples are assayed for fluorescence using a fluorimeter, with the presence of fluorescence indicating the release of HA from the samples. The amount of HA released from crosslinked HA is also examined to determine whether the cross-linked HA is releasable.

Optical Transparency of HEMA/HA Materials.

Transparency of HA modified and HA releasing materials is measured by UV spectrophotometry in a wavelength range between 400 and 700 nm.

Surface Hydrophilicity as Measured by Water Contact Angles.

Information about the surface hydrophilicity and hydrophobicity of hydrogel samples is determined through the measurement of sessile drop advancing and receding contact angles. The measurement of sessile drop advancing and receding contact angles is determined by placing samples on glass slides and drying at 37° C. overnight. Water contact angles are measured with a drop volume of no greater than 3 µL using a goniometer.

Sample Surface Characterization.

The surfaces of samples are dried and analyzed via atomic force microscopy in surface tapping mode to assess whether the incorporation of HA into pHEMA hydrogels affects surface roughness.

Tensile Strength Testing.

To determine the mechanical properties of hydrogel samples, samples with hydrated dimensions of 4 cm by 1.5 cm are prepared. Hydrated samples are loaded at room temperature using an automated mechanical testing system with a 50 Newton load. Tensile stress and strain are measured using a crosshead speed of 5 mm/min. The top and bottom of each sample are wrapped in tape to protect the samples during clamping.

Glass Transition Temperature of Hydrogels.

To assess changes that may have occurred in the thermal properties of hydrogels as a result of the incorporation and crosslinking of HA, 2-10 mg of freeze-dried samples of pHEMA, pHEMA/35 kDa un/crosslinked HA and pHEMA/169 kDa un/crosslinked HA are placed in a hermetically sealed pan and heated to 300° C. at a rate of 15° C./minute. Differential scanning calorimetry is used to measure the glass transition temperature of the samples.

Protein Adsorption to HA Modified Hydrogels.

Proteins are radiolabeled with $Na^{125}I$ or $Na^{131}I$ using an iodine monochloride method. Unbound $^{125}I$ and $^{131}I$ are removed by passing the labeled protein sample through a 3 mL syringe packed with AG 1-X4 (100-200 dry mesh in chloride form). Free iodide is measured by trichloroacetic acid precipitation of the protein.

A simulated tear solution with the composition shown in TABLE 6 below is prepared in PBS. In all studies, two radiolabeled proteins are used, one labeled using $^{125}I$ and one labeled with $^{131}I$, Depending on the protein in question the simulated tear solution contains between 3-8% (w/w) radiolabeled protein.

TABLE 6

Model tear solution and amount of radiolabeled protein

| Protein | Concentration (mg/mL) | % Radiolabeled Protein |
|---|---|---|
| Lysozyme | 1.9 | 8 |
| Albumin | 0.2 | 6 |
| IgG | 1.7 | 3 |
| B-lactoglobulin | 1.6 | |

Hydrogel samples are equilibrated in PBS, wiped dry, and placed in 24-well plates. Artificial tear solutions (150 µL) are added to the sample wells and samples are incubated for two hours at room temperature. A 3-5-minute rinse of samples follows. To quantify protein adsorption on HA-modified hydrogels, sample surfaces are counted for radioactivity using an automatic gamma counter, and adsorbed amounts of protein are calculated using background-corrected surface counts relative to the solution count for the individual protein solution.

Example 8: Preparation and Characterization of a HA-Modified Silicone/HEMA Copolymer Similar experiments as those discussed in EXAMPLE 7 above are performed with HA modified silicone/HEMA copolymer. Methacryloxy propyl tris (trimethylsiloxy) silane (TRIS) monomer and HEMA monomer are purified to remove the MEHQ polymerization inhibitor by passing the monomer through a column packed with Aldrich inhibitor removers. HEMA, TRIS and 5% by weight EGDMA are mixed. Subsequently, 0.5% by weight IRGACURE is added and mixed thoroughly. The solution is poured into a custom mold, placed in a UV chamber, and allowed to cure for 25 minutes. The surfaces are then placed in an oven at 50° C. overnight to ensure complete reaction of the monomer. Following polymerization, the materials are removed from the molds and placed in water for over two days to remove any unreacted monomer from the samples. Samples are cut to the desired size, and placed in a 48 well plate and dried at 40° C. overnight.

Hyaluronic Acid Loading and Incorporation.

To incorporate HA, solutions containing HA (5 g/L) and diaminobutane-4 (DAB-4) generation 1 dendrimer (5 g/L) are prepared in 30% ethanol/70% water. Two molecular weights of HA are studied, 35 kDa and 169 kDa. Dried hydrogel disks are placed in an excess amount of the HA-containing solutions in 48-well plates, sealed using parafilm, and stored for a minimum of four days at 4° C. to ensure a maximum uptake of HA.

Following HA loading a solution containing approximately 1% by weight EDC in water is prepared and the loaded samples are placed in excess of this reagent for a period of 24 hours for crosslinking of the loaded HA. Unreacted HA and dendrimer is then released by soaking in water for a minimum of two days prior to characterization.

Surface Hydrophilicity as Measured by Water Contact Angles.

Information about the surface hydrophilicity and hydrophobicity of hydrogel samples is determined through the measurement of sessile drop advancing and receding contact angles. The measurement of sessile drop advancing and receding contact angles is determined by placing samples on glass slides and drying at 37° C. overnight. Water contact angles are measured with a drop volume of no greater than 3 µL using a goniometer.

Glass Transition Temperature of Hydrogels.

Changes in the thermal properties of hydrogels as a result of the incorporation and crosslinking of HA are determined by placing 2-10 mg of freeze-dried samples of TRIS/pHEMA, TRIS/pHEMA/35 kDa crosslinked HA and TRIS/pHEMA/169 kDa crosslinked HA in a hermetically sealed pan and heating to 300° C. at a rate of 15° C./minute. Differential scanning calorimetry is used to measure the glass transition temperature of the samples.

Protein Adsorption to Modified Materials.

To quantify protein adsorption to modified materials, lysozyme is radiolabeled with Na $^{125}I$ using the iodine monochloride method. Unbound $^{125}I$ is removed by passing the labeled protein solution through a 3 mL syringe packed with AG 1-X4 (100-200 dry mesh in chloride form). Free iodide is measured by trichloroacetic acid precipitation of the protein. A simulated tear solution, the composition of which is shown in TABLE 6 above, is prepared in PBS using 8% radiolabeled lysozyme.

Samples are equilibrated in PBS, wiped dry and placed in 24-well plates. Artificial tear solutions (150 µL) are added to the sample wells and samples are incubated for two hours at room temperature. A 3-5 minute rinse of samples follows. Sample surfaces are counted for radioactivity using an automatic gamma counter and adsorbed amounts of protein are calculated using background-corrected surface counts relative to the solution count for the individual protein solution.

Example 9: Synthesis and Characterization of pLA-b-p(MAA-PBA) Copolymer Micelles pLA-b-p(MAA-PBA) Copolymer Synthesis.

pLA-b-p(MAA-PBA) (LMP) copolymers are synthesized by RAFT polymerization. Methacrylic acid (MAA; 192.9 mg, 2.24 mmol), phenylboronic acid (PBA) (107.1 mg, 0.56 mmol), poly(L-lactide) 4-cyano-4-[(dodecyl sulfanylthiocarbonyl)sulfanyl] pentoate (pLA-CDP; 200.0 mg, 0.04 mmol), and AIBN (1.10 mg, 0.01 mmol) are dissolved in 5 mL of 90:10 1,4-dioxane:water to form a 10% solution. The solution is degassed by performing three freeze-pump-thaw cycles followed by replacement of the atmosphere with dry nitrogen. The flask is heated to 70° C. for 24 hours under constant stirring. This copolymer, denoted LMP-20 (20 wt. % PBA in the poly(MAA-co-PBA) block), is isolated by precipitation into 10 times excess of cold anhydrous diethyl ether and further purified by repeated precipitation into diethyl ether from tetrahydrofuran. The copolymer is dried in a vacuum oven at 50° C. for 24 hours until constant weight has been achieved.

pLA-b-p(MAA-PBA) Copolymer Characterization.

LMP copolymer composition and molecular weight are determined using $^1$H NMR. LMP polymerization kinetics are studied with experimental methods to determine the distribution of PBA within MAA-PBA block and controlled nature of polymerization.

Micelle Formation and Characterization.

Micelles are formed by the precipitation method. 20 mg of copolymer is dissolved in 2 mL acetone. The copolymer solution is added drop-wise to 6 mL of purified water under constant stirring. The acetone/water solutions are then allowed to stir uncovered at room temperature for 48 hours to evaporate the acetone before further characterization. Micelle size is determined using nanoparticle tracking analysis. Micelle solutions are purified in water and diluted to 0.05 mg/mL before measurement in pH 7.4 PBS. Micelle stability is assessed using Zeta potential in pH 7.4 PBS with 10 mM NaCl.

The critical micelle concentration (CMC) is determined using the pyrene fluorescent probe method. A predetermined amount of pyrene is dissolved in acetone and added to 2 mL vials and allowed to evaporate. Micelle solutions ranging from 10 mg/mL to $10^{-5}$ mg/mL are added and incubated for 24 hours at room temperature, resulting in final pyrene concentrations of $6.0 \times 10^1$ mol/L. Fluorescence is measured using a fluorimeter. The excitation spectrum is measured after an excitation wavelength of 340 nm. The CMC is determined by plotting the intensity ratio of peaks at 373 nm to those at 383 nm against the logarithm of concentration. The emission and excitation bandwidth for all measurements is 5 nm.

Micelle morphology and size are assessed via transmission electron microscopy.

Mucoadhesion by Surface Plasmon Resonance.

Mucoadhesion is determined using surface plasmon resonance. Surface plasmon resonance 102-AU gold sensors are cleaned using piranha (3:1 94% sulfuric acid: hydrogen peroxide), rinsed extensively with purified water, and dried under a stream of nitrogen. These sensors are then incubated in 100 μL of 100 μg/mL bovine submaxillary gland mucin for 24 hours at 20° C. and then rinsed with purified water to remove unbound mucin. Surface plasmon resonance measurements are conducted by flowing simulated tear fluid (STF; 23.1 mM KCl, 20.0 mM NaHCO$_3$, 1 mM CaCl$_2$.2H$_2$O, 113.5 mM NaCl) for 10 minutes to achieve a stable baseline. The solution is then changed to a 1 mg/mL solution of chitosan or LMP micelles for 50 minutes. The solution is then changed back to simulated tear fluid to assess mucoadhesion stability. All measurements are conducted at a flowrate of 50 μL/minute, a temperature of 22° C., and a fixed angle scan of 65.4°. Chitosan is used as a positive control of mucoadhesion for comparison.

Cyclosporine A (CycA) Release.

CycA is entrapped in LMC micelles by dissolving both components in acetone followed by drop-wise addition into purified water at a ratio of 20 mg copolymer to 3 mg CycA. Acetone is evaporated for 24 hours under constant stirring, and drug laded micelles are filtered. Filtrate is collected and micelles are added to simulated tear fluid. At specified time points, aliquots of the simulated tear fluid are removed, and CycA release from micelles is determined using HPLC.

In Vitro Cell Viability.

The effect of copolymers on cell viability is determined via in vitro experiments. Copolymers are extensively dialyzed in 2:1 acetone:water solutions against 3.5 kDa MWCO dialysis tubing, and then are freeze dried. 50 mg of copolymer is then dissolved in 1 mL of acetone and added dropwise under constant stirring to 2.5 mL of sterile water. The acetone is allowed to evaporate for 48 hours under constant stirring, whereby concentrated PBS and penicillin/streptomycin are added to final concentrations of 0.1 M and 1% (v/v), respectively.

Human corneal epithelial cells (HCECs) are cultured in keratinocyte serum-free media (KSFM) supplemented with bovine pituitary extract (BPE, 0.05 mg/mL) and epidermal growth factor (EGF, 0.005 mg/mL). HCECs are seeded in 96-well plates at densities of 5,000 cells/well and incubated in a temperature-controlled CO$_2$ incubator (37° C., 5% CO$_2$, 95% air, 100% humidity). After 24 hours of growth, the media is replaced with 150 μL of KSFM and either 50 μL of PBS, 20 mg/mL LMP micelles, or 4 mg/mL micelles for final LMP micelle concentration of 0, 5, and 1 mg/mL. The plates are incubated at 37° C. and cell viability is assessed with a MTT assay and a CalAM/EthD-1 assay after 24 and 72 hours.

Example 10. In Vivo Mucoadhesion Study

An animal study is performed to confirm that micelles produced by the processes discussed in EXAMPLE 9 above exhibit mucoadhesion in an in vivo setting. Micelles containing 20% PBA are modified covalently with 5-aminofluorescein (FA) using carbodiimide-mediated coupling. Copolymer is dissolved in dry DMSO in a sealed flask containing a stir bar and covered in aluminum foil to avoid exposure to light. To this solution, 5-aminofluorescein, N,N'-Dicyclohexylcarbodiimide, and 4-Dimethylaminopyridine are added to achieve molar ratios of 100:30:110:10 for MAA groups:FA:DCC:DMAP, respectively. The flask is sealed with a rubber stopper and left to stir for 24 hours. After 24 hours of reaction, the solution is dialyzed until sufficiently pure. A single 50 μL drop with 5 mg/mL of micelle is dropped into the eye of a healthy rat. Fluorescein staining and imaging are then performed after 1 hour to confirm ocular surface binding of PBA containing micelles in an in vivo environment.

Example 11: Preclinical DED Model

The preclinical BAC-induced DED rat model is used to determine whether the micelles described in EXAMPLE 9 above are suitable for use in vivo. The effect of micelles without drug on the BAC-induced DED model is determined using the Schrimer's test, in which paper test strips with graded markings wick up tear film and determine tear volume. This method is modified for rats by cutting strips designed for humans to ⅓ of the width to determine how micelle treatment affects tear volume by comparing rats treated with micelles to untreated controls. Similar testing is also performed in non-DED rats. Tear osmolarity is assessed by collecting tears and using an osmometer. Disease severity is assessed using the Draize test and a fluorometric test in which fluorescein stains damaged corneal tissues thereby making the tissues more visible under blue light to facilitate viewing and scoring by an ophthalmologist.

Example 12: Methacrylation of HA

To Methacrylate HA, HA is Dissolved at 1 wt % in Deionized Water (diH$_2$O). This solution is reacted with a 20-fold molar excess of methacrylic anhydride over a period of about 48 hours. The solution is constantly stirred and kept in an ice bath to maintain a temperature of about 4° C. The pH of the solution is monitored and adjusted to about 8 through the addition of 5 M sodium hydroxide. After the 48-hour reaction period, the solution is removed from the ice bath and dialyzed against diH$_2$O using a 3500 MWCO membrane for another 48 hours, lyophilized, and stored frozen in the native powder form. $^1$H-NMR analysis is used to confirm methacrylation.

Hydrogel Preparation.

To produce methacrylated HA-hydrogels, methacrylated HA is dissolved at various weight percentages in PBS prior to polymerization. These pre-polymer solutions are then mixed with a photoinitiator solution consisting of 33 wt % 2,2-dimethoxy-2-phenylacetophenone (DMPA) dissolved in methanol at a ratio of 1 wt % initiator to pre-polymer solution. This pre-polymer and initiator mixture is then injected into molds of various sizes using a pipette and placed into a UV oven where photopolymerization occurs upon exposure to 12.5 mW of 365 nm UV light over a period of about 5 minutes.

Hydrogel Water Content Studies.

Hydrogel water content for methacrylated HA samples is defined as the ratio of the weight of the polymer after complete dehydration to the weight of the polymer immediately after photopolymerization. To determine hydrogel water content of methacrylated HA samples, hydrogel disks are polymerized in ⅜ inch diameter plastic molds, removed after polymerization and immediately weighed on a plastic weighing dish. Gels are then dehydrated on the weighing dish in a 70° C. oven for 120 minutes and subsequently weighed again.

Swelling Ratio.

The swelling ratio of hydrogels is defined as the ratio of the weight of the hydrogels after being swollen in PBS for 24 hours at 37° C. to the weight of the hydrogels after being fully dehydrated. To determine the swelling ratio, hydrogel disks are polymerized in ⅜ inch diameter plastic molds, removed after polymerization, and immediately weighed on a plastic weighing dish. Gels are then dehydrated on the weighing dish in a 70° C. oven for 120 minutes and subsequently weighed. Samples are then removed from the weighing dish and placed in 48-well plates, where 1 mL of diH$_2$O is added. The 48-well plates are placed in an incubator for 24 hours. Average mesh size and effective cross-linking density is also calculated.

Degradation.

To assess the stability of hydrogel disks, polymer disks ⅜ inch in diameter are degraded in solutions containing 10 or 100 U of hyaluronidase per mL of PBS. Samples are checked every 24 hours, and the hyaluronidase solution is replaced every 48 hours throughout the study. Samples are kept at 37° C. The time for complete degradation of the hydrogel disks is determined to be the point at which no piece of the hydrogel is visible within the plate well after the hyaluronidase solution is removed.

Optical Transparency and Refractive Index.

To create hydrogels that mimic the transmission curve of the human lens, various amounts of 2-hydroxy-4-methoxy-benzophenone-5-sulfonic acid, a common UV absorbing molecule, are added to polymerized hydrogels. To do this, 10 wt % of 2-hydroxy-4-methoxybenzophenone-5-sulfonic acid is dissolved in diH$_2$O and mixed with methacrylated HA prepolymer solution. Light transmittance through hydrogels is determined via spectroscopy methods in a range of 250 to 1000 nm. The refractive index of methacrylated HA hydrogels is measured using a digital refractometer. Measurements of refractive index (the amount light waves change direction as they move through a medium) are made in bright and dark ambient light conditions.

Tensile Strength Testing.

To determine the mechanical properties of hydrogel samples, samples with dimensions of 5 cm by 2 cm are cut from hydrogel samples polymerized in a custom mold. The custom mold consists of a glass plate with glass microscope slides that act as spacers and a petri dish as a cover piece. All surfaces are covered in parafilm to reduce the tendency of the hydrogel to stick to the surface of the mold, and facilitate the removal of the hydrogel after photopolymerization. Samples are loaded onto a materials testing system and loaded with a 50 Newton load to assess tensile stress, strain, and elastic modulus.

Cell Adhesion Studies.

The interaction between the methacrylated HA hydrogels and cells present in the lens capsule are determined through in vitro studies. FHL-124 cells (a human lens epithelial cell line) are seeded onto the surface of the hydrogels and imaged at various time points. Cells are maintained in a 5% air/5% CO$_2$ humidified incubator at 37° C. Cells are cultured in 10% fetal bovine serum (FBS) in minimum essential medium (MEM) with penicillin-streptomycin and gentamicin. Cells between passages 10-15 are used.

Hydrogel disks are polymerized in the bottom of 96-well plates and sterilized with ethanol. Ethanol is removed from the surfaces, and the surfaces are rinsed with PBS before FHL-124 cells are seeded onto the surfaces of hydrogels using a bubble drop technique, where a small bubble of the cell suspension is placed on top of the material surface and cells are allowed to settle to the surface over a controlled time period. Cells are seeded at a density of 15,000 cells/cm$^2$ and immediately incubated for 120 minutes to facilitate cell attachment. 1 mL of media is added to each well after 120 minutes of incubation and cells are returned to the incubator for specified time periods. Cell viability is assessed using calcein AM and ethidium homodimer-1. Cell morphology is assessed via microscopy.

Example 13: Collagen-PNIPAAm In Situ-Formed Polymer Synthesis of Amine Terminated PNIPAAm Synthesis of PNIPAAm-Grafted-Collagen.

PNIPAAm-Grafted-Collagen is synthesized via EDC/NHS chemistry or UV photo crosslinking methods. In either method, N-isopropylacrylamide (NIPAAm) is purified by recrystallization from a toluene/hexane mixture. Amine terminated PNIPAAm is synthesized from NIPAAm via free radical polymerization using N,N'-Azobisisobutyronitrile (AIBN) as an initiator and cysteamine hydrodrochloride (AESH) as a chain transfer agent. NIPAAm, (88.37 mmol) and AESH (3.68 mmol) are dissolved in 20 mL dimethylformamide (DMF). Dry nitrogen is bubbled through the reaction mixture for thirty minutes prior to the addition of AIBN, previously recrystallized from methanol (1.22 mmol). Polymerization is allowed to proceed for 7 hours at 70° C. The polymerized product is precipitated into an excess of diethyl ether, where the product is collected by decanting and purified by repeatedly precipitating and dissolving in water. The product is then dialyzed using dialysis tubing having MWCO 5,000 for three days, freeze-dried, and stored at −20° C.

In the EDC/NHS chemistry method EDC)/N-hydroxysuccinimide (NHS) chemistry is used to graft linear chains of PNIPAAm onto a collagen backbone. EDC/NHS chemistry is used to generate covalent linkages between the carboxylic acid groups of aspartic acid (Asp) and glutamic acid (Glu) residues present in collagen with the amine functionalized end groups of the synthesized PNIPAAm. Briefly, 1 mL collagen (66 mg/mL) is acidified by thoroughly mixing with 100 µL HCl (1M). Amine-terminated PNIPAAm (660 mg) is dissolved in PBS (5 mL, pH 7.2) and is added to the mixture. The pH is adjusted to 6.5 with HCl. A 600 µL solution of EDC and NHS crosslinkers (45 mg and 25.8 mg) dissolved in PBS is added to the mixture, which is degassed and allowed to react at room temperature for 24 hours. The mixture is then dialyzed for three days at 4° C. using dialysis tubing having MWCO 50,000 to remove and EDC, NHS, and ungrafted PNIPAAm. The produced linear chains of PNIPAAm grafted along the length of the collagen backbone (PCol) is freeze dried and stored at −20° C.

During the course of UV photo crosslinking methods, a riboflavin-based crosslinker is used to generate covalent linkages between terminal amine groups of PNIPAAm and carboxylic acid side chains present in collagen. Collagen is acidified to pH 5.5 using 1M HCl. An excess of PNIPAAm is dissolved in PBS and mixed with collagen in a 2:1 (w/w) ratio. The UV crosslinker is added to the mixture in a 1:20 crosslinker to collagen (v/v) ratio. The mixture is placed in a UV oven (wavelength=365 nm, power=12.5 W/cm$^2$) for 15 minutes to allow crosslinking to occur. The resultant product is designated UV PCol.

Fibronectin Functionalized PNIPAAm Combined with Collagen.

Fibronectin functionalized PNIPAAm is combined with collagen by dissolving 10 mg of amine terminated PNIPAAm and 2 mg succinimidyl-4-(N-maleimidomethyl)cyclohexane-1-carboxylate (SMCC) in 1 mL PBS at a pH of 7.2. The reaction between the NHS ester end group of SMCC and the terminal amine group of PNIPAAm is allowed to proceed for 1 hour at room temperature with gentle mixing, generating a maleimide-functionalized PNIPAAm. Fibronectin (50 uL, 1 mg/ml) is added to the reaction in which exposed thiol groups present in fibronectin readily react with sulfhydryl end groups present on SMCC functionalized PNIPAAm. The reaction is allowed to proceed at room temperature for 24 hours with gentle mixing. The products, PNIPAAm-maleimide-fibronectin, are freeze dried. The dried PNIPAAm-maleimide-fibronectin is then dissolved in PBS and mixed 1:1 (w/w) with type I bovine collagen. Electrostatic interactions between like-charged regions of collagen and fibronectin act to hold the blended materials together, thus generating a PNIPAAm-fibronectin-collagen material, PColFn that contains no collagen crosslinking.

Phase Transition Characterization.

Phase transition properties of amine terminated PNIPAAm, collagen, PCol, PColFn, and UV PCol are analyzed by differential scanning calorimetry. Changes in transmittance associated with phase transition of PCol, PColFn, and UV PCol scaffolds are analyzed with a UV/VIS spectrophotometer after being dissolved in distilled water.

Gelling Time.

To determine the gelling time of PCol scaffolds, a vial containing 5 mg/mL PCol is placed in a water bath at various temperatures and the time required for the sample to reach the cloud point is recorded.

MW of Amine Terminated PNIPAAm.

The MW of amine terminated PNIPAAm is determined by gel permeation chromatography.

In vitro Cell Studies.

In vitro experiments are performed to analyze the impact of different scaffold components on retinal pigment epithelial viability. Human RPE cells are cultured in $CO_2$ incubators (37° C., 5% $CO_2$, 95% air, 100% humidity). DMEM-F12 culture medium is supplemented with FBS (6.25% final concentration), glutamate (1% final concentration), penicillin-streptomycin (1% final concentration), and sodium bicarbonate (0.8% final concentration).

To test the effects of scaffolds on pre-adhered cells, RPE cells are cultured in the presence of a variety of scaffolds including collagen, PNIPAAm, amine terminated PNIPAAm, PNIPAAm blended with collagen, and PCol. RPE cells are seeded in a treated 48-well plate at a density of 10,000 cells per well. The plate is placed in an incubator for 2 hours. Once cells adhere to the bottom of the wells, culture medium is removed and replaced with 1 mL of DMEM-F12 containing 20 mg of dissolved scaffold. Following addition of the scaffold to pre-adhered cells, the culture dishes are returned to the incubator, where PNIPAAm-based scaffolds gel in the supernatant of the plated cells. Cell viability is assessed after 96 hours by staining cultured cells with calcein AM, and EthD-1.

To assess the viability of cells when they are entrapped within scaffolds, 100,000 RPEs are suspended in a solution of PCol (20 mg/mL PCol in DMEM-F12 medium). The suspension is added to a treated 48-well plate. The plate is placed in an incubator where the PCol scaffolds gel, entrapping the cells within their matrix. Cell culture media is changed every 2-3 days. Cell viability is assessed 4 and 14 days after seeding using calcein AM, and EthD-1 stains.

Visualization of Scaffold Structure.

Scaffold structure is determined with electron microscopy methods. PNIPAAm, PCol, UV PCol, and PColFn scaffolds are swelled for 48 hours in distilled water at 37° C. Samples are rapidly frozen by immediate submersion in liquid nitrogen to preserve internal pore structure. After 48 hours samples are freeze dried and imaged via electron microscopy. Electron microscopy is also used to visualize RPE cells seeded within scaffolds.

Example 14: Preparation of a Photo-Responsive Drug Delivery System

PEG-Anthracene Crosslinker Synthesis.

To synthesize PEG-anthracene crosslinker O-(2-Aminoethyl)-O'-[2-(Boc-amino)ethyl]decaethylene glycol, a diamine terminated polyethylene glycol (PEG; MW<1000) with one terminal group blocked with tert-butoxycarbonyl (t-Boc) is used. The Boc-PEG amine is reacted with anthracene-9-carboxylic acid using EDC hydrochloride (1-ethyl-(dimethylaminopropyl)carbodiimide hydrochloride) in dry dichloromethane (DCM). The reaction proceeds with stirring for 24 hours at room temperature in a nitrogen atmosphere to ensure the protecting group is not prematurely removed. Unreacted EDC and by-products are removed from the reaction mixture by extraction using ethyl acetate and water. The blocking group from Boc-PEG anthracene is subsequently removed in DMC using trifluoroacetic acid (TFA) with the addition of triisopropyl silane (TIPS) as a scavenger. Final yields of dark versus light synthesis conditions are monitored since anthracene dimerization can aid or inhibit reactions.

Final purification is performed by drying the final reaction product and dissolving the product in water, followed by centrifugation and filtration through a 0.45 micron filter to remove water-insoluble residual deprotection products, anthracene, and non-deprotected PEG. Residual deprotected PEG that did not react with the anthracene-9-carboxylic acid in the first reaction, may still be present as an impurity. The diamine PEG may aid in the overall properties of subsequent gels. Diamine PEG can also be separated out using silica columns that are loaded using hexane/DCM and run using methanol/DCM.

PEG-Anthracene Solubility.

The solubility of anthracene into aqueous buffer is indicative of a chemical change, as anthracene is hydrophobic and insoluble unless bound to water soluble PEG. Control study comparisons with PEG and unbound anthracene-9-carboxylic acid are performed to ensure solubility is due to covalent reactions and not physical interactions.

Monitoring of PEG-Anthracene Synthesis and Dimerization.

PEG-anthracene formation is monitored via NMR. This formation can determine the degree of anthracene substitution, deprotection of the PEG, and deprotection of the second amine via Boc removal. The dimerization capability of the $NH_2$-PEG-anthracene in solution is monitored via spectrophotometric analysis with anthracene-9-carboxylic acid used as a comparison.

Synthesis of Photo-Crosslinked Hydrogel Systems.

To synthesize photo-crosslinked hydrogel systems, PEG-anthracene molecules are grafted to alginate polymer chains via carboxylic acid groups through amide bond formation. Low viscosity alginate solutions in morpholinoethanesulfonic acid (MES) buffer containing 0.5 M MES with 0.5 M NaCl (pH=6) are prepared resulting in a 6% w/v alginate. The solutions are mixed with a solution of EDC and NHS, resulting in a $NH_2$:EDC:NHS mixture with varying ratios. After 5 minutes of mixing, a PEG-anthracene solution in MES buffer is added to give a final concentration of about 3% (w/v) alginate. Illustrative parameters are shown below in TABLE 7. The reaction mixture is then placed between glass plates with a 1 mm glass spacer and allowed to react in the dark at room temperature for 24 hours or at 4° C. for 72 hours. Following the reaction, the gels are removed from the plates, and can be manipulated and handled due to the small amounts of diamine PEG present.

TABLE 7

| Mass Ratio | | |
|---|---|---|
| Anthracene | EDC | PEG |
| 1.92 | 1.34 | 1 |
| 0.14 | 1.34 | 1 |
| 2.3 | 1.34 | 1 |
| 2.3 | 1.608 | 1 |
| 0.64 | 0.45 | 1 |

Monitoring Gel Crosslinking.

The crosslinking of alginate via anthracene dimerization is determined using carbon-13 NMR.

Swelling Studies.

The swelling of hydrogels is monitored by cutting hydrogels into disks with a diameter of 0.5 cm. Dried gels are weighed and then soaked in water for specified time periods. The weight of the soaked gels is then determined. Comparisons of air-dried versus freeze-dried gels are performed. High-alginate containing gels with a final concentration of 6% (w/v) alginate are used to assess potential changes in swelling after various UV treatments.

Drug Release Studies.

The drug release properties of gels is modeled using Coomassie blue (0.5 mg/mL). Uptake into gels occurs over a 24 hour period. Prior to release studies, loaded gels are rinsed twice with PBS buffer (pH 7.4). Discs, 0.5 cm in diameter with a known weight, are placed in 1 mL PBS (pH 7.4) and placed into a shaking water bath at 37° C. At preset times, the gels are exposed to UV light treatments of either 365 nm or 245 nm. Releasates are sampled at regular intervals and analyzed using a microplate reader with a 595 nm filter.

Synthesis of Star-PEG-Anthracene Gels.

To synthesize star-PEG-anthracene gels, star-PEG-anthracene is dissolved into an initial amine-PEG-anthracene solution. The star-PEG-anthracene solution is then added into the reactive solution of alginate (6%) and EDC/NHS. As an initial starting point, the anthracene molar ratio of grafted PEG-anthracene to star-PEG-anthracene is 10:1. Spectrophotometry is used to verify star-PEG-anthracene reversible dimerization upon irradiation of solutions with 365 nm and 254 nm light. Drug delivery studies from gels as discussed above are used to assess changes in photosensitivity induced by the incorporation of star-PEG-anthracene to the alginate-PEG-anthracene gels.

Cytotoxicity Studies.

In vitro cell culture experiments are used to assess the biological compatibility of gels. Chinese hamster ovary (CHO) cells are grown with and without the presence of gels (first sterilized via an ethanol soak) in media containing 10% FBS in DMEM. Cell viability is monitored qualitatively via imaging and through staining with calcein AM, and EthD-1 stains.

Example 15: Illustrative Pharmaceutical Formulations for a Compound Described Herein A hydrogel pharmaceutical formulation comprising 15 mg/mL of Compound 1, PEG (0.1 g), Vitamin E (0.1) g is prepared.

A hydrogel pharmaceutical formulation comprising 15 mg/mL of Compound 1, PEG (0.2 g), Vitamin E (0.1) g is prepared.

A hydrogel pharmaceutical formulation comprising 15 mg/mL of Compound AA6 from TABLE 2, PEG (0.1 g), Vitamin E (0.1) g is prepared.

A hydrogel pharmaceutical formulation comprising 15 mg/mL of Compound AA6 from TABLE 2, PEG (0.2 g), Vitamin E (0.1) g is prepared.

A hydrogel pharmaceutical formulation comprising 15 mg/mL of Compound AA28 from TABLE 2, PEG (0.1 g), Vitamin E (0.1) g is prepared.

A hydrogel pharmaceutical formulation comprising 15 mg/mL of Compound AA28 from TABLE 2, PEG (0.2 g), Vitamin E (0.1) g is prepared.

A hydrogel pharmaceutical formulation comprising 15 mg/mL of Compound AA2 from TABLE 2, PEG (0.1 g), Vitamin E (0.1) g is prepared.

A hydrogel pharmaceutical formulation comprising 15 mg/mL of Compound AA2 from TABLE 2, PEG (0.2 g), Vitamin E (0.1) g is prepared.

A hydrogel pharmaceutical formulation comprising 15 mg/mL of Compound AA98 from TABLE 2, PEG (0.1 g), Vitamin E (0.1) g is prepared.

A hydrogel pharmaceutical formulation comprising 15 mg/mL of Compound AA98 from TABLE 2, PEG (0.2 g), Vitamin E (0.1) g is prepared.

A polymer system comprising 15 mg/mL of Compound 1 and pNNAD-4 (10 mg dissolved) is prepared, in which the polymer system undergoes a transition from a liquid to a gel upon exposure to a stimulus.

A polymer system comprising 15 mg/mL of Compound AA6 from TABLE 2 and pNNAD-4 (10 mg dissolved) is prepared, in which the polymer system undergoes a transition from a liquid to a gel upon exposure to a stimulus.

A polymer system comprising 15 mg/mL of Compound AA28 from TABLE 2 and pNNAD-4 (10 mg dissolved) is prepared, in which the polymer system undergoes a transition from a liquid to a gel upon exposure to a stimulus.

A polymer system comprising 15 mg/mL of Compound AA2 from TABLE 2 and pNNAD-4 (10 mg dissolved) is prepared, in which the polymer system undergoes a transition from a liquid to a gel upon exposure to a stimulus.

A polymer system comprising 15 mg/mL of Compound AA98 from TABLE 2 and pNNAD-4 (10 mg dissolved) is prepared, in which the polymer system undergoes a transition from a liquid to a gel upon exposure to a stimulus.

A polymer system comprising 15 mg/mL of Compound 1 and pNNAD-8 (10 mg dissolved) is prepared, in which the polymer system undergoes a transition from a liquid to a gel upon exposure to a stimulus.

A polymer system comprising 15 mg/mL of Compound AA6 from TABLE 2 and pNNAD-8 (10 mg dissolved) is prepared, in which the polymer system undergoes a transition from a liquid to a gel upon exposure to a stimulus.

A polymer system comprising 15 mg/mL of Compound AA28 from TABLE 2 and pNNAD-8 (10 mg dissolved) is prepared, in which the polymer system undergoes a transition from a liquid to a gel upon exposure to a stimulus.

A polymer system comprising 15 mg/mL of Compound AA2 from TABLE 2 and pNNAD-8 (10 mg dissolved) is prepared, in which the polymer system undergoes a transition from a liquid to a gel upon exposure to a stimulus.

A polymer system comprising 15 mg/mL of Compound AA98 from TABLE 2 and pNNAD-8 (10 mg dissolved) is prepared, in which the polymer system undergoes a transition from a liquid to a gel upon exposure to a stimulus.

A polymer system comprising 15 mg/mL of Compound 1 and pNNAD-12 (10 mg dissolved) is prepared, in which the polymer system undergoes a transition from a liquid to a gel upon exposure to a stimulus.

A polymer system comprising 15 mg/mL of Compound AA6 from TABLE 2 and pNNAD-12 (10 mg dissolved) is prepared, in which the polymer system undergoes a transition from a liquid to a gel upon exposure to a stimulus.

A polymer system comprising 15 mg/mL of Compound AA28 from TABLE 2 and pNNAD-12 (10 mg dissolved) is prepared, in which the polymer system undergoes a transition from a liquid to a gel upon exposure to a stimulus.

A polymer system comprising 15 mg/mL of Compound AA2 from TABLE 2 and pNNAD-12 (10 mg dissolved) is prepared, in which the polymer system undergoes a transition from a liquid to a gel upon exposure to a stimulus.

A polymer system comprising 15 mg/mL of Compound AA98 from TABLE 2 and pNNAD-12 (10 mg dissolved) is prepared, in which the polymer system undergoes a transition from a liquid to a gel upon exposure to a stimulus.

A hydrogel comprising 15 mg/mL of Compound 1 and 7.5 kDa hyaluronic acid (0.1 w/w %) is prepared, in which in situ polymerization occurs upon exposure to a stimulus.

A hydrogel comprising 15 mg/mL of AA6 from TABLE 2 and 7.5 kDa hyaluronic acid (0.1 w/w %) is prepared, in which in situ polymerization occurs upon exposure to a stimulus.

A hydrogel comprising 15 mg/mL of AA28 from TABLE 2 and 7.5 kDa hyaluronic acid (0.1 w/w %) is prepared, in which in situ polymerization occurs upon exposure to a stimulus.

A hydrogel comprising 15 mg/mL of AA2 from TABLE 2 and 7.5 kDa hyaluronic acid (0.1 w/w %) is prepared, in which in situ polymerization occurs upon exposure to a stimulus.

A hydrogel comprising 15 mg/mL of AA98 from TABLE 2 and 7.5 kDa hyaluronic acid (0.1 w/w %) is prepared, in which in situ polymerization occurs upon exposure to a stimulus.

A micelle comprising Compound 1 at about 5-50% the weight of the micelle, and a hydrophobic polymer, hydrophilic polymer, and a mucoadhesive at a ratio from about 0.5:94.5:5 to about 5:65:30, respectively, is prepared.

A micelle comprising AA6 from TABLE 2 at about 5-50% the weight of the micelle, and a hydrophobic polymer, hydrophilic polymer, and a mucoadhesive at a ratio from about 0.5:94.5:5 to about 5:65:30, respectively, is prepared.

A micelle comprising AA28 from TABLE 2 at about 5-50% the weight of the micelle, and a hydrophobic polymer, hydrophilic polymer, and a mucoadhesive at a ratio from about 0.5:94.5:5 to about 5:65:30, respectively, is prepared.

A micelle comprising AA2 from TABLE 2 at about 5-50% the weight of the micelle, and a hydrophobic polymer, hydrophilic polymer, and a mucoadhesive at a ratio from about 0.5:94.5:5 to about 5:65:30, respectively, is prepared.

A micelle comprising AA98 from TABLE 2 at about 5-50% the weight of the micelle, and a hydrophobic polymer, hydrophilic polymer, and a mucoadhesive at a ratio from about 0.5:94.5:5 to about 5:65:30, respectively, is prepared.

A photo-responsive therapeutic delivery system comprising 15 mg/mL of Compound 1 and PEG-anthracene is prepared, in which exposure of the delivery system to a light stimulus increases release of Compound 1 in a subject.

A photo-responsive therapeutic delivery system comprising 15 mg/mL of AA6 from TABLE 2 and PEG-anthracene is prepared, in which exposure of the delivery system to a light stimulus increases release of AA6 in a subject.

A photo-responsive therapeutic delivery system comprising 15 mg/mL of AA28 from TABLE 2 and PEG-anthracene is prepared, in which exposure of the delivery system to a light stimulus increases release of AA28 in a subject.

A photo-responsive therapeutic delivery system comprising 15 mg/mL of AA2 from TABLE 2 and PEG-anthracene is prepared, in which exposure of the delivery system to a light stimulus increases release of AA2 in a subject.

A photo-responsive therapeutic delivery system comprising 15 mg/mL of AA98 from TABLE 2 and PEG-anthracene is prepared, in which exposure of the delivery system to a light stimulus increases release of AA98 in a subject.

Embodiments

The following non-limiting embodiments provide illustrative examples of the invention, but do not limit the scope of the invention.

Embodiment 1. A polymeric matrix comprising a biopolymer and crosslinked hyaluronic acid, wherein the hyaluronic acid is cross-linked with a dendrimer, and the crosslinked hyaluronic acid is immobilized within the biopolymer.

Embodiment 2. A polymeric matrix as defined in embodiment 1, containing at least about 1% by weight of hyaluronic acid.

Embodiment 3. A polymeric matrix as defined in any one of embodiments 1-2, comprising a polymer selected from the group consisting of an acrylic-based polymer; and a silicone polymer.

Embodiment 4. A polymeric matrix as defined in embodiment 3, wherein the polymer is selected from the group consisting of poly methyl methacrylate, poly (hydroxyethyl methacrylate) (pHEMA), poly N-isopropyl acrylamide, and poly acrylic acid.

Embodiment 5. A polymeric matrix as defined in embodiment 3, wherein the polymer is a copolymer of methacryloxy propyl tris (trimethylsiloxy) silane (TRIS) and an acrylic-based polymer.

Embodiment 6. A polymeric matrix as defined in any one of embodiments 1-5, wherein the hyaluronic acid has a molecular weight of between about 6 kDa and 300 kDa.

Embodiment 7. A polymeric matrix as defined in any one of embodiments 1-6, wherein the hyaluronic acid has a molecular weight of between about 30 kDa and about 180 kDa.

Embodiment 8. A polymeric matrix as defined in any one of embodiments 1-7, having a surface friction which is reduced by at least about 10% in comparison with the surface friction of a corresponding biopolymer that is not modified to incorporate hyaluronic acid.

Embodiment 9. A polymeric matrix as defined in any one of embodiments 1-8, characterized by reduced protein adsorption of at least about 10% in comparison with a corresponding biopolymer that is not modified to incorporate hyaluronic acid.

Embodiment 10. A polymeric matrix as defined in any one of embodiments 1-9, wherein the dendrimer comprises a core monomer selected from the group consisting of an alkyl-diamine, an alkyl dicarboxylic acid and an aldehyde-terminated core.

Embodiment 11. A polymeric matrix as defined in embodiment 10, wherein the dendrimer is selected from the group consisting of ethyl-diamine, propyl-diamine, malonic acid, succinic acid, adipic acid, and polyamidoamine (PAMAM).

Embodiment 12. A method of making hyaluronic acid-retaining biopolymer comprising the steps of a) incubating hyaluronic acid with a host polymer in the presence of a dendrimer under conditions suitable to result in hyaluronic acid uptake by the polymer; and b) incubating the hyaluronic acid polymer mixture with a facilitating agent for a period of time sufficient to result in crosslinking of the hyaluronic acid within the polymer.

Embodiment 13. A method as defined in embodiment 12, comprising a polymer selected from the group consisting of an acrylic-based polymer; and a silicone polymer.

Embodiment 14. A method as defined in embodiment 13, wherein the polymer is selected from the group consisting of poly methyl methacrylate, poly (hydroxyethyl methacrylate) (pHEMA), poly N-isopropyl acrylamide, and poly acrylic acid.

Embodiment 15. A method as defined in embodiment 12, wherein the polymer is a copolymer of methacryloxy propyl tris (trimethylsiloxy) silane (TRIS) and an acrylic-based polymer.

Embodiment 16. A method as defined in any one of embodiments 12-15, wherein the hyaluronic acid has a molecular weight of between about 6 kDa and 300 kDa.

Embodiment 17. A method as defined in any one of embodiments 12-16, wherein the hyaluronic acid has a molecular weight of between about 30 kDa and about 180 kDa.

Embodiment 18. A method as defined in any one of embodiments 12-17, wherein the dendrimer comprises a core monomer selected from the group consisting of an alkyl-diamine, an alkyl dicarboxylic acid, and an aldehyde-terminated core.

Embodiment 19. A polymeric matrix as defined in embodiment 18, wherein the dendrimer is selected from the group consisting of ethyl-diamine, propyl-diamine, malonic acid, succinic acid, adipic acid, and polyamidoamine (PAMAM).

Embodiment 20. A method as defined in any one of embodiments 12-19, wherein the facilitating agent is a carbodiimide.

Embodiment 21. A method as defined in any one of embodiments 12-20, wherein step (b) is conducted in the presence of a stability agent.

Embodiment 30. A polymer system useful for in vivo delivery of a therapeutic agent, wherein the polymer system comprises at least one transition co-monomer in an amount of about 50-99.5% by weight that renders the polymer system capable of reversible stimuli induced transition from a liquid to a gel, and an acrylated lactone-containing co-monomer in an amount of about 0.5-15% by weight, an amine-reactive co-monomer in an amount of up to about 15% by weight and a hydrophilic co-monomer in an amount up to about 15% by weight, wherein the transition co-monomer, amine-reactive co-monomer, hydrophilic co-monomer and the acrylated lactone-containing co-monomer are polymerized within the polymer system and wherein the lactone ring of the acrylated lactone-containing co-monomer exists as a side chain within the polymer system which is subject to hydrolytic ring opening but remains attached to the polymer system to transition the polymer system from a gel to a liquid under physiological conditions.

Embodiment 31. The polymer system of embodiment 30, wherein the transition co-monomer is a co-monomer of a polymer selected from the group consisting of an acrylic-based polymer, a polyurethane, a polyurethane urea, a silicone polymer, a polyvinyl alcohol, and protein-based polymer.

Embodiment 32. The polymer system of embodiment 31, wherein the acrylic-based polymer is selected from the group consisting of polymethylmethacrylate, poly(hydroxyethyl methacrylate) (pHEMA), poly N-isopropyl acrylamide (NIPAAm), and polyacrylic acid.

Embodiment 33. The polymer system of any one of embodiments 30-32, wherein the acrylated lactone-containing co-monomer is acryloyloxy dimethyl-γ-butyrolactone (DBA).

Embodiment 34. The polymer of any one of embodiments 30-33, wherein the amine-reactive co-monomer is a succinide-containing monomer.

Embodiment 35. The polymer of any one of embodiments 30-34, wherein a therapeutic agent is bound to the polymer.

Embodiment 36. The polymer of any one of embodiments 30-35, additionally comprising an amine-terminated cell-adhesion agent.

Embodiment 37. The polymer of embodiment 36, wherein the cell-adhesion agent is selected from the group consisting of RODS, REDV, YIGSR, IKVAV, and GFOGER.

Embodiment 38. The polymer of embodiments 30-37, which transitions from a liquid to a gel at a temperature that is greater than room temperature.

Embodiment 39. A method of delivering a therapeutic agent to a target site in vivo comprising administering a polymer system as a solution to the target site, wherein the polymer system comprises at least one transition co-monomer in an amount of about 50-99.5% by weight that renders the polymer system capable of reversible stimuli induced transition from a liquid to a gel, and an acrylated lactone-containing co-monomer in an amount of about 0.5-15% by weight, an amine-reactive co-monomer in an amount of up to about 15% by weight and a hydrophilic co-monomer in an amount up to about 15% by weight, wherein the transition co-monomer, amine-reactive co-monomer, hydrophilic co-monomer and the acrylated lactone-containing co-monomer are polymerized within the polymer system and wherein the lactone ring of the acrylated lactone-containing co-monomer exists as a side chain within the polymer system which is subject to hydrolytic ring opening but remains attached to the polymer system to transition the polymer system from a gel to a liquid under physiological conditions; and wherein the polymer system comprises a therapeutic agent.

Embodiment 40. The method of embodiment 38, wherein the transition co-monomer forms an acrylic-based polymer selected from the group consisting of polymethylmethacrylate, poly(hydroxyethyl methacrylate) (pHEMA), poly N-isopropyl acrylamide (NIPAAm) and polyacrylic acid, and the degradable co-monomer is selected from the group consisting of lactone-containing co-monomer, poly(lactic acid), poly(glycolic acid), poly(glycolic-co-lactic acid), poly (caprolactone), [poly(dioxanone), poly(3-hydroxybutyrate), poly(3-hydroxyvalcrate), poly(valcrolactone), poly(tartonic acid), poly(malonic acid)], poly(anhydrides), poly(orthoesters), and polyphosphazenes.

Embodiment 41. The method of embodiment 38, wherein the polymer comprises amine-reactive co-monomer to which the therapeutic agent is bound.

Embodiment 42. The method of embodiment 38, wherein the polymer transitions from a liquid to a gel on administration to the target site.

Embodiment 50. Biocompatible mucoadhesive block copolymer micelles comprising a degradable hydrophobic polymer, a degradable synthetic hydrophilic polymer and a mucoadhesive component.

Embodiment 51. The micelles of embodiment 50, wherein the hydrophobic polymer is selected from the group consisting of polyesters, polyurethanes, polyureas, polycarbonates, polyethers, polysulfides, polysulfonates, polyimides, polybenzimidazoles, a lipoglycan, a proteoglycan, and combinations thereof.

Embodiment 52. The micelles of embodiment 51, wherein the hydrophobic polymer is a polylactide, polyglycolide, poly(lactide-co-glycolide), poly($\varepsilon$-caprolactone), poly-3-hydroxybutyrate, poly(dioxanone), poly(3-hydroxybutyrate), poly(3-hydroxyvalcrate), poly(valcrolactone), poly(tartonic acid), poly(malonic acid), poly(anhydrides), poly(orthoesters), polyphosphazenes and acryloyloxy dimethyl-.gamma.-butyrolactone (DBA), or a combination thereof.

Embodiment 53. The micelles of any one of embodiments 50-52, wherein the synthetic hydrophilic polymer is selected from the group consisting of methacrylic acid, acrylic acid, hydroxyethyl methacrylate, hydroxypropylmethacrylamide, hydroxyethyl acrylate, poly(ethylene glycol) methacrylate, poly(N-isopropylacrylamide) (PNIPAM), poly(vinyl alcohol) (PVA), poly(2-oxazoline), polyethylene glycol, polyvinylpyrollidone, and copolymers thereof.

Embodiment 54. The micelles of any one of embodiments 50-53, wherein the mucoadhesive component is selected from the group consisting of a boronic acid or derivative thereof, a thiol-containing compound, an acrylate, chitosan, cellulose, thiolated chitosan, thiolated hyaluronic acid, thiolated poly(acrylic) acid, and mixtures thereof.

Embodiment 55. The micelles of any one of embodiments 50-54, wherein the mucoadhesive component is a boronic acid or a boronic ester.

Embodiment 56. The micelles of embodiment 54, wherein the boronic acid or derivative thereof is selected from the group consisting of phenylboronic acid, 2-thienylboronic acid, methylboronic acid, cis-propenylboronic acid, trans-propenylboronic acid, (4-allylaminocarbonyl)benzeneboronic acid, (4-aminosulfonylphenyl)boronic acid, (4-benzyloxy-2-formyl)phenylboronic acid, (4-hydroxy-2-methyl) phenylboronic acid, (4-hydroxy-2-methyl)phenylboronic acid, (4-methanesulfonylaminomethylphenyl)boronic acid, (4-methanesulfonylaminomethylphenyl)boronic acid, (4-methylaminosulfonyl-phenyl)boronic acid, (4-methyl aminosulfonylphenyl)boronic acid, (4-phenylamino-carbonylphenyl)boronic acid, (4-phenylaminocarbonylphenyl)boronic acid, (4-sec-butyl) benzeneboronic acid, (2,6-dimethoxy-4-methylphenyl)boronic acid, (2,6-dimethoxy-4-methylphenyl)boronic acid, (2-methylpropyl)boronic acid, (2-methylpropyl) boronic acid, (3-acetamido-5-carboxy) phenylboronic acid, (3-acetamido-5-carboxy) phenyl boronic acid, (3-acetamidomethylphenyl)boronic acid, (3-acetamidomethylphenyl) boronic acid, (3-allylaminocarbonyl)benzeneboronic acid, (3-cyanomethylphenyl)boronic acid, allylboronic acid pinacol ester, phenyl boronic acid trimethylene glycol ester, diisopropoxymethylborane, bis(hexyleneglycolato)diboron, t-butyl-N-[4-(4,4,5,5-tetramethyl-1,3,2-dioxaborolan-2-yl)phenyl]carbamat-e, 2,6-dimethyl-4-(4,4,5,5-tetramethyl1,3,2-dioxaborolan-2-yl) benzoate, 4-(4,4,5,5-tetramethyl1,3,2-dioxaborolan-2-yl) aniline, 4-(4,4,5,5-tetramethyl1,3,2-dioxaborolan-2-yl) benzoic acid, 4-(4,4,5,5-tetramethyl1,3,2-dioxaborolan-2-yl)phenol, and 2-methoxy-4-(4,4,5,5-tetramethyl1,3,2-dioxaborolan-2-yl)phenol.

Embodiment 57. The micelles of any one of embodiments 50-56, wherein the ratio of hydrophobic polymer:hydrophilic polymer:mucoadhesive is in the range of about 0.5:94.5:5 to about 5:65:30.

Embodiment 58. The micelles of any one of embodiments 50-57, which are less than about 200 nm in size.

Embodiment 59. The micelles of any one of embodiments 50-58, loaded with cargo.

Embodiment 60. The micelles of embodiment 59, wherein the cargo comprises about 5-50% by weight of the micelles.

Embodiment 61. The micelles of any one of embodiments 59-60, wherein the cargo is selected from a therapeutic agent and a diagnostic agent.

Embodiment 62. The micelles of any one of embodiments 59-61, wherein the cargo is selected from the group consisting of analgesics, anti-inflammatory agents, anti-pathogenic agents including antibacterial, antiviral and antifungal agents, gastrointestinal agents, anti-histamines, anti-allergic agents, anti-cancer agents, anti-nauseants, anti-asthmatic agents, decongestants, glaucoma medication, intra-ocular pressure lowering drugs (IOP-lowering agents), lubricants, demulcents, counter-irritants, hypertonic tears, anti-ototoxic agents, proteins, nucleic acids, and carbohydrates.

Embodiment 63. The micelles of embodiment 59, wherein the cargo is an ophthalmic drug.

Embodiment 64. The micelles of embodiment 63, wherein the ophthalmic drug is selected from the group consisting of cyclosporine A, acyclovir, atropine, acetazolamide, alphagan, azithromycin, bacitracin, betadine, betaxolol (Betoptic®), betoptic, brinzolamide, carbachol, cefazolin, carboxymethylcellulose sodium (Celluvisc®), chloramphenicol, ciprofloxacin (Ciloxan®), cephalosporin, emecarium, dexamethasone, dipivefrin, dorzolamide, epinephrine, erythromycin, fluorescein, flurbiprofen, quinolones such as fluoroquinolone, gentamicin, hydroxypropyl methylcellulose (Goniosol®), gramicidin, gancyclovir, gatafloxacin, demecarium (Humorsol®), sodium hyaluronate (Hylartin®), itraconazole, ketotifen, latanoprost, levofloxacin, bimatoprost, travoprost, pilocarpine, polymyxin B, prednisolone, proparacaine, dipivefrine (Propine®), petrolatum (Puralube®), mannitol, methazolamide, miconazole, carbachol (Miostat®), moxifloxacin, natamycin, neomycin, methazolamide (Neptazane®), ofloxacin (Ocuflox®), oxytetracycline, olopatadine, phenylephrine, prostaglandin, sodium hyaluronate, suprofen, oxytetracycline (Terramycin®), timolol, tobramycin, triamcinolone, trifluridine, tropicamide, vidarabine, valcyclovir, vancomycin, latanoprost (Xalatan®), phenylephrine, a prostaglandin, and an anti-VEGF drug.

Embodiment 65. A composition comprising the micelles of embodiment 50 combined with a pharmaceutically acceptable carrier.

Embodiment 66. The composition of embodiment 65, formulated for oral, intranasal, enteral, topical, sublingual, intra-arterial, intramedullary, intrauterine, intrathecal, inhalation, ocular, transdermal, vaginal, rectal, subcutaneous, intraperitoneal, intramuscular, or intravenous administration.

Embodiment 67. The composition of any one of embodiments 65-66, formulated for topical administration to the eye or ear.

Embodiment 68. A method of delivering cargo to a mucosal surface in a mammal comprising administering to the mammal micelles as defined in embodiment 59.

Embodiment 69. The method of embodiment 68, wherein the method is to treat or diagnose a pathogenic condition affecting the eye, nose, mouth, ear, throat, esophagus, stomach, intestines, endometrium, penis, vagina, or anus.

Embodiment 70. The method of embodiment 69, wherein the pathogenic condition is infection, inflammation, cancer, degenerative disease, allergic reaction, or mechanical injury.

Embodiment 71. The method of embodiment 68, wherein the cargo is selected from the group consisting of analgesics, anti-inflammatory agents, anti-pathogenic agents, including antibacterial, antiviral and antifungal agents, gastrointestinal agents, anti-histamines, anti-allergic agents, anti-cancer agents, anti-nauseants, anti-asthmatic agents, decongestants, glaucoma medication, intra-ocular pressure lowering drugs (IOP-lowering agents), lubricants, demulcents, counter-irritants, hypertonic tears, anti-ototoxic agents, proteins, nucleic acids, and carbohydrates.

Embodiment 72. The method of embodiment 68, wherein the cargo is an ophthalmic drug.

Embodiment 73. A mucoadhesive-based ophthalmic drug delivery system comprising poly(L-lactide)-b-poly(methacrylic acid-co-phenylboronic acid) copolymer micelles.

Embodiment 74. The drug delivery system of embodiment 73, additionally comprising an ophthalmic drug.

Embodiment 75. The drug delivery system of any one of embodiments 73-74, selected from the group consisting of cyclosporine A, acyclovir, atropine, acetazolamide, brimonidine (Alphagan®), azithromycin, bacitracin, betadine, betaxolol (Betoptic®), brinzolamide, carbachol, cefazolin, carboxymethylcellulose sodium (Celluvisc®), chloramphenicol, ciprofloxacin (Ciloxan®), cephalosporin, emecarium, dexamethasone, dipivefrin, dorzolamide, epinephrine, erythromycin, fluorescein, flurbiprofen, quinolones such as fluoroquinolone, gentamicin, hydroxypropyl methylcellulose (Goniosol®), gramicidin, gancyclovir, gatafloxacin, demecarium (Humorsol®), sodium hyaluronate (Hylartin®), itraconazole, ketotifen, latanoprost, levofloxacin, bimatoprost, travoprost, pilocarpine, polymyxin B, prednisolone, proparacaine, dipivefrine (Propine®), petrolatum (Puralube®), mannitol, methazolamide, miconazole, carbachol (Miostat®), moxifloxacin, natamycin, neomycin, methazolamide (Neptazane®), ofloxacin (Ocuflox®), oxytetracycline, olopatadine, phenylephrine, prostaglandin, sodium hyaluronate, suprofen, oxytetracycline (Terramycin®), timolol, tobramycin, triamcinolone, trifluridine, tropicamide, vidarabine, valcyclovir, vancomycin, latanoprost (Xalatan®), phenylephrine, a prostaglandin, and an anti-VEGF drug.

Embodiment 76. The drug delivery system of any one of embodiments 73-75, wherein the ophthalmic drug is cyclosporine A.

Embodiment 80. A method of in situ hydrogel polymerization comprising the steps of: 1) modifying a biocompatible backbone polymer with an in situ polymerizable group to form a prepolymer solution; 2) administering the prepolymer solution to a target site; and 3) exposing the prepolymer solution to a stimulus that induces polymerization of the solution at the target site.

Embodiment 81. The method of embodiment 80, wherein the target site is an in vivo target site.

Embodiment 82. The method of any one of embodiments 80-81, wherein the target site is an ophthalmic site.

Embodiment 83. The method of any one of embodiments 80-82, wherein the stimulus is selected from the group consisting of heat and light.

Embodiment 84. The method of embodiment 83, wherein the stimulus is exposure to body temperature.

Embodiment 85. The method of any one of embodiments 80-84, wherein at least one of a crosslinking agent, a facilitating agent, a stability agent, a polymerization initiating agent and a utility-specific component is added to the prepolymer solution.

Embodiment 86. The method of embodiment 85, wherein the polymerization initiating agent is a photo-initiator.

Embodiment 87. The method of embodiment 85, wherein the utility-specific component is a UV-absorbing molecule.

Embodiment 88. The method of any one of embodiments 80-87, wherein the backbone polymer is selected from the group consisting of hyaluronate and collagen.

Embodiment 89. The method of any one of embodiments 80-88, wherein the polymerizable group is selected from the group consisting of a methacrylate, an acrylamide, an acrylic acid, a urethane, silicone polymers and hydrogel polymers.

Embodiment 90. A prepolymer solution a comprising a collagen backbone and an acrylamide polymerizing agent.

Embodiment 91. The solution of embodiment 90, wherein the solution is polymerizable on exposure to body temperature.

Embodiment 92. A kit comprising a polymer backbone and a polymerizable group which may be combined to form a prepolymer solution that is polymerizable on exposure to body temperature.

Embodiment 93. The kit of embodiment 92, optionally comprising one or more of a crosslinking agent, a facilitating agent, a stability agent, a polymerization initiating agent and a utility-specific component.

Embodiment 94. A kit as defined in embodiment 93, wherein the polymer backbone and polymerizable group have been combined to form a prepolymer solution, and wherein the kit additionally comprises a polymerization initiating agent.

Embodiment 95. An article of manufacture comprising packaging material and a kit as defined in embodiment 94, wherein the packaging material is labeled to indicate that the prepolymer solution is for use to be administered to a target site for in situ polymerization on exposure to a stimulus that induces polymerization at the target site.

Embodiment 96. The article of any one of embodiments 94-95, optionally comprising one or more of a crosslinking agent, a facilitating agent, a stability agent, a polymerization initiating agent and a utility-specific component.

Embodiment 100. A method of reducing intraocular pressure in a subject in need thereof, the method comprising administering to the subject a pharmaceutical composition, in a unit dosage form, wherein the pharmaceutical composition comprises a Tie-2 activator; and a pharmaceutically-acceptable excipient.

Embodiment 101. The method of embodiment 100, wherein the Tie-2 activator increases aqueous humor drainage in the subject.

Embodiment 102. The method of any one of embodiments 100-101, wherein the Tie-2 activator increases aqueous humor drainage downstream of Schlemm's canal in the subject.

Embodiment 103. The method of any one of embodiments 100-102, wherein the Tie-2 activator increases lymphatic drainage of Schlemm's canal in the subject.

Embodiment 104. The method of any one of embodiments 100-103, wherein the Tie-2 activator increases lymphatic drainage in a corneal limbal lymphatic system in the subject.

Embodiment 105. The method of any one of embodiments 100-104, wherein the Tie-2 activator causes vasodilation of a vessel downstream of Schlemm's canal in the subject.

Embodiment 106. The method of any one of embodiments 100-105, wherein the Tie-2 activator causes vasorelaxation of a smooth muscle cell in or around a vessel downstream of Schlemm's canal in the subject.

Embodiment 107. The method of any one of embodiments 100-106, wherein the Tie-2 activator activates Tie-2 in or around a vessel downstream of Schlemm's canal in the subject.

Embodiment 108. The method of any one of embodiments 100-107, wherein the Tie-2 activator inhibits HPTPβ in or around a vessel downstream of Schlemm's canal in the subject.

Embodiment 109. The method of any one of embodiments 105-108, wherein the vessel is a limbal vascular plexus.

Embodiment 110. The method of any one of embodiments 105-108, wherein the vessel is a superficial vascular plexus (SVP).

Embodiment 111. The method of any one of embodiments 105-108, wherein the vessel is a superficial capillary plexus (SCP).

Embodiment 112. The method of any one of embodiments 105-108, wherein the vessel is an episcleral vein.

Embodiment 113. The method of any one of embodiments 100-112, wherein the Tie-2 activator does not cause a morphological change in Schlemm's canal in the subject.

Embodiment 114. The method of embodiment 113, wherein the morphological change in Schlemm's canal is at the inner wall of Schlemm's canal.

Embodiment 115. The method of embodiment 113, wherein the morphological change in Schlemm's canal is reduction in Schlemm's canal area.

Embodiment 116. The method of any one of embodiments 100-115, wherein the Tie-2 activator provides neuroprotection in an eye of the subject.

Embodiment 117. The method of any one of embodiments 100-116, wherein the Tie-2 activator decreases retinal ganglion cell death in the subject.

Embodiment 118. The method of embodiment 117, wherein the retinal ganglion cell death is caused by elevated intraocular pressure in the subject.

Embodiment 119. The method of any one of embodiments 100-118, further comprising administering to the subject a vasorelaxant or a vasodilator.

Embodiment 120. The method of embodiment 119, wherein the vasorelaxant or the vasodilator is an alpha-adrenoceptor antagonist (alpha-blocker), an angiotensin converting enzyme (ACE) inhibitor, an angiotensin receptor blocker (ARB), a beta2-adrenoceptor agonist (β2-agonist), a calcium-channel blocker (CCB), a centrally acting sympatholytic, a direct acting vasodilator, an endothelin receptor antagonist, a ganglionic blocker, a nitrodilator, a phosphodiesterase inhibitor, a potassium-channel opener, or a renin inhibitor.

Embodiment 121. The method of any one of embodiments 100-120, wherein the Tie-2 activator is a small molecule.

Embodiment 122. The method of any one of embodiments 100-120, wherein the Tie-2 activator is a biologic.

Embodiment 123. The method of any one of embodiments 100-122, wherein the Tie-2 activator is MAN-01.

In some embodiments, the disclosure provides a pharmaceutical composition comprising, in a unit dosage form: a Tie-2 activator; and a pharmaceutically-acceptable excipient that releases the Tie-2 activator from the unit dosage form at a rate that is about zero order with respect to the Tie-2 activator. In some embodiments, the disclosure provides a pharmaceutical composition comprising, in a unit dosage form: a Tie-2 activator; and a pharmaceutically-acceptable excipient that releases the Tie-2 activator from the unit dosage form without an initial burst of the Tie-2 activator. In some embodiments, the disclosure provides a pharmaceutical composition comprising, in a unit dosage form: a Tie-2 activator; and a pharmaceutically-acceptable excipient that releases the Tie-2 activator from the unit dosage form over a period of at least one month. In some embodiments, the disclosure provides a pharmaceutical composition comprising, in a unit dosage form: a Tie-2 activator; and a pharmaceutically-acceptable excipient that releases the Tie-2 activator from the unit dosage form over a period of at least four months. In some embodiments, the disclosure provides a pharmaceutical composition comprising, in a unit dosage form: a Tie-2 activator; and a pharmaceutically-acceptable excipient that releases the Tie-2 activator from the unit dosage form over a period of at least six months. In some embodiments, the disclosure provides a pharmaceutical composition comprising, in a unit dosage form: a Tie-2 activator; and a polymer that comprises a phenylboronic acid moiety. In some embodiments, the disclosure provides a pharmaceutical composition comprising, in a unit dosage form: a Tie-2 activator; and a polymer that comprises: a portion that is polylactide; a portion that is polymethacrylic acid; and a monomer that comprises a phenylboronic acid unit. In some embodiments, the disclosure provides a pharmaceutical composition comprising, in a unit dosage form: a Tie-2 activator; and a copolymer of two components that are O-methacrylated vitamin E and an ester of methacrylic acid and a polyethylene glycol moiety. In some embodiments, the Tie-2 activator is MAN-01.

In some embodiments, the disclosure provides a pharmaceutical composition in a unit dosage form comprising a compound that is a Tie-2 activator or a HPTPβ inhibitor, and a pharmaceutically-acceptable excipient. In some embodiments, the pharmaceutically-acceptable excipient releases the compound from the unit dosage form at a rate that is about zero order with respect to the compound. In some embodiments, the pharmaceutically-acceptable excipient releases the compound from the unit dosage form without an initial burst of the compound. In some embodiments, the pharmaceutically-acceptable excipient releases the compound from the unit dosage form over a period of at least one month, at least four months, or at least six months. In some embodiments, the pharmaceutical composition is a solution. In some embodiments, the pharmaceutical composition is a drop. In some embodiments, the pharmaceutical composition is a gel. In some embodiments, the pharmaceutical composition is a nanogel. In some embodiments, the pharmaceutical composition comprises a nanofibrous hydrogel network. In some embodiments, the pharmaceutical composition comprises a micelle. In some embodiments, the pharmaceutical composition comprises a mucoadhesive micelle. In some embodiments, the pharmaceutical composition comprises a shear-responsive ophthalmic hydrogel. In some embodiments, the pharmaceutical composition comprises a thermoresponsive polymer scaffold. In some embodiments, the pharmaceutically-acceptable excipient is an in situ gelling agent. In some embodiments, the pharmaceutically-acceptable excipient is vitamin E. In some embodiments, the pharmaceutically-acceptable excipient is polyethylene glycol. In some embodiments, the pharmaceutically-acceptable excipient comprises a phenylboronic acid moiety. In some embodiments, the pharmaceutically-acceptable excipient is a cellulose. In some embodiments, the pharmaceutically-acceptable excipient is methyl cellulose. In some embodiments, the pharmaceutically-acceptable excipient is a silicone elastomer. In some embodiments, the pharmaceutically-acceptable excipient is hydrophobically modified poly(vinyl pyrrolidone). In some embodiments, the pharmaceutically-acceptable excipient is a polymer that comprises a portion that is poly(N-tert-butylacrylamide). In some embodiments, the pharmaceutically-acceptable excipient is a polymer that comprises a portion that is poly(oligoethylene glycol methacrylate). In some embodiments, the pharmaceutically-acceptable excipient is a polymer that comprises a portion that is polylactide. In some embodiments, the pharmaceutically-acceptable excipient is a polymer that comprises a portion that is polymethacrylic acid. In some embodiments, the pharmaceutically-acceptable excipient is a polymer that comprises: a portion that is polylactide; a portion that is polymethacrylic acid; and a monomer that comprises a phenylboronic acid unit, wherein the pharmaceutical composition comprises a population of molecules the polymer, wherein the molecules in the population of the polymer have an average molecular weight of about 10 kDa. In some embodiments, the pharmaceutically-acceptable excipient is a copolymer of two components that are O-methacrylated vitamin E and an ester of methacrylic acid and a polyethylene glycol moiety. In some embodiments, the O-methacrylated vitamin E is γ-tocopherol-O-methacrylate. In some embodiments, the ester of methacrylic acid and the polyethylene glycol moiety is polyethylene glycol methyl ether methacrylate. In some embodiments, the ester of methacrylic acid and the polyethylene glycol moiety is polyethylene glycol ethyl ether methacrylate. In some embodiments, the two components of the copolymer are present in a ratio of from 2:1 to 1:2. In some embodiments, the pharmaceutical composition comprises a population of molecules the copolymer, wherein the molecules in the population of the copolymer have an average molecular weight of about 20 kDa. In some embodiments, the pharmaceutical composition comprises a population of molecules the copolymer, wherein the molecules in the population of the copolymer have an average molecular weight of about 50 kDa. In some embodiments, the pharmaceutical composition comprises a population of molecules the copolymer, wherein the molecules in the population of the copolymer have an average molecular weight of about 100 kDa. In some embodiments, the compound is poorly soluble in water. In some embodiments, the compound is a phosphatase inhibitor. In some embodiments, the disclosure provides a method of treating a condition, the method comprising administering to a subject in need thereof a therapeutically-effective amount of a pharmaceutical composition as described above. In some embodiments, after administering the pharmaceutical composition to the subject, the pharmaceutical composition releases the compound at a rate that is about zero order with respect to the compound. In some embodiments, after administering the pharmaceutical composition to the subject, the pharmaceutical composition releases the compound without an initial burst of the compound. In some embodiments, after administering the pharmaceutical composition to the subject, the pharmaceutical composition releases the compound over a period of at least one month. In some embodiments, after administering the pharmaceutical composition to the subject, the pharmaceutical composition releases the compound over a period of at least four months. In some embodiments, after administering the pharmaceutical composition to the subject, the pharmaceutical composition releases the compound over a period of at least six months. In some embodiments, the administering is to an eye of the subject. In some embodiments, the administering is by intraocular injection. In some embodiments, the administering is by subcutaneous injection. In some embodiments, the administering is topical. In some embodiments, the administering provides the compound to a posterior portion of an eye of the subject. In some embodiments, the administering provides the compound to an anterior portion of an eye of the subject. In some embodiments, the administering occurs once every month. In some embodiments, the administering occurs once every month, and no more than once every month. In some embodiments, the administering occurs once every three months. In some embodiments, the administering occurs once every three months, and no more than once every three months. In some embodiments, the administering occurs once every six months. In some embodiments, the administering occurs once every six months, and no more than once every six months. In some embodiments, after administering the pharmaceutical composition to the subject, the pharmaceutical composition gels in situ in the subject. In some embodiments, the administering is to an eye of the subject, wherein after administering the pharmaceutical composition to the eye of the subject, the pharmaceutical composition gels in situ in the eye of the subject. In some embodiments, the condition is vision loss. In some embodiments, the condition is acute kidney injury. In some embodiments, the condition is influenza. In some embodiments, the condition is myocardial ischemia. In some embodiments, the condition is macular degeneration. In some embodiments, the condition is glaucoma. In some embodiments, the condition is primary open angle glaucoma. In some embodiments, the Tie-2 activator or the HPTPβ inhibitor is MAN-01.

What is claimed is:

1. A pharmaceutical composition comprising, in a unit dosage form: a Tie-2 activator; and a micelle, wherein the micelle comprises a mucoadhesive component, wherein the Tie-2 activator is a compound of the formula:

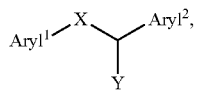

wherein:
Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thioether linkage, a carbamate linkage, a carbonate linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

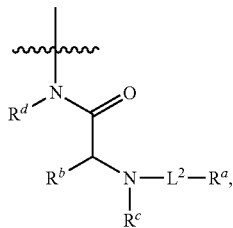

wherein:
L$^2$ is alkylene, alkenylene, or alkynylene, any of which is substituted or unsubstituted, or together with the nitrogen atom to which L$^2$ is bound forms an amide linkage, a carbamate linkage, or a sulfonamide linkage, or a chemical bond, or together with any of R$^a$, R$^b$, R$^c$, and R$^d$ forms a ring that is substituted or unsubstituted;
R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^b$, R$^c$, and R$^d$ forms a ring that is substituted or unsubstituted;
R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L$^2$, R$^a$, R$^c$, and R$^d$ forms a ring that is substituted or unsubstituted;
R$^c$ is H or alkyl which is substituted or unsubstituted, or together with any of L$^2$, R$^a$, R$^b$, and R$^d$ forms a ring that is substituted or unsubstituted;
R$^d$ is H or alkyl which is substituted or unsubstituted, or together with any of L$^2$, R$^a$, R$^b$, and R$^c$ forms a ring that is substituted or unsubstituted; and
R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

2. The pharmaceutical composition of claim 1, wherein the pharmaceutical composition is a solution.

3. The pharmaceutical composition of claim 1, wherein the pharmaceutical composition is a drop.

4. The pharmaceutical composition of claim 1, wherein the pharmaceutical composition is a gel.

5. The pharmaceutical composition of claim 1, wherein the pharmaceutical composition is formulated for topical administration.

6. The pharmaceutical composition of claim 1, wherein the pharmaceutical composition is formulated for administration to an eye.

7. The pharmaceutical composition of claim 1, wherein the micelle is less than 200 nm in size.

8. The pharmaceutical composition of claim 1, wherein the micelle further comprises a degradable hydrophobic polymer and a degradable synthetic hydrophilic polymer.

9. The pharmaceutical composition of claim 8, wherein the micelle comprises the degradable hydrophobic polymer, the degradable hydrophilic polymer, and the mucoadhesive component at a ratio from about 0.5:94.5:5 to about 5:65:30, respectively.

10. The pharmaceutical composition of claim 8, wherein the degradable hydrophobic polymer is a polylactide, polyglycolide, poly(lactide-co-glycolide), poly(ε-caprolactone), poly-3-hydroxybutyrate, poly(dioxanone), poly(3-hydroxybutyrate), poly(3-hydroxyvalerate), poly(valerolactone), poly(tartaric acid), poly(malonic acid), poly(anhydrides), poly(orthoesters), polyphosphazenes and acryloyloxy dimethyl-γ-butyrolactone (DBA), or a combination thereof.

11. The pharmaceutical composition of claim 8, wherein the degradable synthetic hydrophilic polymer is selected from the group consisting of methacrylic acid, acrylic acid, hydroxyethyl methacrylate, hydroxypropylmethacrylamide, hydroxyethyl acrylate, poly(ethylene glycol) methacrylate, poly(N-isopropylacrylamide) (PNIPAM), poly(vinyl alcohol) (PVA), poly(2-oxazoline), polyethylene glycol, polyvinylpyrrolidone, and copolymers thereof.

12. The pharmaceutical composition of claim 1, wherein the mucoadhesive component is selected from the group consisting of a boronic acid or derivative thereof, a thiol-containing compound, an acrylate, chitosan, cellulose, thiolated chitosan, thiolated hyaluronic acid, thiolated poly(acrylic) acid, and mixtures thereof.

13. The pharmaceutical composition of claim 1, wherein the mucoadhesive component is a boronic acid.

14. The pharmaceutical composition of claim 1, wherein the mucoadhesive component is a boronic ester.

15. The pharmaceutical composition of claim 1, wherein the mucoadhesive component is a phenylboronic acid moiety.

16. The pharmaceutical composition of claim 1, wherein the micelle is a biocompatible mucoadhesive block copolymer micelle.

17. The pharmaceutical composition of claim 1, wherein the micelle is a poly(L-lactide)-b-poly(methacrylic acid-co-phenylboronic acid) copolymer micelle.

18. The pharmaceutical composition of claim 1, wherein the micelle comprises the Tie-2 activator at about 5-50% the weight of the micelle.

19. The pharmaceutical composition of claim 1, wherein the pharmaceutical composition comprises a shear-responsive ophthalmic hydrogel.

20. The pharmaceutical composition of claim 1, wherein the pharmaceutical composition comprises a thermoresponsive polymer scaffold.

21. The pharmaceutical composition of claim 1, wherein the pharmaceutical composition comprises an in situ gelling agent.

22. The pharmaceutical composition of claim 1, wherein the micelle comprises a portion that is poly(oligoethylene glycol methacrylate).

23. The pharmaceutical composition of claim 1, wherein the micelle comprises a portion that is polylactide.

24. The pharmaceutical composition of claim 1, wherein the micelle comprises a portion that is polymethacrylic acid.

25. The pharmaceutical composition of claim 1, wherein the micelle comprises: a portion that is polylactide; a portion that is polymethacrylic acid; and a monomer that comprises a phenylboronic acid unit, wherein the pharmaceutical composition comprises a population of molecules of the polymer, wherein the molecules in the population of the polymer have an average molecular weight of about 10 kDa.

26. The pharmaceutical composition of claim 1, wherein the Tie-2 activator is an inhibitor of HPTPβ.

* * * * *